(12) United States Patent
Yonemura et al.

(10) Patent No.: US 10,123,537 B2
(45) Date of Patent: Nov. 13, 2018

(54) AMIDE COMPOUND OR SALT THEREOF, AGRICULTURAL AND HORTICULTURAL INSECTICIDE AND MICROBICIDE COMPRISING THE COMPOUND, AND METHOD FOR USING THE INSECTICIDE AND MICROBICIDE

(71) Applicant: NIHON NOHYAKU CO., LTD., Tokyo (JP)

(72) Inventors: Ikki Yonemura, Osaka (JP); Soichiro Matsuo, Osaka (JP); Akiyuki Suwa, Osaka (JP); Masao Yamashita, Osaka (JP); Atsushi Okada, Osaka (JP)

(73) Assignee: NIHON NOHYAKU CO., LTD., Tokyo (JP)

( * ) Notice: Subject to any disclaimer, the term of this patent is extended or adjusted under 35 U.S.C. 154(b) by 0 days.

(21) Appl. No.: 15/668,999

(22) Filed: Aug. 4, 2017

(65) Prior Publication Data
US 2017/0332635 A1   Nov. 23, 2017

Related U.S. Application Data

(62) Division of application No. 15/035,252, filed as application No. PCT/JP2014/079879 on Nov. 11, 2014, now Pat. No. 9,888,686.

(30) Foreign Application Priority Data

Nov. 12, 2013 (JP) ................. 2013-233965
Jul. 15, 2014 (JP) ................. 2014-145317

(51) Int. Cl.
| | | |
|---|---|---|
| *A01N 43/40* | (2006.01) |
| *C07D 401/12* | (2006.01) |
| *C07D 237/20* | (2006.01) |
| *C07D 213/75* | (2006.01) |
| *C07C 323/62* | (2006.01) |
| *C07C 317/44* | (2006.01) |
| *A01N 41/02* | (2006.01) |
| *A01N 55/00* | (2006.01) |
| *A01N 43/58* | (2006.01) |
| *A01N 41/12* | (2006.01) |
| *A01N 41/10* | (2006.01) |

(Continued)

(52) U.S. Cl.
CPC ............. *A01N 43/40* (2013.01); *A01N 41/02* (2013.01); *A01N 41/04* (2013.01); *A01N 41/10* (2013.01); *A01N 41/12* (2013.01); *A01N 43/58* (2013.01); *A01N 55/00* (2013.01); *C07C 317/44* (2013.01); *C07C 323/42* (2013.01); *C07C 323/62* (2013.01); *C07D 213/75* (2013.01); *C07D 237/20* (2013.01); *C07D 401/12* (2013.01); *C07F 7/081* (2013.01)

(58) Field of Classification Search
CPC ........ A01N 43/40; A01N 41/02; A01N 41/04; A01N 41/10; A01N 41/12; A01N 43/58; A01N 55/00; C07C 317/44; C07C 323/42; C07C 323/62; C07D 213/75; C07D 237/20; C07D 401/12; C07F 7/0818
USPC .......................................................... 514/63
See application file for complete search history.

(56) References Cited

U.S. PATENT DOCUMENTS 5,360,806 A   11/1994 Toki et al.
5,508,416 A   4/1996 Kagano et al.
(Continued)

FOREIGN PATENT DOCUMENTS

EP   2 955 178       12/2015
JP   55151541     * 11/1980
(Continued)

OTHER PUBLICATIONS

"Foliar Diseases of Wheat", University of Illinois Extension, Report on Plant Disease, No. 104, May 1995, 6 pages. (Year: 1995).*
(Continued)

*Primary Examiner* — Daniel R Carcanague
(74) *Attorney, Agent, or Firm* — Wenderoth, Lind & Ponack, L.L.P.

(57) ABSTRACT

In crop production in the fields of agriculture, horticulture and the like, the damage caused by insect pests etc. is still immense, and insect pests resistant to existing insecticides have emerged. Under such circumstances, the development of novel agricultural and horticultural insecticides is desired. The present invention provides an amide compound represented by the general formula (I):

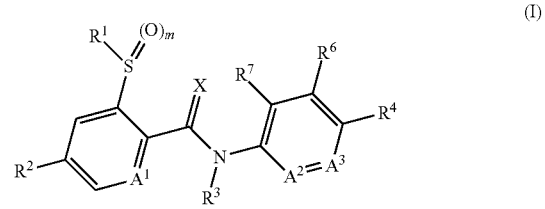

(wherein $A^1$, $A^2$ and $A^3$ each represent a nitrogen atom or a CH group, $R^1$ represents an alkyl group, $R^2$ and $R^4$ each represent a haloalkyl group, $R^3$ represents an alkyl group, and m represents 0, 1 or 2) or a salt thereof; an agricultural and horticultural insecticide and microbicide comprising the compound or a salt thereof as an active ingredient; and a method for using the insecticide and microbicide.

13 Claims, No Drawings

(51) Int. Cl.
*A01N 41/04* (2006.01)
*C07F 7/08* (2006.01)
*C07C 323/42* (2006.01)

(56) References Cited

U.S. PATENT DOCUMENTS

| | | | |
|---|---|---|---|
| 9,888,686 | B2* | 2/2018 | Yonemura ............. A01N 43/40 |
| 2002/0198399 | A1 | 12/2002 | Onishi |
| 2013/0121919 | A1 | 5/2013 | Feng et al. |
| 2014/0018373 | A1 | 1/2014 | Takyo et al. |
| 2014/0194290 | A1 | 7/2014 | Takahashi et al. |
| 2014/0364444 | A1 | 12/2014 | Takyo et al. |
| 2015/0189880 | A1 | 7/2015 | Maehata et al. |
| 2015/0197532 | A1 | 7/2015 | Takahashi et al. |
| 2015/0336881 | A1 | 11/2015 | Maehata et al. |
| 2015/0336895 | A1 | 11/2015 | Maehata et al. |
| 2016/0009715 | A1 | 1/2016 | Takahashi et al. |
| 2018/0002347 | A1* | 1/2018 | Yonemura ............. C07D 513/04 |
| 2018/0132482 | A1* | 5/2018 | Furuya ................. A01N 37/46 |

FOREIGN PATENT DOCUMENTS

| | | | |
|---|---|---|---|
| JP | 6-321903 | | 11/1994 |
| JP | 2000-516573 | | 12/2000 |
| JP | 2003-34671 | | 2/2003 |
| JP | 2011-63549 | | 3/2011 |
| WO | WO 96/05170 | * | 2/1996 |
| WO | 97/49683 | | 12/1997 |
| WO | 2008/044713 | | 4/2008 |
| WO | 2012/086848 | | 6/2012 |
| WO | 2013/018928 | | 2/2013 |
| WO | 2013/191041 | | 12/2013 |
| WO | 2014/002754 | | 1/2014 |
| WO | 2014/021468 | | 2/2014 |
| WO | 2014/123205 | | 8/2014 |
| WO | 2016/182021 | | 11/2016 |

OTHER PUBLICATIONS

Extended European Search Report dated Jun. 21, 2017 in European Application No. 14861496.9.
Eistert et al., "Conversion of sulfur-containing benzaldehydes with diazomethane", Chemische Berichte, 97(5):1470-1481 (1964), with English Translation.
Ludersdorf et al., "Photoreaktionen sulfinylsubstituierter Carbonsaure-, Thiocarbonsaure- and Selenocarbonsäurederivate in Lösung; lichtinduzierte Säurespaltungen, Heterocyclenbildungen and Photosubstitutionen", Justus Liebigs Annalen der Chemie, 11/12:1992-2017 (1977).
Uchida et al., "The Thermal Decomposition of N,O-Diacyl-N-t-butylhydroxylamines. III. Novel Routes to 2-Substituted 1,2-Benzisothiazol-3-(2H)-ones", Bulletin of the Chemical Society of Japan, 55(4):1183-1187 (1982).
Hellwinkel et al., "Heterocyclic Syntheses via Carbanionically Induced Rearrangement Reactions", Tetrahedron, 39(12):2073-2084 (1983).
Iwao et al., "Ortho-Metalated Aryl tert-Butyl Sulfones. Comparison with Other Directing Groups and New Methodology for Polysubstituted Aromatics", The Journal of Organic Chemistry, 54(1):24-26 (1989).
Wright et al., "Benzyl and t-Butyl Sulfoxides as Sulfenyl Halide Equivalents: A Convenient Preparation of Benzisothiazolones", Tetrahedron Letters, 33(2):153 -156 (1992).
Bonnet et al., "Reaction of magnesiated bases on substituted pyridines: deprotonation or 1,4-addition?", J. Chem. Soc., Perkins Trans. 1, 24:4245-4249 (2000).
Ponci et al., "Preparazione e studio dell'anivita' antifungina di alcune o-n,esiltiobenzamidi", Il Farmaco, Edizione Scientifica, 14:25-31 (1959).
Gialdi et al., "Derivati dialchilaminoalchilici alPazoto o al solfo di 2-mercapto-, 2-ditio-, 2-alchiltio-, 2-aralchiltio- e 2-ariltio-benzanfidi", Il Farmaco, Edizione Scientifica, 16:411-437 (1961).
Ponci et al., "Derivati piridinici dell'acido 2-mercaptobenzoico ad attivita' antifungina", Il Farmaco, Edizione Scientifica, 18:288-300 (1963).
Wagner et al., "Alkali cleavage of 2,4-dioxodihydro-5,6-benzo-1,3-tiazines and 1,3-oxazins and their thioisologes", Die Phanuazie, 24(3):135 -140 (1969), with English Translation.
Xu et al., "Copper-Catalyzed Trifluoromethylthiolation of Aryl Halides with Diverse Directing Groups", Organic Letters, 16(15):3942-3945 (2014).
Schrøder et al., "The identification of AF38469: An orally bioavailable inhibitor of the VPS10P family sorting receptor Sortilin", Bioorganic & Medicinal Chemistry Letters, 24(1):177-180 (2014).
International Search Report dated Feb. 17, 2015 in International Application No. PCT/JP2014/079879.
William L. Jorgensen, et al., "Benzisothiazolones as modulators of macrophage migration inhibitory factor", Bioorganic & Medicinal Chemistry Letters, vol. 21, Issue 15, 2011, pp. 4545-4549.
Th. Zincke, et al., "Über 1.2-Amino-phenylmercaptan", Berichte der Deutschen Chemischen Gesellschaft, vol. 48, 1915, pp. 1242-1254.
International Preliminary Report on Patentability dated May 17, 2016 in International Application No. PCT/JP2014/079879.
Ping Du, et al. "Five- and six-membered N-H...S hydrogen bonding in aromatic amides", Tetrahedron Letters, vol. 50, pp. 320-324, 2009.
Yusuke Nakashima et al., "Optically Active Seleninamides: Isolation, Absolute Configuration, and Racemization Mechanism", J. Org. Chem., vol. 70, No. 3, pp. 868-873, 2005.
Ming Bao, et al., "Reactions of N-sulfenyl-1, 2-benzisothiazolin-3-ones with nucleophiles", Tetrahedron, vol. 60, pp. 11359-11366, 2004.

* cited by examiner

AMIDE COMPOUND OR SALT THEREOF, AGRICULTURAL AND HORTICULTURAL INSECTICIDE AND MICROBICIDE COMPRISING THE COMPOUND, AND METHOD FOR USING THE INSECTICIDE AND MICROBICIDE

This application is a divisional of application Ser. No. 15/035,252, which is the National Stage of International Application No. PCT/JP2014/079879, filed Nov. 11, 2014.

TECHNICAL FIELD

The present invention relates to an agricultural and horticultural insecticide and microbicide comprising a certain kind of amide compound or a salt thereof as an active ingredient, and a method for using the insecticide and microbicide.

BACKGROUND ART

Various compounds have been examined for their potential as agricultural and horticultural insecticides, and among them, certain kinds of amide compounds have been reported to be useful as insecticides (for example, see Patent Literature 1 to 3). None of these references disclose any amide compound composed of a substituted pyridyl amino compound.

CITATION LIST

Patent Literature

Patent Literature 1: JP-A 06-321903
Patent Literature 2: JP-W 2000-516573
Patent Literature 3: JP-A 2011-063549

SUMMARY OF INVENTION

Technical Problem

In crop production in the fields of agriculture, horticulture and the like, the damage caused by pests, diseases, etc. is still immense, and pests and diseases resistant to existing pesticides have emerged. Under such circumstances, the development of novel agricultural and horticultural insecticides and microbicides is desired.

Solution to Problem

The present inventors conducted extensive examination to solve the above-described problems. As a result, the present inventors found that an amide compound represented by the general formula (I) or a salt thereof is highly effective for the control of agricultural and horticultural pests and diseases, and reached the completion of the present invention.

That is, the present invention relates to the following.
[1] An amide compound represented by the formula:

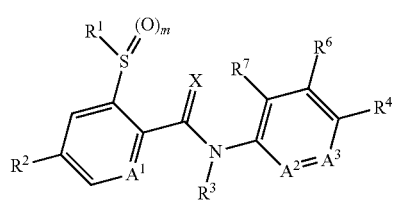

(I)

{wherein $R^1$ represents
(a1) a $(C_1-C_6)$ alkyl group;
(a2) a $(C_2-C_6)$ alkenyl group;
(a3) a $(C_2-C_6)$ alkynyl group;
(a4) a $(C_3-C_6)$ cycloalkyl $(C_1-C_6)$ alkyl group;
(a5) a halo $(C_1-C_6)$ alkyl group;
(a6) a halo $(C_2-C_6)$ alkenyl group;
(a7) a halo $(C_2-C_6)$ alkynyl group; or
(a8) a halo $(C_3-C_6)$ cycloalkyl $(C_1-C_6)$ alkyl group,
$R^2$ and $R^4$ may be the same or different, and each represent
(b1) a halogen atom;
(b2) a cyano group;
(b3) a nitro group;
(b4) a $(C_1-C_6)$ alkyl group;
(b5) a halo $(C_1-C_6)$ alkyl group;
(b6) a $(C_3-C_6)$ cycloalkyl group;
(b7) a halo $(C_3-C_6)$ cycloalkyl group;
(b8) a $(C_1-C_6)$ alkoxy group;
(b9) a halo $(C_1-C_6)$ alkoxy group;
(b10) a $(C_1-C_6)$ alkylthio group;
(b11) a $(C_1-C_6)$ alkylsulfinyl group;
(b12) a $(C_1-C_6)$ alkylsulfonyl group;
(b13) a halo $(C_1-C_6)$ alkylthio group;
(b14) a halo $(C_1-C_6)$ alkylsulfinyl group;
(b15) a halo $(C_1-C_6)$ alkylsulfonyl group;
(b16) a $(C_1-C_6)$ alkoxy halo $(C_1-C_6)$ alkyl group;
(b17) a pentafluorothio group;
(b18) a tri-$(C_1-C_6)$ alkylsilyl group (wherein the alkyl groups of the tri-$(C_1-C_6)$ alkyl moiety may be the same or different); or
(b19) a hydrogen atom,
$R^3$ represents
(c1) a hydrogen atom;
(c2) a $(C_1-C_6)$ alkyl group;
(c3) a $(C_3-C_6)$ cycloalkyl group;
(c4) a $(C_1-C_6)$ alkoxy group;
(c5) a halo $(C_1-C_6)$ alkyl group;
(c6) a $(C_3-C_6)$ cycloalkyl $(C_1-C_6)$ alkyl group;
(c7) a $(C_1-C_6)$ alkoxy $(C_1-C_6)$ alkyl group;
(c8) a $(C_1-C_6)$ alkoxycarbonyl group;
(c9) a $(C_1-C_6)$ alkylthio $(C_1-C_6)$ alkyl group;
(c10) a $(C_1-C_6)$ alkylsulfinyl $(C_1-C_6)$ alkyl group;
(c11) a $(C_1-C_6)$ alkylsulfonyl $(C_1-C_6)$ alkyl group;
(c12) a $(C_2-C_6)$ alkenyl group;
(c13) a $(C_2-C_6)$ alkynyl group;
(c14) a cyano $(C_1-C_6)$ alkyl group;
(c15) a $(C_1-C_6)$ alkoxy $(C_1-C_6)$ alkoxy $(C_1-C_6)$ alkyl group;
(c16) a $(C_1-C_6)$ alkylcarbonyl group; or
(c17) a $(C_3-C_6)$ cycloalkyl $(C_1-C_6)$ carbonyl group,
m represents 0, 1 or 2,
$A^1$, $A^2$ and $A^3$ may be the same or different, and each represent a nitrogen atom or a C—$R^5$ group (wherein $R^5$ represents
(d1) a hydrogen atom;
(d2) a halogen atom;
(d3) a $(C_1-C_6)$ alkyl group;
(d4) a $(C_1-C_6)$ alkoxy group;
(d5) a halo $(C_1-C_6)$ alkyl group;
(d6) a halo $(C_1-C_6)$ alkoxy group;
(d7) a $(C_1-C_6)$ alkylthio group;
(d8) a $(C_1-C_6)$ alkylsulfinyl group;
(d9) a $(C_1-C_6)$ alkylsulfonyl group;
(d10) a halo $(C_1-C_6)$ alkylthio group;
(d11) a halo $(C_1-C_6)$ alkylsulfinyl group;
(d12) a halo $(C_1-C_6)$ alkylsulfonyl group; or
(d13) a $(C_1-C_6)$ alkylcarbonyl group), $R^6$ and $R^7$ may be the same or different, and each represent
(e1) a hydrogen atom;
(e2) a halogen atom;
(e3) a cyano group;
(e4) a $(C_1$-$C_6)$ alkyl group;
(e5) a $(C_1$-$C_6)$ alkoxy group;
(e6) a $(C_1$-$C_6)$ alkylthio group;
(e7) a $(C_1$-$C_6)$ alkylsulfinyl group;
(e8) a $(C_1$-$C_6)$ alkylsulfonyl group;
(e9) a $(C_2$-$C_6)$ alkenyl group;
(e10) a $(C_2$-$C_6)$ alkynyl group;
(e11) a $(C_3$-$C_6)$ cycloalkyl group; or
(e12) a tri-$(C_1$-$C_6)$ alkylsilyl $(C_2$-$C_6)$ alkynyl group (wherein the alkyl groups of the tri-$(C_1$-$C_6)$ alkyl moiety may be the same or different), and
X is an oxygen atom or a sulfur atom}, and
a salt thereof.

[2] The amide compound and the salt according to the above [1], wherein
$R^1$ represents (a1) a $(C_1$-$C_6)$ alkyl group,
$R^2$ and $R^4$ may be the same or different, and each represent
(b1) a halogen atom;
(b4) a $(C_1$-$C_6)$ alkyl group;
(b5) a halo $(C_1$-$C_6)$ alkyl group;
(b8) a $(C_1$-$C_6)$ alkoxy group;
(b9) a halo $(C_1$-$C_6)$ alkoxy group;
(b10) a $(C_1$-$C_6)$ alkylthio group;
(b12) a $(C_1$-$C_6)$ alkylsulfonyl group;
(b13) a halo $(C_1$-$C_6)$ alkylthio group;
(b16) a $(C_1$-$C_6)$ alkoxy halo $(C_1$-$C_6)$ alkyl group;
(b18) a tri-$(C_1$-$C_6)$ alkylsilyl group (wherein the alkyl groups of the tri-$(C_1$-$C_6)$ alkyl moiety may be the same or different); or
(b19) a hydrogen atom,
$R^3$ represents
(c1) a hydrogen atom;
(c2) a $(C_1$-$C_6)$ alkyl group;
(c3) a $(C_3$-$C_6)$ cycloalkyl group;
(c4) a $(C_1$-$C_6)$ alkoxy group;
(c7) a $(C_1$-$C_6)$ alkoxy $(C_1$-$C_6)$ alkyl group;
(c8) a $(C_1$-$C_6)$ alkoxycarbonyl group;
(c9) a $(C_1$-$C_6)$ alkylthio $(C_1$-$C_6)$ alkyl group;
(c10) a $(C_1$-$C_6)$ alkylsulfinyl $(C_1$-$C_6)$ alkyl group;
(c12) a $(C_2$-$C_6)$ alkenyl group;
(c14) a cyano $(C_1$-$C_6)$ alkyl group; or
(c15) a $(C_1$-$C_6)$ alkoxy $(C_1$-$C_6)$ alkoxy $(C_1$-$C_6)$ alkyl group,
m represents 0, 1 or 2,
$A^1$, $A^2$ and $A^3$ may be the same or different, and each represent a nitrogen atom or a C—$R^5$ group (wherein $R^5$ represents
(d1) a hydrogen atom;
(d2) a halogen atom;
(d3) a $(C_1$-$C_6)$ alkyl group;
(d5) a halo $(C_1$-$C_6)$ alkyl group; or
(d7) a $(C_1$-$C_6)$ alkylthio group),
$R^6$ and $R^7$ may be the same or different, and each represent
(e1) a hydrogen atom;
(e2) a halogen atom;
(e3) a cyano group;
(e4) a $(C_1$-$C_6)$ alkyl group;
(e5) a $(C_1$-$C_6)$ alkoxy group;
(e6) a $(C_1$-$C_6)$ alkylthio group; or
(e7) a $(C_1$-$C_6)$ alkylsulfinyl group, and
X is an oxygen atom or a sulfur atom.

[3] The amide compound and the salt according to the above [1], wherein
$R^1$ represents (a1) a $(C_1$-$C_6)$ alkyl group,
$R^2$ and $R^4$ may be the same or different, and each represent
(b1) a halogen atom;
(b5) a halo $(C_1$-$C_6)$ alkyl group;
(b8) a $(C_1$-$C_6)$ alkoxy group;
(b9) a halo $(C_1$-$C_6)$ alkoxy group;
(b10) a $(C_1$-$C_6)$ alkylthio group;
(b12) a $(C_1$-$C_6)$ alkylsulfonyl group;
(b13) a halo $(C_1$-$C_6)$ alkylthio group;
(b16) a $(C_1$-$C_6)$ alkoxy halo $(C_1$-$C_6)$ alkyl group;
(b18) a tri-$(C_1$-$C_6)$ alkylsilyl group (wherein the alkyl groups of the tri-$(C_1$-$C_6)$ alkyl moiety may be the same or different); or
(b19) a hydrogen atom,
$R^3$ represents
(c1) a hydrogen atom;
(c2) a $(C_1$-$C_6)$ alkyl group;
(c3) a $(C_3$-$C_6)$ cycloalkyl group;
(c7) a $(C_1$-$C_6)$ alkoxy $(C_1$-$C_6)$ alkyl group;
(c8) a $(C_1$-$C_6)$ alkoxycarbonyl group;
(c9) a $(C_1$-$C_6)$ alkylthio $(C_1$-$C_6)$ alkyl group;
(c10) a $(C_1$-$C_6)$ alkylsulfinyl $(C_1$-$C_6)$ alkyl group;
(c12) a $(C_2$-$C_6)$ alkenyl group;
(c14) a cyano $(C_1$-$C_6)$ alkyl group; or
(c15) a $(C_1$-$C_6)$ alkoxy $(C_1$-$C_6)$ alkoxy $(C_1$-$C_6)$ alkyl group,
m represents 0, 1 or 2,
$A^1$, $A^2$ and $A^3$ may be the same or different, and each represent a nitrogen atom or a C—$R^5$ group (wherein $R^5$ represents
(d1) a hydrogen atom;
(d2) a halogen atom;
(d3) a $(C_1$-$C_6)$ alkyl group;
(d5) a halo $(C_1$-$C_6)$ alkyl group; or
(d7) a $(C_1$-$C_6)$ alkylthio group),
$R^6$ and $R^7$ may be the same or different, and each represent
(e1) a hydrogen atom;
(e2) a halogen atom;
(e4) a $(C_1$-$C_6)$ alkyl group;
(e5) a $(C_1$-$C_6)$ alkoxy group; or
(e6) a $(C_1$-$C_6)$ alkylthio group, and
X is an oxygen atom or a sulfur atom.

[4] The amide compound and the salt according to any of the above [1] to [3], wherein $A^2$ is a nitrogen atom and $A^3$ is CH.

[5] The amide compound and the salt according to any of the above [1] to [3], wherein $A^2$ and $A^3$ are nitrogen atoms.

[6] The amide compound and the salt according to any of the above [1] to [3], wherein $A^2$ and $A^3$ are CH groups.

[7] Use of the amide compound or the salt according to any of the above [1] to [6] as an agricultural and horticultural insecticide.

[8] A method for using an agricultural and horticultural insecticide, the method comprising applying an active ingredient of the agricultural and horticultural insecticide specified in the above [7] to plants or soil.

[9] A method for controlling an agricultural and horticultural insect pest, comprising applying an effective amount of the agricultural and horticultural insecticide specified in the above [7] to plants or soil.

[10] An ectoparasite control agent comprising the amide compound or the salt according to any of the above [1] to [6] as an active ingredient.

[11] A method for controlling an ectoparasite, comprising bringing an ectoparasite into contact with an effective amount of the ectoparasite control agent according to the above [10].

[12] An endoparasite control agent comprising the amide compound or the salt according to any of the above [1] to [6] as an active ingredient.

[13] A method for controlling an endoparasite, comprising applying, to an endoparasite, an effective amount of the endoparasite control agent according to the above [12].

[14] The amide compound and the salt according to the above [1], wherein $R^1$ represents (a1) a ($C_1$-$C_6$) alkyl group, $R^2$ and $R^4$ may be the same or different, and each represent (b5) a halo ($C_1$-$C_6$) alkyl group, $R^3$ represents (c1) a hydrogen atom, m represents 0, 1 or 2, $A^1$, $A^2$ and $A^3$ each represent a C—$R^5$ group (wherein $R^5$ represents (d1) a hydrogen atom), $R^6$ and $R^7$ may be the same or different, and each represent (e1) a hydrogen atom, (e2) a halogen atom or (e4) a ($C_1$-$C_6$) alkyl group, and X represents an oxygen atom.

[15] The amide compound and the salt according to the above [14], wherein $R^7$ represents a chlorine atom, a bromine atom or an iodine atom.

[16] Use of the amide compound or the salt according to any of the above [1] to [6], [14] and [15] as an agricultural and horticultural microbicide.

[17] A method for using an agricultural and horticultural microbicide, the method comprising applying an active ingredient of the agricultural and horticultural microbicide specified in the above [16] to plants or soil.

[18] A method for controlling an agricultural and horticultural disease, comprising applying an effective amount of the agricultural and horticultural microbicide specified in the above [17] to plants or soil.

[19] The method according to the above [18], wherein the agricultural and horticultural disease is powdery mildew.

[20] An agricultural and horticultural microbicide comprising the amide compound or the salt according to any of the above [1] to [6], [14] and [15].

Advantageous Effects of Invention

The amide compound of the present invention or a salt thereof is not only highly effective as an agricultural and horticultural insecticide and microbicide, but also is effective against pests which live on the exterior of or in the interior of pets such as dogs and cats and domestic animals such as cattle and sheep.

DESCRIPTION OF EMBODIMENTS

In the definitions of the general formula (I) representing the amide compound of the present invention or a salt thereof, "halo" refers to a "halogen atom" and represents a chlorine atom, a bromine atom, an iodine atom or a fluorine atom.

The "($C_1$-$C_6$) alkyl group" refers to a straight-chain or branched-chain alkyl group of 1 to 6 carbon atoms, for example, a methyl group, an ethyl group, a n-propyl group, an isopropyl group, a n-butyl group, an isobutyl group, a sec-butyl group, a tert-butyl group, a n-pentyl group, an isopentyl group, a tert-pentyl group, a neopentyl group, a 2,3-dimethylpropyl group, a 1-ethylpropyl group, a 1-methylbutyl group, a 2-methylbutyl group, a n-hexyl group, an isohexyl group, a 2-hexyl group, a 3-hexyl group, a 2-methylpentyl group, a 3-methylpentyl group, a 1,1,2-trimethyl propyl group, a 3,3-dimethylbutyl group or the like. The "($C_2$-$C_6$) alkenyl group" refers to a straight-chain or branched-chain alkenyl group of 2 to 6 carbon atoms, for example, a vinyl group, an allyl group, an isopropenyl group, a 1-butenyl group, a 2-butenyl group, a 2-methyl-2-propenyl group, a 1-methyl-2-propenyl group, a 2-methyl-1-propenyl group, a pentenyl group, a 1-hexenyl group, a 3,3-dimethyl-1-butenyl group or the like. The "($C_2$-$C_6$) alkynyl group" refers to a straight-chain or branched-chain alkynyl group of 2 to 6 carbon atoms, for example, an ethynyl group, a 1-propynyl group, a 2-propynyl group, a 1-butynyl group, a 2-butynyl group, a 3-butynyl group, a 3-methyl-1-propynyl group, a 2-methyl-3-propynyl group, a pentynyl group, a 1-hexynyl group, a 3-methyl-1-butynyl group, a 3,3-dimethyl-1-butynyl group or the like.

The "($C_3$-$C_6$) cycloalkyl group" refers to a cyclic alkyl group of 3 to 6 carbon atoms, for example, a cyclopropyl group, a cyclobutyl group, a cyclopentyl group, a cyclohexyl group or the like. The "($C_1$-$C_6$) alkoxy group" refers to a straight-chain or branched-chain alkoxy group of 1 to 6 carbon atoms, for example, a methoxy group, an ethoxy group, a n-propoxy group, an isopropoxy group, a n-butoxy group, a sec-butoxy group, a tert-butoxy group, a n-pentyloxy group, an isopentyloxy group, a tert-pentyloxy group, a neopentyloxy group, a 2,3-dimethylpropyloxy group, a 1-ethylpropyloxy group, a 1-methylbutyloxy group, a n-hexyloxy group, an isohexyloxy group, a 1,1,2-trimethyl propyloxy group or the like.

The "($C_1$-$C_6$) alkylthio group" refers to a straight-chain or branched-chain alkylthio group of 1 to 6 carbon atoms, for example, a methylthio group, an ethylthio group, a n-propylthio group, an isopropylthio group, a n-butylthio group, a sec-butylthio group, a tert-butylthio group, a n-pentylthio group, an isopentylthio group, a tert-pentylthio group, a neopentylthio group, a 2,3-dimethylpropylthio group, a 1-ethylpropylthio group, a 1-methylbutylthio group, a n-hexylthio group, an isohexylthio group, a 1,1,2-trimethylpropylthio group or the like. The "($C_1$-$C_6$) alkylsulfinyl group" refers to a straight-chain or branched-chain alkylsulfinyl group of 1 to 6 carbon atoms, for example, a methylsulfinyl group, an ethylsulfinyl group, a n-propylsulfinyl group, an isopropylsulfinyl group, a n-butylsulfinyl group, a sec-butylsulfinyl group, a tert-butylsulfinyl group, a n-pentylsulfinyl group, an isopentylsulfinyl group, a tert-pentylsulfinyl group, a neopentylsulfinyl group, a 2,3-dimethylpropylsulfinyl group, a 1-ethylpropylsulfinyl group, a 1-methylbutylsulfinyl group, a n-hexylsulfinyl group, an isohexylsulfinyl group, a 1,1,2-trimethylpropylsulfinyl group or the like. The "($C_1$-$C_6$) alkylsulfonyl group" refers to a straight-chain or branched-chain alkylsulfonyl group of 1 to 6 carbon atoms, for example, a methylsulfonyl group, an ethylsulfonyl group, a n-propylsulfonyl group, an isopropylsulfonyl group, a n-butylsulfonyl group, a sec-butylsulfonyl group, a tert-butylsulfonyl group, a n-pentylsulfonyl group, an isopentylsulfonyl group, a tert-pentylsulfonyl group, a neopentylsulfonyl group, a 2,3-dimethylpropylsulfonyl group, a 1-ethylpropylsulfonyl group, a 1-methylbutylsulfonyl group, a n-hexylsulfonyl group, an isohexylsulfonyl group, a 1,1,2-trimethylpropylsulfonyl group or the like.

The above-mentioned "($C_1$-$C_6$) alkyl group", "($C_2$-$C_6$) alkenyl group", "($C_2$-$C_6$) alkynyl group", "($C_3$-$C_6$) cycloalkyl group", "($C_1$-$C_6$) alkoxy group", "($C_1$-$C_6$) alkylthio group", "($C_1$-$C_6$) alkylsulfinyl group", "($C_1$-$C_6$) alkylsulfonyl group", "($C_3$-$C_6$) cycloalkyl group" or "($C_1$-$C_6$) alkoxy group" may be substituted with one or more halogen atoms at a substitutable position(s) in place of a hydrogen atom(s), and in the case where the above-listed group is substituted with two or more halogen atoms, the halogen atoms may be the same or different.

The above-mentioned "substituting group substituted with one or more halogen atoms at a substitutable position (s)" is expressed as a "halo ($C_1$-$C_6$) alkyl group", a "halo ($C_2$-$C_6$) alkenyl group", a "halo ($C_2$-$C_6$) alkynyl group", a "halo ($C_3$-$C_6$) cycloalkyl group", a "halo ($C_1$-$C_6$) alkoxy group", a "halo ($C_2$-$C_6$) alkenyloxy group", a "halo ($C_2$-$C_6$) alkynyloxy group", a "halo ($C_1$-$C_6$) alkylthio group", a "halo ($C_1$-$C_6$) alkylsulfinyl group", a "halo ($C_1$-$C_6$) alkylsulfonyl group", a "halo ($C_2$-$C_6$) alkenylthio group", a "halo ($C_2$-$C_6$) alkynylthio group", a "halo ($C_2$-$C_6$) alkenylsulfinyl group", a "halo ($C_2$-$C_6$) alkynylsulfinyl group", a "halo ($C_2$-$C_6$) alkenylsulfonyl group", a "halo ($C_2$-$C_6$) alkynylsulfonyl group", a "halo ($C_3$-$C_6$) cycloalkyl group", a "halo ($C_1$-$C_6$) alkoxy group", a "halo ($C_2$-$C_6$) alkenyloxy group", a "halo ($C_2$-$C_6$) alkynyloxy group", a "halo ($C_3$-$C_6$) cycloalkylthio group", a "halo ($C_3$-$C_6$) cycloalkylsulfinyl group" or a "halo ($C_3$-$C_6$) cycloalkylsulfonyl group".

The expressions "($C_1$-$C_6$) ",", ($C_2$-$C_6$) ",", ($C_3$-$C_6$) ", etc. each refer to the range of the number of carbon atoms in the substituting groups. The same definition holds true for the groups coupled to the above-mentioned substituting groups, and for example, the" ($C_1$-$C_6$) alkoxy halo ($C_1$-$C_6$) alkyl group" means that a straight-chain or branched-chain alkoxy group of 1 to 6 carbon atoms is bound to a straight-chain or branched-chain haloalkyl group of 1 to 6 carbon atoms.

Examples of the salt of the amide compound represented by the general formula (I) of the present invention include inorganic acid salts, such as hydrochlorides, sulfates, nitrates and phosphates; organic acid salts, such as acetates, fumarates, maleates, oxalates, methanesulfonates, benzenesulfonates and p-toluenesulfonates; and salts with an inorganic or organic base such as a sodium ion, a potassium ion, a calcium ion and a trimethylammonium ion.

The amide compound represented by the general formula (I) of the present invention and a salt thereof can have one or more chiral centers in the structural formula, and can exist as two or more kinds of optical isomers or diastereomers. All the optical isomers and mixtures of the isomers at any ratio are also included in the present invention. Further, the compound represented by the general formula (I) of the present invention and a salt thereof can exist as two kinds of geometric isomers due to a carbon-carbon double bond in the structural formula. All the geometric isomers and mixtures of the isomers at any ratio are also included in the present invention.

In preferable embodiments for use as an insecticide, the amide compound represented by the general formula (I) of the present invention or a salt thereof is the one in which $R^1$ is (a1) a ($C_1$-$C_6$) alkyl group, $R^2$ and $R^4$ may be the same or different, and are each preferably (b5) a halo ($C_1$-$C_6$) alkyl group;

(b9) a halo ($C_1$-$C_6$) alkoxy group;

(b13) a halo ($C_1$-$C_6$) alkylthio group; or (b16) a ($C_1$-$C_6$) alkoxy halo ($C_1$-$C_6$) alkyl group, $R^3$ is preferably (c1) a hydrogen atom;

(c2) a ($C_1$-$C_6$) alkyl group; or (c3) a ($C_3$-$C_6$) cycloalkyl group, $A^1$, $A^2$ and $A^3$ may be the same or different, and are each preferably a nitrogen atom or a C—$R^5$ group (wherein $R^5$ represents (d1) a hydrogen atom;

(d2) a halogen atom; or (d3) a ($C_1$-$C_6$) alkyl group;

(d5) a halo ($C_1$-$C_6$) alkyl group; or (d7) a ($C_1$-$C_6$) alkylthio group), and X is preferably an oxygen atom.

In preferable embodiments for use as a microbicide, the amide compound represented by the general formula (I) of the present invention or a salt thereof is the one in which $R^1$ is (a1) a ($C_1$-$C_6$) alkyl group, $R^2$ and $R^4$ may be the same or different, and are each (b5) a halo ($C_1$-$C_6$) alkyl group, $R^3$ is (c1) a hydrogen atom, m is 0, 1 or 2, $A^1$, $A^2$ and $A^3$ each represent a C—$R^5$ group (wherein $R^5$ represents (d1) a hydrogen atom), $R^6$ and $R^7$ may be the same or different, and are each (e1) a hydrogen atom;

(e2) a halogen atom; or (e4) a ($C_1$-$C_6$) alkyl group, and

X is an oxygen atom.

In particularly preferable embodiments, $R^1$ is (a1) a ($C_1$-$C_6$) alkyl group, $R^2$ and $R^4$ may be the same or different, and are each (b5) a halo ($C_1$-$C_6$) alkyl group, $R^3$ is (c1) a hydrogen atom, m is 0, 1 or 2, $A^1$, $A^2$ and $A^3$ each represent a C—$R^5$ group (wherein $R^5$ represents (d1) a hydrogen atom), $R^6$ and $R^7$ may be the same or different, and are each (e1) a hydrogen atom, a chlorine atom, a bromine atom or an iodine atom, and X is an oxygen atom.

The amide compound represented by the general formula (I) of the present invention or a salt thereof can be produced according to, for example, the production method described below, but the present invention is not limited thereto.

Production Method 1

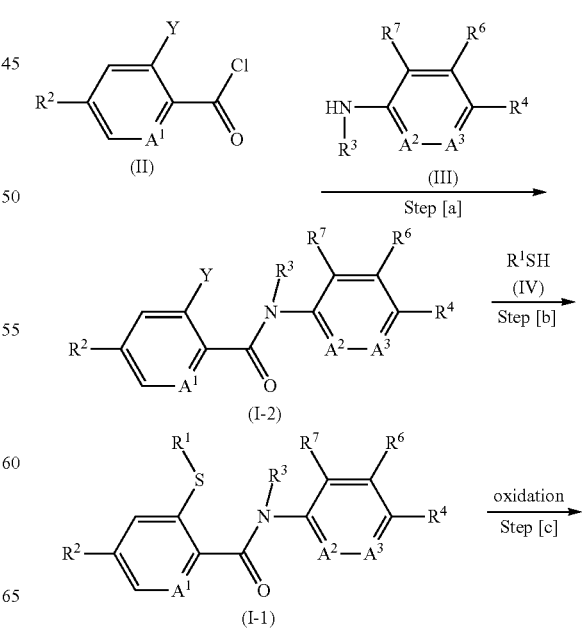

-continued

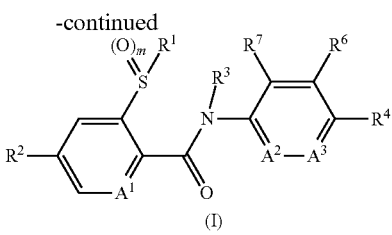

(In the formulae, $R^1$, $R^2$, $R^3$, $R^4$, $A^1$, $A^2$, $A^3$ and m are as defined above, and Y represents a halogen atom.)

Production Method at Step [a]

The amide compound represented by the general formula (I-2) can be produced by allowing the carboxylic chloride represented by the general formula (II) to react with the amine compound represented by the general formula (III) in the presence of a base and an inert solvent. Since this reaction is an equimolar reaction of the reactants, they are basically used in equimolar amounts, but it is possible that any of the reactants is used in an excess amount.

The base used in this reaction may be an inorganic base or an organic base. Examples of the inorganic base include alkali metal hydroxides such as sodium hydroxide and potassium hydroxide; alkali metal hydrides such as sodium hydride and potassium hydride; alkali metal alkoxides such as sodium ethoxide and potassium t-butoxide; and carbonates such as sodium carbonate, potassium carbonate and sodium hydrogen carbonate. Examples of the organic base include triethylamine, pyridine and DBU. The amount of the base used is an equimolar or excess molar amount relative to the carboxylic chloride represented by the general formula (II).

The inert solvent used in this reaction may be any solvent unless it markedly inhibits the progress of the reaction, and the examples include aromatic hydrocarbons such as benzene, toluene and xylene; halogenated aliphatic hydrocarbons such as methylene chloride, chloroform and carbon tetrachloride; halogenated aromatic hydrocarbons such as chlorobenzene and dichlorobenzene; straight-chain or cyclic ethers such as diethyl ether, dioxane and tetrahydrofuran; esters such as ethyl acetate; amides such as dimethylformamide and dimethylacetamide; and others such as dimethyl sulfoxide, 1,3-dimethyl-2-imidazolidinone, acetone and methyl ethyl ketone. These inert solvents may be used alone or as a mixture of two or more kinds.

This reaction may be conducted under the atmosphere of an inert gas such as nitrogen gas and argon gas. The reaction temperature is in the range of room temperature (for example, 20° C.) to the boiling point of the inert solvent used. The reaction time varies with the reaction scale and the reaction temperature, but is basically in the range of a few minutes to 48 hours. After the reaction is completed, the compound of interest is isolated from the post-reaction mixture by a usual method. As needed, the compound of interest can be purified by recrystallization, column chromatography, etc. Alternatively, the isolated product may be subjected to the next step without purification.

Production Method at Step [b]

The amide compound represented by the general formula (I-1) can be produced by allowing the amide compound represented by the general formula (I-2) to react with the thiol compound represented by the general formula (IV) in the presence of a base in an inert solvent.

Since this reaction is an equimolar reaction of the compounds, they are basically used in equimolar amounts, but it is possible that any of the compounds is used in an excess amount.

Examples of the base that can be used in this reaction include inorganic basic salts such as sodium hydroxide, potassium hydroxide, sodium carbonate, potassium carbonate, cesium carbonate, sodium hydrogen carbonate and potassium hydrogen carbonate; alkali metal hydrides such as sodium hydride and potassium hydride; and alkoxides such as sodium methoxide, sodium ethoxide and potassium tert-butoxide. The amount of the base used is usually in the range of about 1- to 5-fold molar equivalents relative to the amide compound represented by the general formula (I-2). Commercially available products of sodium methanethiolate or sodium ethanethiolate can also be used as the base, and in this case, compound (IV) does not have to be used.

The inert solvent that can be used in this reaction may be any solvent unless it markedly inhibits the reaction, and the examples include alcohols such as methanol, ethanol, propanol, butanol and 2-propanol; straight-chain or cyclic ethers such as diethyl ether, tetrahydrofuran and dioxane; aromatic hydrocarbons such as benzene, toluene and xylene; halogenated aliphatic hydrocarbons such as methylene chloride, chloroform and carbon tetrachloride; halogenated aromatic hydrocarbons such as chlorobenzene and dichlorobenzene; nitriles such as acetonitrile; esters such as ethyl acetate; and polar solvents such as N,N-dimethylformamide, N,N-dimethylacetamide, dimethyl sulfoxide and 1,3-dimethyl-2-imidazolidinone. These inert solvents may be used alone or as a mixture of two or more kinds.

This reaction may be conducted under the atmosphere of an inert gas such as nitrogen gas and argon gas. The reaction temperature in this reaction is usually in the range of about 0° C. to the boiling point of the solvent used. The reaction time varies with the reaction scale, the reaction temperature and the like, but is basically selected as appropriate from the range of a few minutes to 48 hours. After the reaction is completed, the compound of interest is isolated from the post-reaction mixture by a usual method. As needed, the compound of interest can be purified by recrystallization, column chromatography, etc. Alternatively, the isolated product may be subjected to the next step without purification.

Production Method at Step [c]

The amide compound represented by the general formula (I) can be produced by allowing the amide compound represented by the general formula (I-1) to react with an oxidizing agent in an inert solvent. Examples of the oxidizing agent used in this reaction include peroxides such as a hydrogen peroxide solution, perbenzoic acid and m-chloroperoxybenzoic acid. The amount of the oxidizing agent used is appropriately selected from the range of 0.8- to 5-fold molar equivalents relative to the amide compound represented by the general formula (I-1), and is preferably in the range of 1- to 2-fold molar equivalents.

The inert solvent that can be used in this reaction may be any solvent unless it markedly inhibits the reaction, and the examples include straight-chain or cyclic ethers such as diethyl ether, tetrahydrofuran and dioxane; aromatic hydrocarbons such as benzene, toluene and xylene; halogenated aliphatic hydrocarbons such as methylene chloride, chloroform and carbon tetrachloride; halogenated aromatic hydrocarbons such as chlorobenzene and dichlorobenzene; nitriles such as acetonitrile; esters such as ethyl acetate; organic acids such as formic acid and acetic acid; and polar solvents such as N,N-dimethylformamide, N,N-dimethylacetamide, 1,3-dimethyl-2-imidazolidinone and water. These inert solvents may be used alone or as a mixture of two or more kinds.

The reaction temperature in this reaction is appropriately selected from the range of −10° C. to the reflux temperature of the inert solvent used. The reaction time varies with the reaction scale, the reaction temperature and the like and is not the same in every case, but is basically selected as appropriate from the range of a few minutes to 48 hours. After the reaction is completed, the compound of interest is isolated from the post-reaction mixture by a usual method. As needed, the compound of interest can be purified by recrystallization, column chromatography, etc.

The starting material or the intermediates of the present invention can be produced according to, for example, the following methods.

Production Method of Intermediate (III)

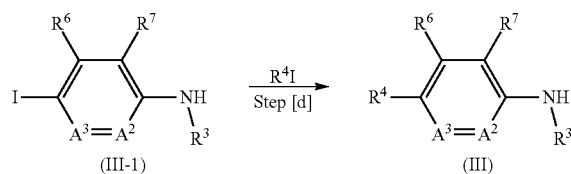

(In the formula, $R^2$, $R^3$, $R^4$, $A^2$ and $A^3$ are as defined above.)

Production Method at Step [d]

The compound represented by the general formula (III) can be produced from the corresponding iodinated compound (III-1) according to the method described in JP-A 11-302233 or WO 2013/018928.

Production Method of Intermediate (II-1)

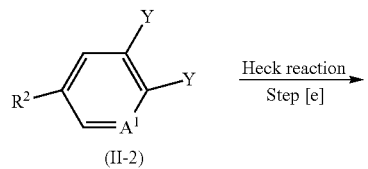

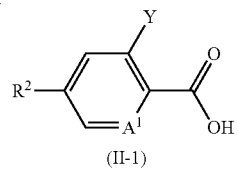

(In the formula, $R^2$ and $A^1$ are as defined above.)

Production Method at Step [e]

The compound represented by the general formula (II-1) can be synthesized from the corresponding halogenated compound (II-2) according to the method described in JP-A 2005-272338. The compound (II-1) can be derived into the carboxylic chloride (II) according to the usual method.

Next, specific examples of the compound of the present invention are shown below. In the following tables (Tables 1 to 6 and 10 to 12), Me stands for a methyl group, Et stands for an ethyl group, n-Pr stands for a n-propyl group, i-Pr stands for an isopropyl group, c-Pr stands for a cyclopropyl group, and i-Bu stands for an isobutyl group. TMS stands for a trimethylsilyl group. Shown in the column of "Physical property" is a melting point (° C.), a refractive index $n_D$ (measurement temperature; ° C.), "NMR" or "Amorphous". NMR data are shown in different tables (Tables 7 to 9).

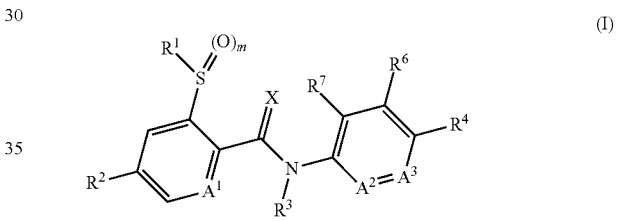

TABLE 1

| Compound No. | $R^1$ | $R^2$ | $R^3$ | $R^4$ | $A^1$ | $A^2$ | $A^3$ | m | Physical property |
|---|---|---|---|---|---|---|---|---|---|
| 1-1 | Et | $CF_3$ | Me | $CF_3$ | CH | N | CH | 0 | NMR |
| 1-2 | Et | $CF_3$ | Me | $CF_3$ | CH | N | CH | 1 | NMR |
| 1-3 | Et | $CF_3$ | Me | $CF_3$ | CH | N | CH | 2 | NMR |
| 1-4 | Et | $CF_3$ | Et | $CF_3$ | CH | N | CH | 0 | 1.5204(21.3) |
| 1-5 | Et | $CF_3$ | Et | $CF_3$ | CH | N | CH | 1 | 1.5539(19.1) |
| 1-6 | Et | $CF_3$ | Et | $CF_3$ | CH | N | CH | 2 | 1.5570(18.9) |
| 1-7 | Et | $CF_3$ | c-Pr | $CF_3$ | CH | N | CH | 0 | 1.5209(21.9) |
| 1-8 | Et | $CF_3$ | c-Pr | $CF_3$ | CH | N | CH | 1 | 1.5165(19.2) |
| 1-9 | Et | $CF_3$ | c-Pr | $CF_3$ | CH | N | CH | 2 | NMR |
| 1-10 | Et | $CF_3$ | Et | $CF_3$ | N | N | CH | 0 | 1.5212(19.8) |
| 1-11 | Et | $CF_3$ | Et | $CF_3$ | N | N | CH | 1 | |
| 1-12 | Et | $CF_3$ | Et | $CF_3$ | N | N | CH | 2 | 1.5030(19.8) |
| 1-13 | Et | $CF_3$ | c-Pr | $CF_3$ | N | N | CH | 0 | 1.5224(17.2) |
| 1-14 | Et | $CF_3$ | c-Pr | $CF_3$ | N | N | CH | 1 | NMR |
| 1-15 | Et | $CF_3$ | c-Pr | $CF_3$ | N | N | CH | 2 | 127.3-123.7 |
| 1-16 | Et | $CF_3$ | Me | $CF_3$ | N | N | CH | 0 | 61-63 |
| 1-17 | Et | $CF_3$ | Me | $CF_3$ | N | N | CH | 1 | 89-92 |
| 1-18 | Et | $CF_3$ | Me | $CF_3$ | N | N | CH | 2 | 97-99 |
| 1-19 | Et | $i-C_3F_7$ | Me | $CF_3$ | CH | N | CH | 0 | |
| 1-20 | Et | $CF_3$ | Me | $i-C_3F_7$ | CH | N | CH | 0 | NMR |
| 1-21 | Et | $CF_3$ | Me | $i-C_3F_7$ | CH | N | CH | 2 | NMR |
| 1-22 | Et | $CF_3$ | Me | $i-C_3F_7$ | CH | CH | N | 0 | NMR |
| 1-23 | Et | $CF_3$ | Me | $i-C_3F_7$ | CH | CH | N | 1 | NMR |
| 1-24 | Et | $CF_3$ | Me | $i-C_3F_7$ | CH | CH | N | 2 | NMR |
| 1-25 | Et | $CF_3$ | Me | $C_2F_5$ | CH | N | CH | 0 | NMR |
| 1-26 | Et | $CF_3$ | Me | $C_2F_5$ | CH | N | CH | 2 | NMR |
| 1-27 | Me | $CF_3$ | Me | $CF_3$ | CH | N | CH | 0 | |

TABLE 1-continued

| Compound No. | R¹ | R² | R³ | R⁴ | A¹ | A² | A³ | m | Physical property |
|---|---|---|---|---|---|---|---|---|---|
| 1-28 | Me | $CF_3$ | Me | $CF_3$ | CH | N | CH | 1 | |
| 1-29 | Me | $CF_3$ | Me | $CF_3$ | CH | N | CH | 2 | |
| 1-30 | n-Pr | $CF_3$ | Me | $CF_3$ | CH | N | CH | 0 | |
| 1-31 | n-Pr | $CF_3$ | Me | $CF_3$ | CH | N | CH | 1 | |
| 1-32 | n-Pr | $CF_3$ | Me | $CF_3$ | CH | N | CH | 2 | |
| 1-33 | i-Pr | $CF_3$ | Me | $CF_3$ | CH | N | CH | 0 | |
| 1-34 | i-Pr | $CF_3$ | Me | $CF_3$ | CH | N | CH | 1 | |
| 1-35 | i-Pr | $CF_3$ | Me | $CF_3$ | CH | N | CH | 2 | |
| 1-36 | Et | $CF_3$ | Me | Cl | CH | N | CH | 0 | 1.5500(24.5) |
| 1-37 | Et | $CF_3$ | Me | Cl | CH | N | CH | 1 | 1.5430(26.8) |
| 1-38 | Et | $CF_3$ | Me | Cl | CH | N | CH | 2 | 1.5182(26.8) |
| 1-39 | Et | $CF_3$ | OMe | $CF_3$ | CH | N | CH | 0 | |
| 1-40 | Et | $CF_3$ | OMe | $CF_3$ | CH | N | CH | 1 | |
| 1-41 | Et | $CF_3$ | OMe | $CF_3$ | CH | N | CH | 2 | |
| 1-42 | Et | $C_2F_5$ | Me | $CF_3$ | CH | N | CH | 0 | NMR |
| 1-43 | Et | $C_2F_5$ | Me | $CF_3$ | CH | N | CH | 1 | NMR |
| 1-44 | Et | $C_2F_5$ | Me | $CF_3$ | CH | N | CH | 2 | NMR |
| 1-45 | Et | $CF_3$ | $CH_2OMe$ | $C_2F_5$ | CH | N | CH | 0 | NMR |
| 1-46 | Et | $CF_3$ | $CH_2OMe$ | $C_2F_5$ | CH | N | CH | 2 | NMR |

$R^6$ and $R^7$ each represent a hydrogen atom, and X represents an oxygen atom.

$R^6$ and $R^7$ each represent a hydrogen atom, and X represents an oxygen atom.

$R^6$ and $R^7$ each represent a hydrogen atom, and X represents an oxygen atom.

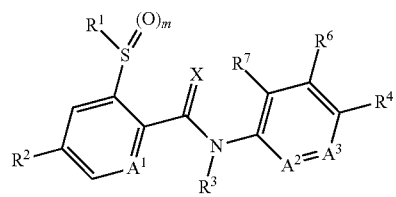

(I)

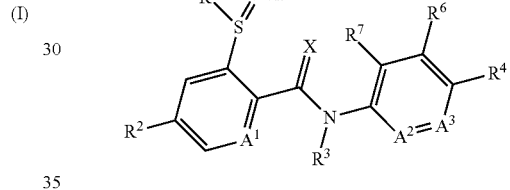

(I)

TABLE 2

| Compound No. | R¹ | R² | R³ | R⁴ | A¹ | A² | A³ | m | Physical property |
|---|---|---|---|---|---|---|---|---|---|
| 2-1 | Et | $CF_3$ | Me | $CF_3$ | CH | N | N | 0 | NMR |
| 2-2 | Et | $CF_3$ | Me | $CF_3$ | CH | N | N | 1 | NMR |
| 2-3 | Et | $CF_3$ | Me | $CF_3$ | CH | N | N | 2 | NMR |
| 2-4 | Et | $CF_2CF_3$ | Me | $CF_3$ | CH | N | N | 0 | 1.498 (26.5) |
| 2-5 | Et | $CF_2CF_3$ | Me | $CF_3$ | CH | N | N | 1 | |
| 2-6 | Et | $CF_2CF_3$ | Me | $CF_3$ | CH | N | N | 2 | 1.489 (33.0) |
| 2-7 | Et | $CF_2CF_2CF_3$ | Me | $CF_3$ | CH | N | N | 0 | |
| 2-8 | Et | $CF_2CF_2CF_3$ | Me | $CF_3$ | CH | N | N | 1 | |
| 2-9 | Et | $CF_2CF_2CF_3$ | Me | $CF_3$ | CH | N | N | 2 | |
| 2-10 | Et | $CF_2CF_2CF_2CF_3$ | Me | $CF_3$ | CH | N | N | 0 | 1.472 (20.9) |
| 2-11 | Et | $CF_2CF_2CF_2CF_3$ | Me | $CF_3$ | CH | N | N | 1 | |
| 2-12 | Et | $CF_2CF_2CF_2CF_3$ | Me | $CF_3$ | CH | N | N | 2 | 104-105 |
| 2-13 | Et | Br | Me | $CF_3$ | CH | N | N | 0 | 98-100 |
| 2-14 | Et | Br | Me | $CF_3$ | CH | N | N | 1 | 45-50 |
| 2-15 | Et | Br | Me | $CF_3$ | CH | N | N | 2 | 143-145 |
| 2-16 | Et | S—t-Bu | Me | $CF_3$ | CH | N | N | 0 | 1.524 (21.0) |
| 2-17 | Et | S—t-Bu | Me | $CF_3$ | CH | N | N | 1 | |
| 2-18 | Et | S—t-Bu | Me | $CF_3$ | CH | N | N | 2 | |
| 2-19 | Et | $SO_2$—t-Bu | Me | $CF_3$ | CH | N | N | 0 | |
| 2-20 | Et | $SO_2$—t-Bu | Me | $CF_3$ | CH | N | N | 1 | |
| 2-21 | Et | $SO_2$—t-Bu | Me | $CF_3$ | CH | N | N | 2 | 180-182 |

TABLE 3

| Compound No. | $R^1$ | $R^2$ | $R^3$ | $R^4$ | $A^1$ | $A^2$ | $A^3$ | m | Physical property |
|---|---|---|---|---|---|---|---|---|---|
| 3-1 | Et | $CF_3$ | Me | $CF_3$ | CH | CH | CH | 0 | 1.5021 (20.1) |
| 3-2 | Et | $CF_3$ | Me | $CF_3$ | CH | CH | CH | 1 | Amorphous |
| 3-3 | Et | $CF_3$ | Me | $CF_3$ | CH | CH | CH | 2 | NMR |
| 3-4 | Et | $CF_3$ | Me | $C(CF_3)_2OMe$ | CH | CH | CH | 0 | 1.5042 (25.0) |
| 3-5 | Et | $CF_3$ | Me | $C(CF_3)_2OMe$ | CH | CH | CH | 1 | |
| 3-6 | Et | $CF_3$ | Me | $C(CF_3)_2OMe$ | CH | CH | CH | 2 | 1.5081 (29.5) |
| 3-7 | Et | $CF_3$ | Me | $i-C_3F_7$ | CH | CH | CH | 0 | Amorphous |
| 3-8 | Et | $CF_3$ | Me | $i-C_3F_7$ | CH | CH | CH | 1 | Amorphous |
| 3-9 | Et | $CF_3$ | Me | $i-C_3F_7$ | CH | CH | CH | 2 | Amorphous |
| 3-10 | Et | $CF_3$ | Me | $CH(CF_3)_2$ | CH | CH | CH | 0 | Amorphous |
| 3-11 | Et | $CF_3$ | Me | $CH(CF_3)_2$ | CH | CH | CH | 2 | Amorphous |
| 3-12 | Et | $CF_3$ | Me | $OCF_3$ | CH | CH | CH | 0 | 1.5090 (26.0) |
| 3-13 | Et | $CF_3$ | Me | $OCF_3$ | CH | CH | CH | 1 | 1.5060 (24.0) |
| 3-14 | Et | $CF_3$ | Me | $OCF_3$ | CH | CH | CH | 2 | 1.4932 (24.0) |
| 3-15 | Et | $CF_3$ | Me | $SCF_3$ | CH | CH | CH | 0 | 1.5239 (26.2) |
| 3-16 | Et | $CF_3$ | Me | $SCF_3$ | CH | CH | CH | 1 | 1.5269 (24.4) |
| 3-17 | Et | $CF_3$ | Me | $SCF_3$ | CH | CH | CH | 2 | 1.5175 (24.3) |
| 3-18 | Et | $CF_3$ | Me | $i-C_3H_7$ | CH | CH | CH | 0 | 1.5400 (24.5) |
| 3-19 | Et | $CF_3$ | Me | $i-C_3H_7$ | CH | CH | CH | 1 | 1.5380 (26.9) |
| 3-20 | Et | $CF_3$ | Me | $i-C_3H_7$ | CH | CH | CH | 2 | 1.5158 (26.8) |
| 3-21 | Et | $CF_3$ | Me | Cl | CH | CH | CH | 0 | NMR |
| 3-22 | Et | $CF_3$ | Me | Cl | CH | CH | CH | 1 | |
| 3-23 | Et | $CF_3$ | Me | Cl | CH | CH | CH | 2 | |
| 3-24 | Et | $CF_3$ | Me | H | CH | CH | CCl | 0 | NMR |
| 3-25 | Et | $CF_3$ | Me | H | CH | CH | CCl | 1 | |
| 3-26 | Et | $CF_3$ | Me | H | CH | CH | CCl | 2 | |
| 3-27 | Et | $CF_3$ | Me | Cl | CH | CH | CCl | 0 | 1.5560 (26.3) |
| 3-28 | Et | $CF_3$ | Me | Cl | CH | CH | CCl | 1 | 1.5406 (29.1) |
| 3-29 | Et | $CF_3$ | Me | Cl | CH | CH | CCl | 2 | 130-137 |
| 3-30 | Et | $CF_3$ | Me | Cl | CH | CH | $CCF_3$ | 0 | 1.5160 (24.2) |
| 3-31 | Et | $CF_3$ | Me | Cl | CH | CH | $CCF_3$ | 1 | 1.5132 (29.0) |
| 3-32 | Et | $CF_3$ | Me | Cl | CH | CH | $CCF_3$ | 2 | 145-151 |
| 3-33 | Et | $CF_3$ | Me | I | CH | CF | CH | 0 | 1.5566 (24.1) |
| 3-34 | Et | $CF_3$ | Me | I | CH | CF | CH | 1 | 1.5571 (31.5) |
| 3-35 | Et | $CF_3$ | Me | I | CH | CF | CH | 2 | 1.5490 (26.7) |
| 3-36 | Et | $CF_3$ | Me | F | CH | CH | $CCF_3$ | 0 | 1.5050 (21.7) |
| 3-37 | Et | $CF_3$ | Me | F | CH | CH | $CCF_3$ | 1 | 1.4949 (23.8) |
| 3-38 | Et | $CF_3$ | Me | F | CH | CH | $CCF_3$ | 2 | 1.4770 (23.2) |
| 3-39 | Et | $CF_3$ | Me | $OCF_3$ | CH | CH | CCl | 0 | 1.5178 (23.0) |
| 3-40 | Et | $CF_3$ | Me | $OCF_3$ | CH | CH | CCl | 1 | 1.5150 (29.6) |
| 3-41 | Et | $CF_3$ | Me | $OCF_3$ | CH | CH | CCl | 2 | 1.4981 (24.3) |
| 3-42 | Et | $CF_3$ | Me | $SCF_3$ | CH | $CCH_3$ | CH | 0 | 1.5272 (26.2) |
| 3-43 | Et | $CF_3$ | Me | $SCF_3$ | CH | $CCH_3$ | CH | 1 | 1.5146 (31.8) |
| 3-44 | Et | $CF_3$ | Me | $SCF_3$ | CH | $CCH_3$ | CH | 2 | 1.4968 (28.5) |
| 3-45 | Et | $CF_3$ | Me | $CF_2CF_3$ | CH | CH | $CCH_3$ | 0 | 1.5029 (21.7) |
| 3-46 | Et | $CF_3$ | Me | $CF_2CF_3$ | CH | CH | $CCH_3$ | 1 | |
| 3-47 | Et | $CF_3$ | Me | $CF_2CF_3$ | CH | CH | $CCH_3$ | 2 | 1.4916 (40.1) |
| 3-48 | Et | $CF_3$ | Me | $CF_2CF_3$ | CH | $CCH_3$ | $CCH_3$ | 0 | 1.4581 (29.3) |
| 3-49 | Et | $CF_3$ | Me | $CF_2CF_3$ | CH | $CCH_3$ | $CCH_3$ | 1 | |
| 3-50 | Et | $CF_3$ | Me | $CF_2CF_3$ | CH | $CCH_3$ | $CCH_3$ | 2 | |
| 3-51 | Et | $CF_3$ | Me | $i-C_3F_7$ | CH | CH | $CCH_3$ | 0 | 1.4819 (22.1) |
| 3-52 | Et | $CF_3$ | Me | $i-C_3F_7$ | CH | CH | $CCH_3$ | 1 | 1.4784 (35.0) |
| 3-53 | Et | $CF_3$ | Me | $i-C_3F_7$ | CH | CH | $CCH_3$ | 2 | 1.4570 (36.8) |
| 3-54 | Et | $CF_3$ | Me | $CF_2CF_3$ | CH | CF | CH | 0 | 1.4762 (25.3) |
| 3-55 | Et | $CF_3$ | Me | $CF_2CF_3$ | CH | CF | CH | 1 | |
| 3-56 | Et | $CF_3$ | Me | $CF_2CF_3$ | CH | CF | CH | 2 | |
| 3-57 | Et | $CF_3$ | Me | $i-C_3F_7$ | CH | CCl | CH | 0 | NMR |
| 3-58 | Et | $CF_3$ | Me | $i-C_3F_7$ | CH | CCl | CH | 1 | |
| 3-59 | Et | $CF_3$ | Me | $i-C_3F_7$ | CH | CCl | CH | 2 | |
| 3-60 | Et | $CF_3$ | $CO_2Et$ | $SCF_3$ | CH | CH | CH | 0 | 1.526 (22.3) |
| 3-61 | Et | $CF_3$ | $CO_2Et$ | $SCF_3$ | CH | CH | CH | 1 | |
| 3-62 | Et | $CF_3$ | $CO_2Et$ | $SCF_3$ | CH | CH | CH | 2 | 175-176 |
| 3-63 | Et | $CF_3$ | $CH_2SOMe$ | $SCF_3$ | CH | CH | CH | 0 | 1.526 (26.1) |
| 3-64 | Et | $CF_3$ | $CH_2SOMe$ | $SCF_3$ | CH | CH | CH | 1 | |
| 3-65 | Et | $CF_3$ | $CH_2SOMe$ | $SCF_3$ | CH | CH | CH | 2 | |
| 3-66 | Et | $CF_3$ | $CH_2OCH_2CH_2OMe$ | $SCF_3$ | CH | CH | CH | 0 | 1.517 (23.2) |
| 3-67 | Et | $CF_3$ | $CH_2OCH_2CH_2OMe$ | $SCF_3$ | CH | CH | CH | 1 | 1.519 (23.1) |
| 3-68 | Et | $CF_3$ | $CH_2OCH_2CH_2OMe$ | $SCF_3$ | CH | CH | CH | 2 | 1.499 (23.1) |
| 3-69 | Et | $CF_3$ | $CH_2CN$ | $SCF_3$ | CH | CH | CH | 0 | 1.518 (23.2) |
| 3-70 | Et | $CF_3$ | $CH_2CN$ | $SCF_3$ | CH | CH | CH | 1 | |
| 3-71 | Et | $CF_3$ | $CH_2CN$ | $SCF_3$ | CH | CH | CH | 2 | |
| 3-72 | Et | $CF_3$ | $CH_2CH=CH_2$ | $SCF_3$ | CH | CH | CH | 0 | 1.522 (23.1) |
| 3-73 | Et | $CF_3$ | $CH_2CH=CH_2$ | $SCF_3$ | CH | CH | CH | 1 | |
| 3-74 | Et | $CF_3$ | $CH_2CH=CH_2$ | $SCF_3$ | CH | CH | CH | 2 | |
| 3-75 | Et | $CF_3$ | $CH_2SMe$ | $SCF_3$ | CH | CH | CH | 0 | 1.5425 (23.2) |
| 3-76 | Et | $CF_3$ | $CH_2SMe$ | $SCF_3$ | CH | CH | CH | 1 | |
| 3-77 | Et | $CF_3$ | $CH_2SMe$ | $SCF_3$ | CH | CH | CH | 2 | |

TABLE 3-continued

| Compound No. | R¹ | R² | R³ | R⁴ | A¹ | A² | A³ | m | Physical property |
|---|---|---|---|---|---|---|---|---|---|
| 3-78 | Et | OCF₃ | Me | SCF₃ | CH | CH | CH | 0 | 1.535 (19.6) |
| 3-79 | Et | OCF₃ | Me | SCF₃ | CH | CH | CH | 1 | 1.481 (20.7) |
| 3-80 | Et | OCF₃ | Me | SCF₃ | CH | CH | CH | 2 | 1.506 (20.7) |
| 3-81 | Et | SCF₃ | Me | SCF₃ | CH | CH | CH | 0 | 1.543 (21.2) |
| 3-82 | Et | SCF₃ | Me | SCF₃ | CH | CH | CH | 1 | 1.544 (26.2) |
| 3-83 | Et | SCF₃ | Me | SCF₃ | CH | CH | CH | 2 | 1.526 (25.2) |
| 3-84 | Et | CF₃ | CH₂OMe | SCF₃ | CH | CH | CH | 0 | 71-74 |
| 3-85 | Et | CF₃ | CH₂OMe | SCF₃ | CH | CH | CH | 1 | 1.524 (25.9) |
| 3-86 | Et | CF₃ | CH₂OMe | SCF₃ | CH | CH | CH | 2 | 105-106 |
| 3-87 | Et | CF₃ | Me | SOCF₃ | CH | CH | CH | 2 | 1.494 (23.3) |
| 3-88 | Et | CF₃ | Me | SO₂CF₃ | CH | CH | CH | 2 | 108-110 |

$R^6$ and $R^7$ each represent a hydrogen atom, and X represents an oxygen atom.
$R^6$ and $R^7$ each represent a hydrogen atom, and X represents an oxygen atom.
$R^6$ and $R^7$ each represent a hydrogen atom, and X represents an oxygen atom.
$R^6$ and $R^7$ each represent a hydrogen atom, and X represents an oxygen atom.
$R^6$ and $R^7$ each represent a hydrogen atom, and X represents an oxygen atom.
$R^6$ and $R^7$ each represent a hydrogen atom, and X represents an oxygen atom.

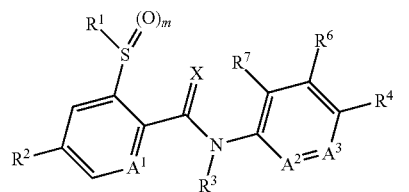

(I)

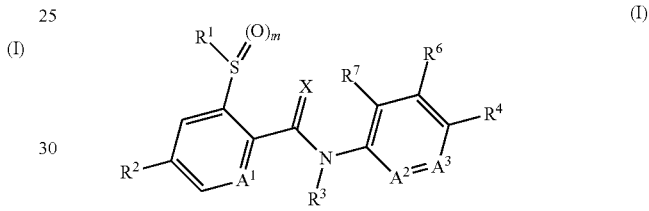

(I)

TABLE 4

| Compound No. | R¹ | R² | R³ | R⁴ | A¹ | A² | A³ | m | Physical property |
|---|---|---|---|---|---|---|---|---|---|
| 4-1 | Et | CF₃ | H | C(CF₃)₂OMe | CH | CSEt | CH | 0 | 1.5365 (20.2) |
| 4-2 | Et | CF₃ | H | i-C₃F₇ | CH | CF | CH | 0 | NMR |
| 4-3 | Et | CF₃ | H | i-C₃F₇ | CH | CH | CH | 0 | 92-94 |
| 4-4 | Et | CF₃ | H | n-C₄F₉ | CH | CMe | CH | 0 | 117-118 |
| 4-5 | Et | CF₃ | H | CH(CF₃)₂ | CH | CH | CH | 0 | 112-115 |
| 4-6 | Et | CF₃ | H | C(CF₃)₂OMe | CH | CH | CH | 0 | NMR |
| 4-7 | Et | CF₃ | H | i-C₃F₇ | CH | CF | CH | 1 | 165-167 |
| 4-8 | Et | CF₃ | H | i-C₃F₇ | CH | CF | CH | 2 | 198-199 |
| 4-9 | Et | CF₃ | H | CH(CF₃)₂ | CH | CH | CH | 1 | 145-147 |
| 4-10 | Et | CF₃ | H | CH(CF₃)₂ | CH | CH | CH | 2 | 156-160 |
| 4-11 | Et | CF₃ | H | C(CF₃)₂OMe | CH | CH | CH | 1 | 192-194 |
| 4-12 | Et | CF₃ | H | C(CF₃)₂OMe | CH | CH | CH | 2 | 158-160 |
| 4-13 | Et | CF₃ | H | i-C₃F₇ | CH | CH | CH | 1 | 200-202 |
| 4-14 | Et | CF₃ | H | i-C₃F₇ | CH | CH | CH | 2 | 171-172 |
| 4-15 | Et | CF₃ | H | n-C₄F₉ | CH | CMe | CH | 1 | 108-110 |
| 4-16 | Et | CF₃ | H | n-C₄F₉ | CH | CMe | CH | 2 | 120-122 |
| 4-17 | Et | CF₃ | H | Cl | CH | CH | CCl | 0 | 153-155 |
| 4-18 | Et | CF₃ | H | Cl | CH | CH | CCF₃ | 0 | 112-115 |
| 4-19 | Et | CF₃ | H | I | CH | CF | CH | 0 | 153-157 |
| 4-20 | Et | CF₃ | H | F | CH | CF | CCF₃ | 0 | 125-128 |
| 4-21 | Et | CF₃ | H | F | CH | CF | CCF₃ | 1 | 192-195 |
| 4-22 | Et | CF₃ | H | F | CH | CF | CCF₃ | 2 | 160-164 |
| 4-23 | Et | CF₃ | H | i-C₃F₇ | CH | CMe | CH | 0 | 81-83 |
| 4-24 | Et | CF₃ | H | i-C₃F₇ | CH | CMe | CH | 1 | |
| 4-25 | Et | CF₃ | H | i-C₃F₇ | CH | CMe | CH | 2 | 196-198 |
| 4-26 | Et | CF₃ | H | i-C₃F₇ | CH | CCl | CH | 0 | 1.5058 (24.3) |
| 4-27 | Et | CF₃ | H | i-C₃F₇ | CH | CCl | CH | 1 | 139-142 |
| 4-28 | Et | CF₃ | H | i-C₃F₇ | CH | CCl | CH | 2 | 155-157 |

TABLE 5

| Compound No. | $R^1$ | $R^2$ | $R^4$ | $A^2$ | $A^3$ | $R^6$ | $R^7$ | m | Physical property |
|---|---|---|---|---|---|---|---|---|---|
| 5-1 | Et | $CF_3$ | i-$C_3F_7$ | CH | CH | H | Et | 0 | 100-103 |
| 5-2 | Et | $CF_3$ | i-$C_3F_7$ | CH | CH | H | Et | 1 | 128-130 |
| 5-3 | Et | $CF_3$ | i-$C_3F_7$ | CH | CH | H | Et | 2 | 131-133 |
| 5-4 | Et | $CF_3$ | i-$C_3F_7$ | CH | CH | H | n-Pr | 0 | |
| 5-5 | Et | $CF_3$ | i-$C_3F_7$ | CH | CH | H | n-Pr | 1 | |
| 5-6 | Et | $CF_3$ | i-$C_3F_7$ | CH | CH | H | n-Pr | 2 | |
| 5-7 | Et | $CF_3$ | i-$C_3F_7$ | CH | CH | H | i-Pr | 0 | 90-91 |
| 5-8 | Et | $CF_3$ | i-$C_3F_7$ | CH | CH | H | i-Pr | 1 | 84-86 |
| 5-9 | Et | $CF_3$ | i-$C_3F_7$ | CH | CH | H | i-Pr | 2 | 144-145 |
| 5-10 | Et | $CF_3$ | i-$C_3F_7$ | CH | CH | H | OMe | 0 | 69-71 |
| 5-11 | Et | $CF_3$ | i-$C_3F_7$ | CH | CH | H | OMe | 1 | 215-217 |
| 5-12 | Et | $CF_3$ | i-$C_3F_7$ | CH | CH | H | OMe | 2 | 250-255 |
| 5-13 | Et | $CF_3$ | i-$C_3F_7$ | CH | CH | H | SMe | 0 | 62-64 |
| 5-14 | Et | $CF_3$ | i-$C_3F_7$ | CH | CH | H | SMe | 1 | |
| 5-15 | Et | $CF_3$ | i-$C_3F_7$ | CH | CH | H | SMe | 2 | |
| 5-16 | Et | $CF_3$ | i-$C_3F_7$ | CH | CH | H | Br | 0 | 1.515 (18.0) |
| 5-17 | Et | $CF_3$ | i-$C_3F_7$ | CH | CH | H | Br | 1 | 110-112 |
| 5-18 | Et | $CF_3$ | i-$C_3F_7$ | CH | CH | H | Br | 2 | 140-142 |
| 5-19 | Et | $CF_3$ | i-$C_3F_7$ | CH | CH | H | I | 0 | 92-93 |
| 5-20 | Et | $CF_3$ | i-$C_3F_7$ | CH | CH | H | I | 1 | 120-122 |
| 5-21 | Et | $CF_3$ | i-$C_3F_7$ | CH | CH | H | I | 2 | 167-168 |
| 5-22 | Et | $CF_3$ | i-$C_3F_7$ | CH | CH | H | CN | 0 | 1.513 (21.0) |
| 5-23 | Et | $CF_3$ | i-$C_3F_7$ | CH | CH | H | CN | 1 | 68-70 |
| 5-24 | Et | $CF_3$ | i-$C_3F_7$ | CH | CH | H | CN | 2 | 84-86 |
| 5-25 | Et | $CF_3$ | i-$C_3F_7$ | CH | CH | H | F | 1 | 165-167 |
| 5-26 | Et | $CF_3$ | i-$C_3F_7$ | CH | CH | H | F | 2 | 198-199 |
| 5-27 | Et | $CF_3$ | i-$C_3F_7$ | CH | CH | Me | Me | 0 | 86-88 |
| 5-28 | Et | $CF_3$ | i-$C_3F_7$ | CH | CH | Me | Me | 1 | 157-160 |
| 5-29 | Et | $CF_3$ | i-$C_3F_7$ | CH | CH | Me | Me | 2 | 170-172 |
| 5-30 | Et | $CF_3$ | i-$C_3F_7$ | CH | CMe | H | Me | 0 | 128-130 |
| 5-31 | Et | $CF_3$ | i-$C_3F_7$ | CH | CMe | H | Me | 1 | 193-197 |
| 5-32 | Et | $CF_3$ | i-$C_3F_7$ | CH | CMe | H | Me | 2 | 183-187 |
| 5-33 | Et | $CF_3$ | i-$C_3F_7$ | CMe | CH | H | Me | 0 | 192-193 |
| 5-34 | Et | $CF_3$ | i-$C_3F_7$ | CMe | CH | H | Me | 1 | 194-196 |
| 5-35 | Et | $CF_3$ | i-$C_3F_7$ | CMe | CH | H | Me | 2 | 208-210 |
| 5-36 | Et | $CF_3$ | i-$C_3F_7$ | CH | CH | Cl | Me | 0 | 1.502 (22.3) |
| 5-37 | Et | $CF_3$ | i-$C_3F_7$ | CH | CH | Cl | Me | 1 | 210-212 |
| 5-38 | Et | $CF_3$ | i-$C_3F_7$ | CH | CH | Cl | Me | 2 | 194-196 |
| 5-39 | Et | $CF_3$ | i-$C_3F_7$ | CH | CCl | H | Me | 0 | 122-125 |
| 5-40 | Et | $CF_3$ | i-$C_3F_7$ | CH | CCl | H | Me | 1 | |
| 5-41 | Et | $CF_3$ | i-$C_3F_7$ | CH | CCl | H | Me | 2 | |
| 5-42 | Et | $CF_3$ | i-$C_3F_7$ | CCl | CH | H | Me | 0 | 110-112 |
| 5-43 | Et | $CF_3$ | i-$C_3F_7$ | CCl | CH | H | Me | 1 | 175-177 |
| 5-44 | Et | $CF_3$ | i-$C_3F_7$ | CCl | CH | H | Me | 2 | 185-187 |
| 5-45 | Et | $CF_3$ | i-$C_3F_7$ | CH | CH | H | SOMe | 0 | |
| 5-46 | Et | $CF_3$ | i-$C_3F_7$ | CH | CH | H | SOMe | 1 | |
| 5-47 | Et | $CF_3$ | i-$C_3F_7$ | CH | CH | H | SOMe | 2 | |
| 5-48 | Et | $CF_3$ | i-$C_3F_7$ | CH | CH | F | Me | 0 | 1.473 (28.9) |
| 5-49 | Et | $CF_3$ | i-$C_3F_7$ | CH | CH | F | Me | 1 | NMR |
| 5-50 | Et | $CF_3$ | i-$C_3F_7$ | CH | CH | F | Me | 2 | 156-158 |
| 5-51 | Et | $CF_3$ | $CF(CF_3)(CHF_2)$ | CH | CH | H | Cl | 0 | NMR |
| 5-52 | Et | $CF_3$ | $CF(CF_3)(CHF_2)$ | CH | CH | H | Cl | 1 | |
| 5-53 | Et | $CF_3$ | $CF(CF_3)(CHF_2)$ | CH | CH | H | Cl | 2 | |
| 5-54 | Et | $CF_3$ | $CF(CF_3)(CHF_2)$ | CH | CH | H | H | 0 | NMR |
| 5-55 | Et | $CF_3$ | $CF(CF_3)(CHF_2)$ | CH | CH | H | H | 1 | |
| 5-56 | Et | $CF_3$ | $CF(CF_3)(CHF_2)$ | CH | CH | H | H | 2 | |
| 5-57 | Et | $CF_3$ | $CF(CF_3)(CBrF_2)$ | CH | CH | H | Cl | 0 | 1.540 (23.4) |
| 5-58 | Et | $CF_3$ | $CF(CF_3)(CBrF_2)$ | CH | CH | H | Cl | 1 | 202-204 |
| 5-59 | Et | $CF_3$ | $CF(CF_3)(CBrF_2)$ | CH | CH | H | Cl | 2 | 175-180 |
| 5-60 | Et | $CF_3$ | $CF(CF_3)(CBrF_2)$ | CH | CH | H | H | 0 | 93-95 |
| 5-61 | Et | $CF_3$ | $CF(CF_3)(CBrF_2)$ | CH | CH | H | H | 1 | |
| 5-62 | Et | $CF_3$ | $CF(CF_3)(CBrF_2)$ | CH | CH | H | H | 2 | |
| 5-63 | Et | $CF_3$ | TMS | CH | CH | H | Me | 0 | 70-72 |
| 5-64 | Et | $CF_3$ | TMS | CH | CH | H | Me | 1 | NMR |
| 5-65 | Et | $CF_3$ | TMS | CH | CH | H | Me | 2 | 160-161 |
| 5-66 | Et | $CF_3$ | $CF_2CF_3$ | CH | CH | H | Cl | 0 | 130-132 |
| 5-67 | Et | $CF_3$ | $CF_2CF_3$ | CH | CH | H | Cl | 1 | 165-166 |
| 5-68 | Et | $CF_3$ | $CF_2CF_3$ | CH | CH | H | Cl | 2 | 168-170 |
| 5-69 | Et | $CF_3$ | $OCF_2CHF_2$ | CH | CH | H | Me | 0 | 147-149 |
| 5-70 | Et | $CF_3$ | $OCF_2CHF_2$ | CH | CH | H | Me | 1 | 1.498 (21.4) |
| 5-71 | Et | $CF_3$ | $OCF_2CHF_2$ | CH | CH | H | Me | 2 | 128-129 |
| 5-72 | Et | $CF_3$ | $OCF_3$ | CH | CH | H | Br | 0 | 109-110 |
| 5-73 | Et | $CF_3$ | $OCF_3$ | CH | CH | H | Br | 1 | 163-165 |
| 5-74 | Et | $CF_3$ | $OCF_3$ | CH | CH | H | Br | 2 | 154-156 |
| 5-75 | Et | $CF_3$ | $OCF_3$ | CH | CH | H | Et | 0 | 151-153 |
| 5-76 | Et | $CF_3$ | $OCF_3$ | CH | CH | H | Et | 1 | |
| 5-77 | Et | $CF_3$ | $OCF_3$ | CH | CH | H | Et | 2 | 153-155 |

TABLE 5-continued

| Compound No. | $R^1$ | $R^2$ | $R^4$ | $A^2$ | $A^3$ | $R^6$ | $R^7$ | m | Physical property |
|---|---|---|---|---|---|---|---|---|---|
| 5-78 | Et | $CF_3$ | $OCF_3$ | CH | CH | H | Cl | 0 | 104-105 |
| 5-79 | Et | $CF_3$ | $OCF_3$ | CH | CH | H | Cl | 1 | 154-156 |
| 5-80 | Et | $CF_3$ | $OCF_3$ | CH | CH | H | Cl | 2 | 142-145 |
| 5-81 | Et | $CF_3$ | $i$-$C_3F_7$ | CH | CH | $OCH_2CH_2CMe_3$ | H | 0 | 129-130 |
| 5-82 | Et | $CF_3$ | $i$-$C_3F_7$ | CH | CH | $OCH_2CH_2CMe_3$ | H | 1 | |
| 5-83 | Et | $CF_3$ | $i$-$C_3F_7$ | CH | CH | $OCH_2CH_2CMe_3$ | H | 2 | |

$A^1$ represents CH, $R^3$ represents a hydrogen atom, and X represents an oxygen atom.
$A^1$ represents CH, $R^3$ represents a hydrogen atom, and X represents an oxygen atom.
$A^1$ represents CH, $R^3$ represents a hydrogen atom, and X represents an oxygen atom.
$A^1$ represents CH, $R^3$ represents a hydrogen atom, and X represents an oxygen atom.

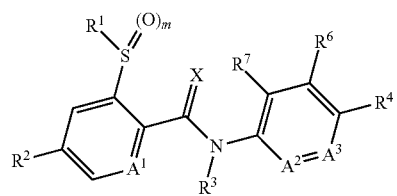

(I)

TABLE 6

| Compound No. | $R^1$ | $R^2$ | $R^4$ | $A^2$ | $A^3$ | $R^6$ | $R^7$ | m | Physical property |
|---|---|---|---|---|---|---|---|---|---|
| 6-1 | Me | $CF_3$ | $i$-$C_3F_7$ | CH | CH | H | Me | 0 | 141-143 |
| 6-2 | Me | $CF_3$ | $i$-$C_3F_7$ | CH | CH | H | Me | 1 | 178-180 |
| 6-3 | Me | $CF_3$ | $i$-$C_3F_7$ | CH | CH | H | Me | 2 | 205-207 |
| 6-4 | i-Pr | $CF_3$ | $i$-$C_3F_7$ | CH | CH | H | Me | 0 | 100-102 |
| 6-5 | i-Pr | $CF_3$ | $i$-$C_3F_7$ | CH | CH | H | Me | 1 | 160-163 |
| 6-6 | i-Pr | $CF_3$ | $i$-$C_3F_7$ | CH | CH | H | Me | 2 | 156-159 |
| 6-7 | Et | Cl | $i$-$C_3F_7$ | CH | CH | H | Me | 0 | 78-82 |
| 6-8 | Et | Cl | $i$-$C_3F_7$ | CH | CH | H | Me | 1 | |
| 6-9 | Et | Cl | $i$-$C_3F_7$ | CH | CH | H | Me | 2 | 156-159 |
| 6-10 | Et | OMe | $i$-$C_3F_7$ | CH | CH | H | Me | 0 | 72-75 |
| 6-11 | Et | OMe | $i$-$C_3F_7$ | CH | CH | H | Me | 1 | |
| 6-12 | Et | OMe | $i$-$C_3F_7$ | CH | CH | H | Me | 2 | 183-185 |
| 6-13 | Me | $CF_3$ | $i$-$C_3F_7$ | CH | CH | H | Cl | 0 | 130-132 |
| 6-14 | Me | $CF_3$ | $i$-$C_3F_7$ | CH | CH | H | Cl | 1 | |
| 6-15 | Me | $CF_3$ | $i$-$C_3F_7$ | CH | CH | H | Cl | 2 | 145-147 |
| 6-16 | i-Pr | $CF_3$ | $i$-$C_3F_7$ | CH | CH | H | Cl | 0 | 1.505 (27.2) |
| 6-17 | i-Pr | $CF_3$ | $i$-$C_3F_7$ | CH | CH | H | Cl | 1 | |
| 6-18 | i-Pr | $CF_3$ | $i$-$C_3F_7$ | CH | CH | H | Cl | 2 | |
| 6-19 | n-Pr | $CF_3$ | $i$-$C_3F_7$ | CH | CH | H | Cl | 0 | 1.506 (20.1) |
| 6-20 | n-Pr | $CF_3$ | $i$-$C_3F_7$ | CH | CH | H | Cl | 1 | 125-126 |
| 6-21 | n-Pr | $CF_3$ | $i$-$C_3F_7$ | CH | CH | H | Cl | 2 | 164-166 |
| 6-22 | Et | $SCF_3$ | $i$-$C_3F_7$ | CH | CH | H | Cl | 0 | 1.528 (24.2) |
| 6-23 | Et | $SCF_3$ | $i$-$C_3F_7$ | CH | CH | H | Cl | 1 | 130-132 |
| 6-24 | Et | $SCF_3$ | $i$-$C_3F_7$ | CH | CH | H | Cl | 2 | 134-136 |

$A^1$ represents CH, $R^3$ represents a hydrogen atom, and X represents an oxygen atom.

TABLE 7

NMR Data 1

| Compound No. | $^1$H-NMR[$CDCl_3$/TMS, δ value (ppm)] |
|---|---|
| 1-1 | 8.21 (s, 1H), 7.75 (s, 1H), 7.67-7.62 (m, 2H), 3.99 (s, 3H), 3.00 (dd, 2H), 1.30 (t, 3H) |
| 1-2 | 8.62 (s, 1H), 8.35 (s, 1H), 7.84 (d, 1H), 7.60 (d, 1H), 7.32 (d, 1H), 7.26 (d, 1H), 3.58 (s, 3H), 3.40-3.30 (m, 1H), 3.05-2.95 (m, 1H), 1.35 (t, 3H) |
| 1-3 | 8.70 (s, 1H), 8.29 (s, 1H), 7.98 (brs, 1H), 7.68 (brs, 2H), 7.37 (brs, 1H), 3.81-2.98 (m, 5H), 1.36 (t, 3H) |
| 1-9 | 8.68 (d, 1H), 8.59 (d, 1H), 8.32 (d, 1H), 7.96 (dd, 1H), 7.57 (d, 1H), 3.44 (m, 1H), 3.62 (m, 1H), 3.01 (m, 1H), 1.35 (t, 3H), 1.14 (m, 1H), 0.98 (m, 1H), 0.88 (m, 1H), 0.59 (m, 1H) |
| 1-14 | 8.74 (brs, 1H), 8.27 (brs, 1H), 7.87 (brs, 1H), 3.50 (q, 2H), 3.23 (brm, 1H), 1.34 (t, 3H), 0.82-0.38 (brm, 4H) |
| 1-20 | 8.64 (s, 1H), 7.90-7.81 (brs, 2H), 7.58 (s, 1H), 7.45 (d, 1H), 7.35 (d, 1H), 3.48 (s, 3H), 3.00 (dd, 2H), 1.32 (t, 3H) |
| 1-21 | 8.67 (brs, 1H), 8.30 (brs, 1H), 8.02-7.48 (brm, 3H), 7.40 (brs, 1H), 3.83-3.22 (brm, 5H), 1.36 (t, 3H) |
| 1-22 | 8.60 (brs, 1H), 7.76 (brs, 1H), 7.60 (brs, 1H), 7.50-7.30 (m, 3H), 3.48 (s, 3H), 2.95 (dd, 2H), 1.29 (t, 3H) |
| 1-23 | 8.56 (brs, 1H), 8.26 (s, 1H), 7.72 (d, 1H), 7.65 (d, 1H), 7.57 (d, 1H), 7.23 (brs, 1H), 3.53 (s, 3H), 3.36-3.26 (m, 1H), 3.06-2.96 (m, 1H), 1.33 (t, 3H) |
| 1-24 | 8.68 (d, 1H), 8.22 (s, 1H), 7.92 (dd, 1H), 7.62 (d, 1H), 7.54 (dd, 1H), 7.17 (d, 1H), 3.65-3.52 (m, 5H), 1.34 (t, 3H) |
| 1-25 | 8.62 (s, 1H), 7.81 (s, 1H), 7.58 (s, 1H), 7.46 (d, 1H), 7.36 (d, 1H), 7.49 (s, 3H), 3.00 (dd, 2H), 1.32 (t, 3H) |

TABLE 7-continued

NMR Data 1

| Compound No. | $^1$H-NMR[CDCl$_3$/TMS, δ value (ppm)] |
|---|---|
| 1-26 | 8.66 (s, 1H), 8.30 (s, 1H), 8.10-7.12 (brm, 4H), 3.82-3.71 (brm, 5H), 1.36 (t, 3H) |
| 1-42 | 8.65 (s, 1H), 7.72 (d, 1H), 7.58-7.46 (m, 2H), 7.40 (d, 1H), 7.37 (d, 1H), 3.49 (s, 3H), 3.00 (dd, 2H), 1.31 (t, 3H) |
| 1-43 | 8.62 (d, 1H), 8.31 (s, 1H), 7.82 (d, 1H), 7.58 (d, 1H), 7.34 (d, 1H), 7.27 (d, 1H), 3.57 (s, 3H), 3.40-3.27 (m, 1H), 3.05-2.92 (m, 1H), 1.33 (t, 3H) |
| 1-44 | 8.70 (s, 1H), 8.25 (s, 1H), 8.10-7.10 (brm, 4H), 3.83-3.22 (brs, 5H), 1.34 (t, 3H) |
| 1-45 | 8.59 (d, 1H), 7.84 (dd, 1H), 7.70 (d, 1H), 7.56 (s, 1H), 7.39 (dd, 2H), 5.35 (s, 2H), 3.39 (s, 3H), 3.00 (dd, 2H), 1.29 (t, 3H) |
| 1-46 | 8.68 (s, 1H), 8.28 (s, 1H), 8.20-7.16 (brm, 4H), 6.00-4.52 (brm, 2H), 3.95-2.75 (brm, 5H), 1.36 (t, 3H) |

TABLE 8

NMR Data 2

| Compound No. | $^1$H-NMR[CDCl$_3$/TMS, δ value (ppm)] |
|---|---|
| 2-1 | 8.40 (d, 1H), 7.78 (d, 1H), 7.63 (s, 1H), 7.54 (d, 1H), 7.45 (d, 1H), 3.60 (s, 3H), 3.03 (dd, 2H), 1.33 (t, 3H) |
| 2-2 | 8.31 (s, H), 8.04 (d, 1H), 7.77 (d, 1H), 7.75 (d, 1H), 7.48 (d, 1H), 7.67 (s, 3H), 3.32-3.21 (m, 1H), 3.10-2.96 (m, 1H), 1.34 (t, 3H) |
| 2-3 | 8.56 (brs, 1H), 8.32 (s, 1H), 8.15-7.46 (brm, 4H), 3.90-3.30 (brm, 5H), 1.36 (t, 3H) |

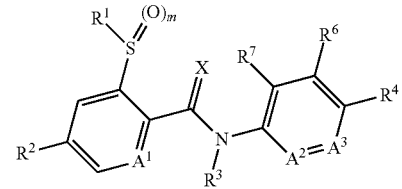

(I)

TABLE 9

NMR Data 3

| Compound No. | $^1$H-NMR[CDCl$_3$/TMS, δ value (ppm)] |
|---|---|
| 3-2 | 8.29 (s, 1H), 7.54 (d, 2H), 7.49 (d, 1H), 7.23 (d, 2H), 7.14 (d, 1H), 3.50 (s, 3H), 3.42-3.31 (m, 1H), 3.03-2.92 (m, 1H), 1.35 (t, 3H) |
| 3-3 | 8.22 (s, 1H), 7.60 (d, 1H), 7.49 (s, 4H), 7.15 (d, 1H), 3.62 (dd, 2H), 3.54 (s, 3H), 1.35 (t, 3H) |
| 3-7 | 8.03 (d, 2H), 7.52 (d, 2H), 7.45-7.33 (m, 3H), 3.95 (s, 3H), 3.00 (dd, 2H), 1.41 (t, 3H) |
| 3-8 | 8.28 (s, 1H), 7.52 (d, 2H), 7.44 (s, 1H), 7.24 (d, 2H), 7.10 (s, 1H), 7.52 (s, 3H), 3.41-3.30 (m, 1H), 3.03-2.92 (m, 1H), 1.34 (t, 3H) |
| 3-9 | 8.21 (s, 1H), 7.55 (d, 1H), 7.47 (s, 4H), 7.10 (d, 1H), 3.65-3.54 (m, 5H), 1.35 (t, 3H) |
| 3-10 | 7.42 (d, 2H), 7.37-7.02 (brm, 5H), 3.98 (brs, 1H), 3.66-3.21 (brs, 3H), 2.96 (dd, 2H), 1.30 (t, 3H) |
| 3-11 | 8.20 (s, 1H), 7.55 (d, 1H), 7.41 (d, 2H), 7.27 (d, 2H), 7.12 (d, 1H), 3.96 (quint., 1H), 3.62 (dd, 2H), 3.55 (s, 3H), 1.35 (t, 3H) |
| 3-21 | 7.41 (brs, 2H), 7.30-7.00 (brm, 5H), 3.47 (s, 3H), 2.98 (dd, 2H), 1.33 (t, 3H) |
| 3-24 | 7.44 (brs, 2H), 7.25-6.91 (brm, 5H), 3.46 (s, 3H), 2.99 (dd, 2H), 1.34 (t, 3H) |
| 3-57 | 7.69-7.55 (m, 2H), 7.48 (d, 1H), 7.39 (brs, 1H), 7.21-7.11 (m, 2H), 3.45 (s, 1H), 3.10-2.98 (m, 2H), 1.36 (t, H) |
| 4-2 | 9.14 (s, 1H), 8.71 (t, 1H), 7.95 (d, 1H), 7.59 (s, 1H), 7.57 (d, 1H), 7.44 (d, 1H), 7.40 (d, 1H), 3.02 (dd, 2H), 1.33 (t, 3H) |
| 4-6 | 8.66 (s, 1H), 7.90 (d, 1H), 7.77 (d, 2H), 7.69 (d, H), 7.60 (d, 1H), 3.50 (s, 3H), 3.01 (dd, 2H), 1.33 (t, 3H) |
| 5-49 | 8.48 (s, 1H), 8.34 (s, 1H), 7.95-7.84 (m, 2H), 7.53 (t, 1H), 3.40-3.30 (m, 1H), 2.97-2.87 (m, 1H), 2.31 (d, 3H), 1.25 (t, 3H) |
| 5-51 | 8.29 (s, 1H), 7.68-7.64 (m, 3H), 7.48 (s, 1H), 7.45-7.40 (m, 1H), 6.29-6.01 (m, 1H), 3.01 (q, 2H), 1.33 (t, 3H) |
| 5-54 | 8.82 (s, 1H), 7.86 (d, 1H), 7.82 (d, 2H), 7.67 (s, 1H), 7.60 (d, 2H), 7.54 (d, 1H), 6.35-6.07 (m, 1H), 3.01 (q, 2H), 1.33 (t, 3H) |
| 5-64 | 8.42 (s, 1H), 8.33 (d, 1H), 7.87 (d, 1H), 7.69 (d, 1H), 7.47 (d, 1H), 7.30-7.26 (m, 2H), 3.25-3.15 (m, 1H), 2.80-2.70 (m, 1H), 2.21 (s, 3H), 1.12 (t, 3H) |

TABLE 10

| Compound No. | $R^1$ | $R^2$ | $R^4$ | $A^2$ | $A^3$ | $R^6$ | $R^7$ | m | Physical property |
|---|---|---|---|---|---|---|---|---|---|
| 7-1 | Et | $CF_3$ | $i\text{-}C_3F_7$ | CH | CH | H | C≡CH | 0 | 78-80 |
| 7-2 | Et | $CF_3$ | $i\text{-}C_3F_7$ | CH | CH | H | C≡CH | 1 | |
| 7-3 | Et | $CF_3$ | $i\text{-}C_3F_7$ | CH | CH | H | C≡CH | 2 | |
| 7-4 | Et | $CF_3$ | $i\text{-}C_3F_7$ | CH | CH | H | C≡CTMS | 0 | 78-80 |
| 7-5 | Et | $CF_3$ | $i\text{-}C_3F_7$ | CH | CH | H | C≡CTMS | 1 | |
| 7-6 | Et | $CF_3$ | $i\text{-}C_3F_7$ | CH | CH | H | C≡CTMS | 2 | |
| 7-7 | Et | $CF_3$ | $i\text{-}C_3F_7$ | CH | CH | H | c-Pr | 0 | 41-43 |
| 7-8 | Et | $CF_3$ | $i\text{-}C_3F_7$ | CH | CH | H | c-Pr | 1 | |
| 7-9 | Et | $CF_3$ | $i\text{-}C_3F_7$ | CH | CH | H | c-Pr | 2 | |
| 7-10 | Et | $CF_3$ | $i\text{-}C_3F_7$ | CF | CH | H | Cl | 0 | |
| 7-11 | Et | $CF_3$ | $i\text{-}C_3F_7$ | CF | CH | H | Cl | 1 | |
| 7-12 | Et | $CF_3$ | $i\text{-}C_3F_7$ | CF | CH | H | Cl | 2 | |

$A^1$ represents CH, $R^3$ represents a hydrogen atom, and X represents an oxygen atom.

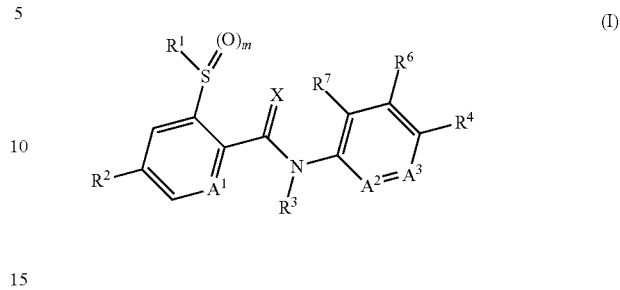

(I)

TABLE 11

| Compound No. | $R^1$ | $R^2$ | $R^3$ | $R^4$ | $A^1$ | $A^2$ | $A^3$ | m | Physical property |
|---|---|---|---|---|---|---|---|---|---|
| 8-1 | Et | $CF_3$ | CO—c-Pr | $CH_2CF_3$ | CH | CCl | CH | 0 | 1.5275 (22.1) |
| 8-2 | Et | $CF_3$ | CO—c-Pr | $CH_2CF_3$ | CH | CCl | CH | 1 | |
| 8-3 | Et | $CF_3$ | CO—c-Pr | $CH_2CF_3$ | CH | CCl | CH | 2 | |
| 8-4 | Et | $CF_3$ | CO—c-Pr | $C(CF_3)_2OMe$ | CH | CCl | CH | 0 | |
| 8-5 | Et | $CF_3$ | CO—c-Pr | $C(CF_3)_2OMe$ | CH | CCl | CH | 1 | |
| 8-6 | Et | $CF_3$ | CO—c-Pr | $C(CF_3)_2OMe$ | CH | CCl | CH | 2 | |
| 8-7 | Et | $CF_3$ | CO—c-Pr | $i\text{-}C_3F_7$ | CH | CCOMe | CH | 0 | |
| 8-8 | Et | $CF_3$ | CO—c-Pr | $i\text{-}C_3F_7$ | CH | CCOMe | CH | 1 | |
| 8-9 | Et | $CF_3$ | CO—c-Pr | $i\text{-}C_3F_7$ | CH | CCOMe | CH | 2 | |
| 8-10 | Et | $CF_3$ | CO—c-Pr | $C(CF_3)_2OMe$ | CH | CMe | CH | 0 | 1.5010 (19.9) |
| 8-11 | Et | $CF_3$ | CO—c-Pr | $C(CF_3)_2OMe$ | CH | CMe | CH | 1 | |
| 8-12 | Et | $CF_3$ | CO—c-Pr | $C(CF_3)_2OMe$ | CH | CMe | CH | 2 | |
| 8-13 | Et | $CF_3$ | CO—c-Pr | $C(CF_3)_2OEt$ | CH | CMe | CH | 0 | 1.5015 (20.0) |
| 8-14 | Et | $CF_3$ | CO—c-Pr | $C(CF_3)_2OEt$ | CH | CMe | CH | 1 | |
| 8-15 | Et | $CF_3$ | CO—c-Pr | $C(CF_3)_2OEt$ | CH | CMe | CH | 2 | |
| 8-16 | Et | $CF_3$ | CO—c-Pr | $C(CF_3)_2O\text{—}i\text{-}Pr$ | CH | CMe | CH | 0 | 1.5020 (20.0) |
| 8-17 | Et | $CF_3$ | CO—c-Pr | $C(CF_3)_2O\text{—}i\text{-}Pr$ | CH | CMe | CH | 1 | |
| 8-18 | Et | $CF_3$ | CO—c-Pr | $C(CF_3)_2O\text{—}i\text{-}Pr$ | CH | CMe | CH | 2 | |
| 8-19 | Et | $CF_3$ | CO—c-Pr | $C(CF_3)_2OMe$ | CH | CH | C—i-Bu | 0 | |
| 8-20 | Et | $CF_3$ | CO—c-Pr | $C(CF_3)_2OMe$ | CH | CH | C—i-Bu | 1 | |
| 8-21 | Et | $CF_3$ | CO—c-Pr | $C(CF_3)_2OMe$ | CH | CH | C—i-Bu | 2 | |
| 8-22 | Et | $CF_3$ | CO—c-Pr | $C(CF_3)_2OEt$ | CH | CCl | CH | 0 | |
| 8-23 | Et | $CF_3$ | CO—c-Pr | $C(CF_3)_2OEt$ | CH | CCl | CH | 1 | |
| 8-24 | Et | $CF_3$ | CO—c-Pr | $C(CF_3)_2OEt$ | CH | CCl | CH | 2 | |
| 8-25 | Et | $CF_3$ | CO—i-Pr | $CH_2CF_3$ | CH | CCl | CH | 0 | |
| 8-26 | Et | $CF_3$ | CO—i-Pr | $CH_2CF_3$ | CH | CCl | CH | 1 | |
| 8-27 | Et | $CF_3$ | CO—i-Pr | $CH_2CF_3$ | CH | CCl | CH | 2 | |
| 8-28 | Et | $CF_3$ | CO—i-Pr | $C(CF_3)_2OMe$ | CH | CCl | CH | 0 | |
| 8-29 | Et | $CF_3$ | CO—i-Pr | $C(CF_3)_2OMe$ | CH | CCl | CH | 1 | |
| 8-30 | Et | $CF_3$ | CO—i-Pr | $C(CF_3)_2OMe$ | CH | CCl | CH | 2 | |
| 8-31 | Et | $CF_3$ | CO—i-Pr | $i\text{-}C_3F_7$ | CH | CCOMe | CH | 0 | |
| 8-32 | Et | $CF_3$ | CO—i-Pr | $i\text{-}C_3F_7$ | CH | CCOMe | CH | 1 | |
| 8-33 | Et | $CF_3$ | CO—i-Pr | $i\text{-}C_3F_7$ | CH | CCOMe | CH | 2 | |
| 8-34 | Et | $CF_3$ | CO—i-Pr | $C(CF_3)_2OMe$ | CH | CMe | CH | 0 | |
| 8-35 | Et | $CF_3$ | CO—i-Pr | $C(CF_3)_2OMe$ | CH | CMe | CH | 1 | |
| 8-36 | Et | $CF_3$ | CO—i-Pr | $C(CF_3)_2OMe$ | CH | CMe | CH | 2 | |
| 8-37 | Et | $CF_3$ | CO—i-Pr | $C(CF_3)_2OEt$ | CH | CMe | CH | 0 | |
| 8-38 | Et | $CF_3$ | CO—i-Pr | $C(CF_3)_2OEt$ | CH | CMe | CH | 1 | |
| 8-39 | Et | $CF_3$ | CO—i-Pr | $C(CF_3)_2OEt$ | CH | CMe | CH | 2 | |
| 8-40 | Et | $CF_3$ | CO—i-Pr | $C(CF_3)_2O\text{—}i\text{-}Pr$ | CH | CMe | CH | 0 | |
| 8-41 | Et | $CF_3$ | CO—i-Pr | $C(CF_3)_2O\text{—}i\text{-}Pr$ | CH | CMe | CH | 1 | |
| 8-42 | Et | $CF_3$ | CO—i-Pr | $C(CF_3)_2O\text{—}i\text{-}Pr$ | CH | CMe | CH | 2 | |
| 8-43 | Et | $CF_3$ | CO—i-Pr | $C(CF_3)_2OMe$ | CH | CH | C—i-Bu | 0 | |
| 8-44 | Et | $CF_3$ | CO—i-Pr | $C(CF_3)_2OMe$ | CH | CH | C—i-Bu | 1 | |
| 8-45 | Et | $CF_3$ | CO—i-Pr | $C(CF_3)_2OMe$ | CH | CH | C—i-Bu | 2 | |
| 8-46 | Et | $CF_3$ | CO—i-Pr | $C(CF_3)_2OEt$ | CH | CCl | CH | 0 | |
| 8-47 | Et | $CF_3$ | CO—i-Pr | $C(CF_3)_2OEt$ | CH | CCl | CH | 1 | |
| 8-48 | Et | $CF_3$ | CO—i-Pr | $C(CF_3)_2OEt$ | CH | CCl | CH | 2 | |

$R^6$ and $R^7$ each represent a hydrogen atom, and X represents an oxygen atom.
$R^6$ and $R^7$ each represent a hydrogen atom, and X represents an oxygen atom.

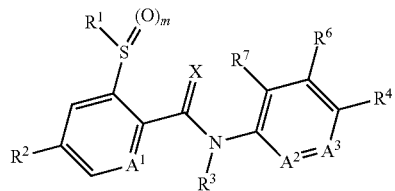

(I)

Pleuroptya ruralis, Cystidia couaggaria, Lampides boeticus, Cephonodes hylas, Helicoverpa armigera, Phalerodonta manleyi, Eumeta japonica, Pieris brassicae, Malacosoma neustria testacea, Stathmopoda masinissa, Cuphodes diospyrosella, Archips xylosteanus, Agrotis segetum, Tetramoera schistaceana, Papilio machaon hippocrates, Endoclyta sinensis, Lyonetia prunifoliella, Phyllonorycter ringoneella, Cydia kurokoi, Eucoenogenes aestuosa, Lobesia botrana, Latoia sinica, Euzophera batangensis, Phalonidia mesotypa, Spilosoma imparilis, Glyphodes pyloalis, Olethreutes mori, Tineola bisselliella, Endoclyta excrescens, Nemapogon granellus, Synanthedon hector, Cydia pomonella, Plutella xylostella, Cnaphalocrocis medinalis, Sesamia calamistis, Scirpophaga incertulas, Pediasia teterrellus, Phthorimaea operculella, Stauropus fagi persimilis,

TABLE 12

| Compound No. | $R^1$ | $R^2$ | $R^3$ | $R^4$ | $A^1$ | $A^2$ | $A^3$ | m | Physical property |
|---|---|---|---|---|---|---|---|---|---|
| 9-1 | Et | $CF_3$ | H | $CH_2CF_3$ | CH | CCl | CH | 0 | 111-112 |
| 9-2 | Et | $CF_3$ | H | $CH_2CF_3$ | CH | CCl | CH | 1 | 163.5-166 |
| 9-3 | Et | $CF_3$ | H | $CH_2CF_3$ | CH | CCl | CH | 2 | 117-120 |
| 9-4 | Et | $CF_3$ | H | $C(CF_3)_2OMe$ | CH | CCl | CH | 0 | 1.5285 (22.3) |
| 9-5 | Et | $CF_3$ | H | $C(CF_3)_2OMe$ | CH | CCl | CH | 1 | 146-147 |
| 9-6 | Et | $CF_3$ | H | $C(CF_3)_2OMe$ | CH | CCl | CH | 2 | 149.5-151 |
| 9-7 | Et | $CF_3$ | H | $i\text{-}C_3F_7$ | CH | CCOMe | CH | 0 | |
| 9-8 | Et | $CF_3$ | H | $i\text{-}C_3F_7$ | CH | CCOMe | CH | 1 | 1.5149 (21.4) |
| 9-9 | Et | $CF_3$ | H | $i\text{-}C_3F_7$ | CH | CCOMe | CH | 2 | 162-163 |
| 9-10 | Et | $CF_3$ | H | $C(CF_3)_2OMe$ | CH | CMe | CH | 0 | 79-81 |
| 9-11 | Et | $CF_3$ | H | $C(CF_3)_2OMe$ | CH | CMe | CH | 1 | 151-153 |
| 9-12 | Et | $CF_3$ | H | $C(CF_3)_2OMe$ | CH | CMe | CH | 2 | 201-202 |
| 9-13 | Et | $CF_3$ | H | $C(CF_3)_2OEt$ | CH | CMe | CH | 0 | 99-100 |
| 9-14 | Et | $CF_3$ | H | $C(CF_3)_2OEt$ | CH | CMe | CH | 1 | 150-151 |
| 9-15 | Et | $CF_3$ | H | $C(CF_3)_2OEt$ | CH | CMe | CH | 2 | 174-175 |
| 9-16 | Et | $CF_3$ | H | $C(CF_3)_2O\text{—}i\text{-}Pr$ | CH | CMe | CH | 0 | 72-76 |
| 9-17 | Et | $CF_3$ | H | $C(CF_3)_2O\text{—}i\text{-}Pr$ | CH | CMe | CH | 1 | 142-143 |
| 9-18 | Et | $CF_3$ | H | $C(CF_3)_2O\text{—}i\text{-}Pr$ | CH | CMe | CH | 2 | 162-163 |
| 9-19 | Et | $CF_3$ | H | $C(CF_3)_2OMe$ | CH | CH | C—i-Bu | 0 | 139-140 |
| 9-20 | Et | $CF_3$ | H | $C(CF_3)_2OMe$ | CH | CH | C—i-Bu | 1 | |
| 9-21 | Et | $CF_3$ | H | $C(CF_3)_2OMe$ | CH | CH | C—i-Bu | 2 | |
| 9-22 | Et | $CF_3$ | H | $C(CF_3)_2OEt$ | CH | CCl | CH | 0 | |
| 9-23 | Et | $CF_3$ | H | $C(CF_3)_2OEt$ | CH | CCl | CH | 1 | |
| 9-24 | Et | $CF_3$ | H | $C(CF_3)_2OEt$ | CH | CCl | CH | 2 | |

$R^6$ and $R^7$ each represent a hydrogen atom, and X represents an oxygen atom.

The agricultural and horticultural insecticide and microbicide comprising the amide compound represented by the general formula (I) of the present invention or a salt thereof as an active ingredient is suitable for controlling a variety of pests which may damage paddy rice, fruit trees, vegetables, other crops and ornamental flowering plants, and for controlling a variety of diseases which may damage cereals, fruit trees, vegetables, other crops and ornamental flowering plants. The target pests are, for example, agricultural and forest pests, horticultural pests, stored grain pests, sanitary pests, nematodes, etc. In addition, the insecticide and microbicide of the present invention is remarkably effective against pests which live on the exterior of or in the interior of pets and domestic animals, as described above.

Specific examples of the pests, nematodes, etc. include the following:
the species of the order Lepidoptera such as Parasa consocia, Anomis mesogona, Papilio xuthus, Matsumuraeses azukivora, Ostrinia scapulalis, Spodoptera exempta, Hyphantria cunea, Ostrinia furnacalis, Pseudaletia separata, Tinea translucens, Bactra furfurana, Parnara guttata, Marasmia exigua, Parnara guttata, Sesamia inferens, Brachmia triannulella, Monema flavescens, Trichoplusia ni, Etiella zinckenella, Spodoptera exigua, Palpifer sexnotata, Spodoptera mauritia, Scirpophaga innotata, Xestia c-nigrum, Spodoptera depravata, Ephestia kuehniella, Angerona prunaria, Clostera anastomosis, Pseudoplusia includens, Matsumuraeses falcana, Helicoverpa assulta, Autographa nigrisigna, Agrotis ipsilon, Euproctis pseudoconspersa, Adoxophyes orana, Caloptilia theivora, Homona magnanima, Ephestia elutella, Eumeta minuscula, Clostera anachoreta, Heliothis maritima, Sparganothis pilleriana, Busseola fusca, Euproctis subflava, Biston robustum, Heliothis zea, Aedia leucomelas, Narosoideus flavidorsalis, Viminia rumicis, Bucculatrix pyrivorella, Grapholita molesta, Spulerina astaurota, Ectomyelois pyrivorella, Chilo suppressalis, Acrolepiopsis sapporensis, Plodia interpunctella, Hellula undalis, Sitotroga cerealella, Spodoptera litura, a species of the family Tortricidae (Eucosma aporema), Acleris comariana, Scopelodes contractus, Orgyia thyellina, Spodoptera frugiperda, Ostrinia zaguliaevi, Naranga aenescens, Andraca bipunctata, Paranthrene regalis, Acosmeryx castanea, Phyllocnistis toparcha, Endopiza viteana, Eupoecillia ambiguella, Anticarsia gemmatalis, Cnephasia cinereipalpana, Lymantria dispar, Dendrolimus spectabilis, Leguminivora glycinivorella, Maruca testulalis, Matsumuraeses phaseoli, Caloptilia soyella, Phyllocnistis citrella, Omiodes indicata, Archips fuscocu-

*preanus, Acanthoplusia agnata, Bambalina* sp., *Carposina niponensis, Conogethes punctiferalis, Synanthedon* sp., *Lyonetia clerkella, Papilio helenus, Colias erate poliographus, Phalera flavescens*, the species of the family Pieridae such as *Pieris rapae crucivora* and *Pieris rapae, Euproctis similis, Acrolepiopsis suzukiella, Ostrinia nubilalis, Mamestra brassicae, Ascotis selenaria, Phtheochroides clandestina, Hoshinoa adumbratana, Odonestis pruni japonensis, Triaena intermedia, Adoxophyes orana fasciata, Grapholita inopinata, Spilonota ocellana, Spilonota lechriaspis, Illiberis pruni, Argyresthia conjugella, Caloptilia zachrysa, Archips breviplicanus, Anomis flava, Pectinophora gossypiella, Notarcha derogata, Diaphania indica, Heliothis virescens* and *Earias cupreoviridis*; the species of the order Hemiptera such as *Nezara antennata, Stenotus rubrovittatus, Graphosoma rubrolineatum, Trigonotylus coelestialium, Aeschynteles maculatus, Creontiades pallidifer, Dysdercus cingulatus, Chrysomphalus ficus, Aonidiella aurantii, Graptopsaltria nigrofuscata, Blissus leucopterus, Icerya purchasi, Piezodorus hybneri, Lagynotomus elongatus, Thaia subrufa, Scotinophara lurida, Sitobion ibarae, Stariodes iwasakii, Aspidiotus destructor, Taylorilygus pallidulus, Myzus mumecola, Pseudaulacaspis prunicola, Acyrthosiphon pisum, Anacanthocoris striicornis, Ectometopterus micantulus, Eysarcoris lewisi, Molipteryx fuliginosa, Cicadella viridis, Rhopalosophumrufiabdominalis, Saissetia oleae, Trialeurodes vaporariorum, Aguriahana quercus, Lygus* spp., *Euceraphis punctipennis, Andaspis kashicola, Coccus pseudomagnoliarum, Cavelerius saccharivorus, Galeatus spinifrons, Macrosiphoniella sanborni, Aonidiella citrina, Halyomorpha mista, Stephanitis fasciicarina, Trioza camphorae, Leptocorisa chinensis, Trioza quercicola, Uhlerites latius, Erythroneura comes, Paromius exiguus, Duplaspidiotus claviger, Nephotettix nigropictus, Halticiellus insularis, Perkinsiella saccharicida, Psylla malivorella, Anomomeura mori, Pseudococcus longispinis, Pseudaulacaspis pentagona, Pulvinaria kuwacola, Apolygus lucorum, Togo hemipterus, Toxoptera aurantii, Saccharicoccus sacchari, Geoica lucifuga, Numata muiri, Comstockaspis perniciosa, Unaspis citri, Aulacorthum solani, Eysarcoris ventralis, Bemisia argentifolii, Cicadella spectra, Aspidiotus hederae, Liorhyssus hyalinus, Calophya nigridorsalis, Sogatella furcifera, Megoura crassicauda, Brevicoryne brassicae, Aphis glycines, Leptocorisa oratorios, Nephotettix virescens, Uroeucon formosanum, Cyrtopeltis tennuis, Bemisia tabaci, Lecanium persicae, Parlatoria theae, Pseudaonidia paeoniae, Empoasca onukii, Plautia stali, Dysaphis tulipae, Macrosiphum euphorbiae, Stephanitis pyrioides, Ceroplastes ceriferus, Parlatoria camelliae, Apolygus spinolai, Nephotettix cincticeps, Glaucias subpunctatus, Orthotylus flavosparsus, Rhopalosiphum maidis, Peregrinus maidis, Eysarcoris parvus, Cimex lectularius, Psylla abieti, Nilaparvata lugens, Psylla tobirae, Eurydema rugosum, Schizaphis piricola, Psylla pyricola, Parlatoreopsis pyri, Stephanitis nashi, Dysmicoccus wistariae, Lepholeucaspis japonica, Sappaphis piri, Lipaphis erysimi, Neotoxoptera formosana, Rhopalosophum nymphaeae, Edwardsiana rosae, Pinnaspis aspidistrae, Psylla alni, Speusotettix subfusculus, Alnetoidia alneti, Sogatella panicicola, Adelphocoris lineolatus, Dysdercus poecilus, Parlatoria ziziphi, Uhlerites debile, Laodelphax striatella, Eurydema pulchrum, Cletus trigones, Clovia punctata, Empoasca* sp., *Coccus hesperidum, Pachybrachius luridus, Planococcus kraunhiae, Stenotus binotatus, Arboridia apicalis, Macrosteles fascifrons, Dolycoris baccarum, Adelphocoris triannulatus, Viteus vitifolii, Acanthocoris sordidus, Leptocorisa aceta, Macropes obnubilus, Cletus punctiger, Riptortus clavatus, Paratrioza cockerelli, Aphrophora costalis, Lygus disponsi, Lygus saundersi, Crisicoccus pini, Empoasca abietis, Crisicoccus matsumotoi, Aphis craccivora, Megacopta punctatissimum, Eysarcoris guttiger, Lepidosaphes beckii, Diaphorina citri, Toxoptera citricidus, Planococcus citri, Dialeurodes citri, Aleurocanthus spiniferus, Pseudococcus citriculus, Zyginella citri, Pulvinaria citricola, Coccus discrepans, Pseudaonidia duplex, Pulvinaria aurantii, Lecanium corni, Nezara viridula, Stenodema calcaratum, Rhopalosiphum padi, Sitobion akebiae, Schizaphis graminum, Sorhoanus tritici, Brachycaudus helichrysi, Carpocoris purpureipennis, Myzus persicae, Hyalopteruspruni, Aphis farinoseyanagicola, Metasalispopuli, Unaspis yanonensis, Mesohomotoma camphorae, Aphis spiraecola, Aphis pomi, Lepidosaphes ulmi, Psylla mali, Heterocordylus flavipes, Myzus malisuctus, Aphidonuguis mali, Orientus ishidai, Ovatus malicolens, Eriosoma lanigerum, Ceroplastes rubens* and *Aphis gossypii*;

the species of the order Coleoptera such as *Xystrocera globosa, Paederus fuscipes, Eucetonia roelofsi, Callosobruchus chinensis, Cylas formicarius, Hypera postica, Echinocnemus squameus, Oulema oryzae, Donacia provosti, Lissorhoptrus oryzophilus, Colasposoma dauricum, Euscepes postfasciatus, Epilachna varivestis, Acanthoscelides obtectus, Diabrotica virgifera virgifera, Involvulus cupreus, Aulacophora femoralis, Bruchus pisorum, Epilachna vigintioctomaculata, Carpophilus dimidiatus, Cassida nebulosa, Luperomorpha tunebrosa, Phyllotreta striolata, Psacothea hilaris, Aeolesthes chrysothrix, Curculio sikkimensis, Carpophilus hemipterus, Oxycetonia jucunda, Diabrotica* spp., *Mimela splendens, Sitophilus zeamais, Tribolium castaneum, Sitophilus oryzae, Palorus subdepressus, Melolontha japonica, Anoplophora malasiaca, Meatus picipes, Leptinotarsa decemlineata, Diabrotica undecimpunctata howardi, Sphenophorus venatus, Crioceris quatuordecimpunctata, Conotrachelus nenuphar, Ceuthorhynchidius albosuturalis, Phaedon brassicae, Lasioderma serricorne, Sitona japonicus, Adoretus tenuimaculatus, Tenebrio molitor, Basilepta balyi, Hypera nigrirostris, Chaetocnema concinna, Anomala cuprea, Heptophylla picea, Epilachna vigintioctopunctata, Diabrotica longicornis, Eucetonia pilifera, Agriotes* spp., *Attagenus unicolor japonicus, Pagria signata, Anomala rufocuprea, Palorus ratzeburgii, Alphitobius laevigatus, Anthrenus verbasci, Lyctus brunneus, Tribolium confusum, Medythia nigrobilineata, Xylotrechus pyrrhoderus, Epitrix cucumeris, Tomicus piniperda, Monochamus alternatus, Popillia japonica, Epicauta gorhami, Sitophilus zeamais, Rhynchites heros, Listroderes costirostris, Callosobruchus maculatus, Phyllobius armatus, Anthonomus pomorum, Linaeidea aenea* and *Anthonomus grandis*;

the species of the order Diptera such as *Culex pipiens pallens, Pegomya hyoscyami, Liriomyza huidobrensis, Musca domestica, Chlorops oryzae, Hydrellia sasakii, Agromyza oryzae, Hydrellia griseola, Hydrellia griseola, Ophiomyia phaseoli, Dacus cucurbitae, Drosophila suzukii, Rhacochlaena japonica, Muscina stabulans*, the species of the family Phoridae such as *Megaselia spiracularis, Clogmia albipunctata, Tipula aino, Phormia regina, Culex tritaeniorhynchus, Anopheles sinensis, Hylemya brassicae, Asphondylia* sp., *Delia platura, Delia antiqua, Rhagoletis cerasi, Culex pipiens molestus Forskal, Ceratitis capitata, Bradysia agrestis, Pegomya cunicularia, Liriomyza sativae, Liriomyza bryoniae, Chromatomyia horticola, Liriomyza chinensis, Culex quinquefasciatus, Aedes aegypti, Aedes albopictus, Liriomyza trifolii, Liriomyza sativae, Dacus dorsalis, Dacus tsuneonis, Sitodiplosis mosellana, Meromuza* nigriventris, Anastrepha ludens and Rhagoletis pomonella; the species of the order Hymenoptera such as Pristomyrmex pungens, the species of the family Bethylidae, Monomorium pharaonis, Pheidole noda, Athalia rosae, Dryocosmus kuriphilus, Formica fusca japonica, the species of the subfamily Vespinae, Athalia infumata infumata, Arge pagana, Athalia japonica, Acromyrmex spp., Solenopsis spp., Arge mali and Ochetellus glaber;

the species of the order Orthoptera such as Homorocoryphus lineosus, Gryllotalpa sp., Oxyahylaintricata, Oxyayezoensis, Locusta migratoria, Oxya japonica, Homorocoryphus jezoensis and Teleogryllus emma;

the species of the order Thysanoptera such as Selenothrips rubrocinctus, Stenchaetothrips biformis, Haplothrips aculeatus, Ponticulothrips diospyrosi, Thrips flavus, Anaphothrips obscurus, Liothrips floridensis, Thrips simplex, Thrips nigropilosus, Heliothrips haemorrhoidalis, Pseudodendrothrips mori, Microcephalothrips abdominalis, Leeuwenia pasanii, Litotetothrips pasaniae, Scirtothrips citri, Haplothrips chinensis, Mycterothrips glycines, Thrips setosus, Scirtothrips dorsalis, Dendrothrips minowai, Haplothrips niger, Thrips tabaci, Thrips alliorum, Thrips hawaiiensis, Haplothrips kurdjumovi, Chirothrips manicatus, Frankliniella intonsa, Thrips coloratus, Frankliniella occidentalis, Thrips palmi, Frankliniella lilivora and Liothrips vaneeckei;

the species of the order Acari such as Leptotrombidium akamushi, Tetranychus ludeni, Dermacentor variabilis, Tetranychus truncatus, Ornithonyssus bacoti, Demodex canis, Tetranychus viennensis, Tetranychus kanzawai, the species of the family Ixodidae such as Rhipicephalus sanguineus, Cheyletus malaccensis, Tyrophagus putrescentiae, Dermatophagoides farinae, Latrodectus hasseltii, Dermacentor taiwanicus, Acaphylla theavagrans, Polyphagotarsonemus latus, Aculops lycopersici, Ornithonyssus sylvairum, Tetranychus urticae, Eriophyes chibaensis, Brevipalpus sp., Sarcoptes scabiei, Haemaphysalis longicornis, Ixodes scapularis, Tyrophagus similis, Cheyletus eruditus, Panonychus citri, Cheyletus moorei, Brevipalpus phoenicis, Octodectes cynotis, Dermatophagoides ptrenyssnus, Haemaphysalis flava, Ixodes ovatus, Phyllocoptruta citri, Aculus schlechtendali, Panonychus ulmi, Amblyomma americanum, Dermanyssus gallinae, Rhyzoglyphus robini and Sancassania sp.;

the species of the order Isoptera such as Reticulitermes miyatakei, Incisitermes minor, Coptotermes formosanus, Hodotermopsis japonica, Reticulitermes sp., Reticulitermes flaviceps amamianus, Glyptotermes kushimensis, Coptotermes guangzhoensis, Neotermes koshunensis, Glyptotermes kodamai, Glyptotermes satsumensis, Cryptotermes domesticus, Odontotermes formosanus, Glyptotermes nakajimai, Pericapritermes nitobei and Reticulitermes speratus; the species of the order Blattodea such as Periplaneta fuliginosa, Blattella germanica, Blatta orientalis, Periplaneta brunnea, Blattella lituricollis, Periplaneta japonica and Periplaneta americana;

the species of the phylum Nematoda such as Nothotylenchus acris, Aphelenchoides besseyi, Pratylenchus penetrans, Meloidogyne hapla, Meloidogyne incognita, Globodera rostochiensis, Meloidogyne javanica, Heterodera glycines, Pratylenchus coffeae, Pratylenchus neglectus and Tylenchus semipenetrans; and the species of the phylum Mollusca such as Pomacea canaliculata, Achatina fulica, Meghimatium bilineatum, Lehmannina valentiana, Limax flavus and Acusta despecta sieboldiana.

In addition, the agricultural and horticultural insecticide of the present invention has a strong insecticidal effect on Tuta absoluta as well.

Further, mites and ticks parasitic on animals are also included in the target pests, and the examples include the species of the family Ixodidae such as Boophilus microplus, Rhipicephalus sanguineus, Haemaphysalis longicornis, Haemaphysalis flava, Haemaphysalis campanulata, Haemaphysalis concinna, Haemaphysalis japonica, Haemaphysalis kitaokai, Haemaphysalis ias, Ixodes ovatus, Ixodes nipponensis, Ixodes persulcatus, Amblyomma testudinarium, Haemaphysalis megaspinosa, Dermacentor reticulatus and Dermacentor taiwanesis; Dermanyssus gallinae; the species of the genus Ornithonyssus such as Ornithonyssus sylviarum and Ornithonyssus bursa; the species of the family Trombiculidae such as Eutrombicula wichmanni, Leptotrombidium akamushi, Leptotrombidium pallidum, Leptotrombidium fuji, Leptotrombidium Cosa, Neotrombicula autumnalis, Eutrombicula alfreddugesi and Helenicula miyagawai; the species of the family Cheyletidae such as Cheyletiella yasguri, Cheyletiella parasitivorax and Cheyletiella blakei; the species of the superfamily Sarcoptoidea such as Psoroptes cuniculi, Chorioptes bovis, Otodectes cynotis, Sarcoptes scabiei and Notoedres cati; and the species of the family Demodicidae such as Demodex canis.

Other target pests include fleas including ectoparasitic wingless insects belonging to the order Siphonaptera, more specifically, the species belonging to the families Pulicidae and Ceratophyllidae. Examples of the species belonging to the family Pulicidae include Ctenocephalides canis, Ctenocephalides felis, Pulex irritans, Ceratophyllus gallinae, Echidnophaga gallinacea, Xenopsylla cheopis, Leptopsylla segnis, Nosopsyllus fasciatus and Monopsyllus anisus.

Other target pests include ectoparasites of animals, for example, the species of the suborder Anoplura such as Haematopinus eurysternus, Haematopinus asini, Dalmalinia ovis, Linognathus vituli, Haematopinus suis, Phthirus pubis and Pediculus capitis; the species of the suborder Mallophaga such as Trichodectes canis; and hematophagous Dipteran insect pests such as Tabanus trigonus, Culicoides schultzei and Simulium ornatum. In addition, examples of endoparasites of animals include nematodes such as lungworms, whipworms, nodular worms, endogastric parasitic worms, ascarides and filarial worms; cestodes such as Spirometra erinacei, Diphyllobothrium latum, Dipylidium caninum, Multiceps multiceps, Echinococcus granulosus and Echinococcus multilocularis; trematodes such as Schistosoma japonicum and Fasciola hepatica; and protozoa such as coccidia, Plasmodium, intestinal Sarcocystis, Toxoplasma and Cryptosporidium.

As is clear from the above, the compound of the present invention can exterminate not only agricultural and horticultural pests but also sanitary pests.

The target diseases include filamentous fungal diseases, bacterial diseases and viral diseases. Examples of the filamentous fungal diseases include diseases caused by fungi-imperfecti including the genera Botrytis, Helminthosporium, Fusarium, Septoria, Cercospora, Pseudocercosporella, Rhynchosporium, Pyricularia and Alternaria; diseases caused by basidiomycetes including the genera Hemilelia, Rhizoctonia, Ustilago, Typhula and Puccinia; diseases caused by ascomycota including the genera Venturia, Podosphaera, Leptosphaeria, Blumeria, Erysiphe, Microdochium, Sclerotinia, Gaeumannomyces, Monilinia and Unsinula; and diseases caused by other fungi including the genera Ascochyta, Phoma, Pythium, Corticium and Pyrenophora. Examples of the bacterial diseases include diseases caused by bacteria including the genera *Pseudomonas*, *Xanthomonas* and *Erwinia*. Examples of the viral diseases include diseases caused by viruses including tobacco mosaic virus.

Specific examples of the filamentous fungal diseases include rice blast (*Pyricularia oryzae*), rice sheath blight (*Rhizoctonia solani*), rice brown spot (*Cochiobolus miyabeanus*), rice seedling blight (*Rhizopus chinensis, Pythiurngraminicola, Fusarium graminicola, Fusarium roseum, Mucor* sp., *Phoma* sp., *Tricoderma* sp.), rice bakanae disease (*Gibberella fujikuroi*), powdery mildew of barley, wheat, etc. (*Blumeria graminis*), powdery mildew of cucumbers etc. (*Sphaerotheca fuliginea*), powdery mildew of eggplants etc. (*Erysiphe cichoracoarum*), powdery mildew of other host plants, eyespot of barley, wheat, etc. (*Pseudocercosporella herpotrichoides*), smut of wheat etc. (*Urocystis tritici*), snow mold of barley, wheat, etc. (*Microdochium nivalis, Pythium iwayamai, Typhla ishikariensis, Typhla incarnata, Sclerotinia borealis*), *fusarium* ear blight of barley, wheat, etc. (*Fusarium graminearum, Fusarium avenaceum, Fusarium culmorum, Microdochium nivalis*), rust of barley, wheat, etc. (*Puccinia recondita, Puccinia striiformis, Puccinia graminis*), take-all of barley, wheat, etc. (*Gaeumannomyces graminis*), oat crown rust (*Puccinia coronata*), rust of other plants, gray mold of cucumbers, strawberries, etc. (*Botrytis cinerea*), *sclerotinia* rot of tomatoes, cabbages, etc. (*Sclerotinia sclerotiorum*), late blight of potatoes, tomatoes, etc. (*Phytophthora infestans*), late blight of other plants, cucumber downy mildew (*Pseudoperonospora cubensis*), grape downy mildew (*Plasmopara viticola*), downy mildew of various plants, apple scab (*Venturia inaequalis*), apple *alternaria* blotch (*Alternaria mali*), pear black spot (*Alternaria kikuchiana*), citrus melanose (*Diaporthe citri*), citrus scab (*Elsinoe fawcetti*), sugarbeet leaf spot (*Cercospora beticola*), peanut brown leaf spot (*Cercospora arachidicola*), peanut late leaf spot (*Cercospora personata*), leaf blotch of wheat (*Septoria tritici*), wheat glume blotch (*Leptosphaeria nodorum*), barley net blotch (*Pyrenophora teres*), barley stripe (*Pyrenophora graminea*), barley scald (*Rhynchosporium secalis*), wheat loose smut (*Ustilago nuda*), wheat stinking smut (*Tilletia caries*), brown patch of turfgrass (*Rhizoctonia solani*) and dollar spot of turfgrass (*Sclerotinia homoeocarpa*).

Specific examples of the bacterial diseases include diseases caused by *Pseudomonas* spp. such as cucumber bacterial spot (*Pseudomonas syringae* pv. *lachrymans*), tomato bacterial wilt disease (*Pseudomonas solanacearum*) and bacterial grain rot of rice (*Pseudomonas glumae*); diseases caused by *Xanthomonas* spp. such as cabbage black rot (*Xanthomonas campestris*), rice bacterial leaf blight (*Xanthomonas oryzae*) and citrus canker (*Xanthomonas citri*); and diseases caused by *Erwinia* spp. such as cabbage soft rot (*Erwinia carotovora*). Specific examples of the viral diseases include tobacco mosaic disease (tobacco mosaic virus).

In particular, the agricultural and horticultural insecticide and microbicide is highly effective against powdery mildew of barley, wheat, etc. (*Blumeria graminis*), powdery mildew of cucumbers etc. (*Sphaerotheca fuliginea*), powdery mildew of eggplants etc. (*Erysiphe cichoracoarum*) and powdery mildew of other host plants.

The agricultural and horticultural insecticide and microbicide comprising the amide compound represented by the general formula (I) of the present invention or a salt thereof as an active ingredient has a remarkable control effect on the above-described pests which damage lowland crops, field crops, fruit trees, vegetables, other crops, ornamental flowering plants, etc. The desired effect can be obtained when the agricultural and horticultural insecticide and microbicide is applied to nursery facilities for seedlings, paddy fields, fields, fruit trees, vegetables, other crops, ornamental flowering plants, etc. and their seeds, paddy water, foliage, cultivation media such as soil, or the like around the expected time of pest infestation, i.e., before the infestation or upon the confirmation of the infestation. In particularly preferable embodiments, the application of the agricultural and horticultural insecticide and microbicide utilizes so-called penetration and translocation. That is, nursery soil, soil in transplanting holes, plant foot, irrigation water, cultivation water in hydroponics, or the like is treated with the agricultural and horticultural insecticide and microbicide to allow crops, ornamental flowering plants, etc. to absorb the compound of the present invention through the roots via soil or otherwise.

The useful plants to which the agricultural and horticultural insecticide and microbicide of the present invention can be applied include, but are not particularly limited to, for example, cereals (e.g., rice, barley, wheat, rye, oats, corn, etc.), legumes (e.g., soybeans, azuki beans, broad beans, green peas, kidney beans, peanuts, etc.), fruit trees and fruits (e.g., apples, citrus fruits, pears, grapes, peaches, plums, cherries, walnuts, chestnuts, almonds, bananas, etc.), leaf and fruit vegetables (e.g., cabbages, tomatoes, spinach, broccoli, lettuce, onions, green onions (chives and Welsh onions), green peppers, eggplants, strawberries, pepper crops, okra, Chinese chives, etc.), root vegetables (e.g., carrots, potatoes, sweet potatoes, taros, Japanese radishes, turnips, lotus roots, burdock roots, garlic, Chinese scallions, etc.), crops for processing (e.g., cotton, hemp, beet, hops, sugarcane, sugar beet, olives, rubber, coffee, tobacco, tea, etc.), gourds (e.g., Japanese pumpkins, cucumbers, watermelons, oriental sweet melons, melons, etc.), pasture grass (e.g., orchardgrass, sorghum, timothy, clover, alfalfa, etc.), lawn grass (e.g., Korean lawn grass, bent grass, etc.), spice and aromatic crops and ornamental crops (e.g., lavender, rosemary, thyme, parsley, pepper, ginger, etc.), ornamental flowering plants (e.g., *chrysanthemum*, rose, carnation, orchid, tulip, lily, etc.), garden trees (e.g., ginkgo trees, cherry trees, Japanese *aucuba*, etc.) and forest trees (e.g., *Abies sachalinensis, Picea jezoensis*, pine, yellow cedar, Japanese cedar, hinoki cypress, *eucalyptus*, etc.). When the agricultural and horticultural insecticide and microbicide of the present invention is used as a microbicide, it is preferably applied to cereals.

The above-mentioned "plants" also include plants provided with herbicide tolerance by a classical breeding technique or a gene recombination technique. Examples of such herbicide tolerance include tolerance to HPPD inhibitors, such as isoxaflutole; ALS inhibitors, such as imazethapyr and thifensulfuron-methyl; EPSP synthase inhibitors, such as glyphosate; glutamine synthetase inhibitors, such as glufosinate; acetyl-CoA carboxylase inhibitors, such as sethoxydim; or other herbicides, such as bromoxynil, dicamba and 2,4-D.

Examples of the plants provided with herbicide tolerance by a classical breeding technique include varieties of rapeseed, wheat, sunflower and rice tolerant to the imidazolinone family of ALS-inhibiting herbicides such as imazethapyr, and such plants are sold under the trade name of Clearfield (registered trademark). Also included is a variety of soybean provided with tolerance to the sulfonyl urea family of ALS-inhibiting herbicides such as thifensulfuron-methyl by a classical breeding technique, and this is sold under the trade name of STS soybean. Also included are plants provided with tolerance to acetyl-CoA carboxylase inhibitors such as trione oxime herbicides and aryloxy phenoxy propionic acid herbicides by a classical breeding technique, for example, SR corn and the like.

Plants provided with tolerance to acetyl-CoA carboxylase inhibitors are described in Proc. Natl. Acad. Sci. USA, 87, 7175-7179 (1990), and the like. Further, acetyl-CoA carboxylase mutants resistant to acetyl-CoA carboxylase inhibitors are reported in Weed Science, 53, 728-746 (2005), and the like, and by introducing the gene of such an acetyl-CoA carboxylase mutant into plants by a gene recombination technique, or introducing a resistance-conferring mutation into acetyl-CoA carboxylase of plants, plants tolerant to acetyl-CoA carboxylase inhibitors can be engineered. Alternatively, by introducing a nucleic acid causing base substitution mutation into plant cells (a typical example of this technique is chimeraplasty technique (Gura T. 1999. Repairing the Genome's Spelling Mistakes. Science 285: 316-318.)) to allow site-specific substitution mutation in the amino acids encoded by an acetyl-CoA carboxylase gene, an ALS gene or the like of plants, plants tolerant to acetyl-CoA carboxylase inhibitors, ALS inhibitors or the like can be engineered. The agricultural and horticultural insecticide of the present invention can be applied to these plants as well.

Further, exemplary toxins expressed in genetically modified plants include insecticidal proteins derived from *Bacillus cereus* or *Bacillus popilliae; Bacillus thuringiensis*-derived δ-endotoxins, such as Cry1Ab, Cry1Ac, Cry1F, Cry1Fa2, Cry2Ab, Cry3A, Cry3Bb1 and Cry9C, and other insecticidal proteins, such as VIP1, VIP2, VIP3 and VIP3A; nematode-derived insecticidal proteins; toxins produced by animals, such as scorpion toxins, spider toxins, bee toxins and insect-specific neurotoxins; toxins of filamentous fungi; plant lectins; agglutinin; protease inhibitors, such as trypsin inhibitors, serine protease inhibitors, patatin, cystatin and papain inhibitors; ribosome inactivating proteins (RIP), such as ricin, maize RIP, abrin, luffin, saporin and bryodin; steroid metabolizing enzymes, such as 3-hydroxy steroid oxidase, ecdysteroid-UDP-glucosyltransferase and cholesterol oxidase; ecdysone inhibitors; HMG-CoA reductase; ion channel inhibitors, such as sodium channel inhibitors and calcium channel inhibitors; juvenile hormone esterase; diuretic hormone receptors; stilbene synthase; bibenzyl synthase; chitinase; and glucanase.

Also included are hybrid toxins, partially deficient toxins and modified toxins derived from the following: δ-endotoxin proteins such as Cry1Ab, Cry1Ac, Cry1F, Cry1Fa2, Cry2Ab, Cry3A, Cry3Bb1, Cry9C, Cry34Ab and Cry35Ab, and other insecticidal proteins such as VIP1, VIP2, VIP3 and VIP3A. The hybrid toxin can be produced by combining domains derived from these proteins differently from the original combination in nature with the use of a recombination technique. As the partially deficient toxin, a Cry1Ab toxin in which a part of the amino acid sequence is deleted is known. In the modified toxin, one or more amino acids of a naturally occurring toxin are substituted.

Examples of the foregoing toxins and genetically modified plants capable of synthesizing these toxins are described in EP-A-0 374 753, WO 93/07278, WO 95/34656, EP-A-0 427 529, EP-A-451 878, WO 03/052073, etc.

Due to the toxins contained in such genetically modified plants, the plants exhibit resistance to pests, in particular, Coleopteran insect pests, Hemipteran insect pests, Dipteran insect pests, Lepidopteran insect pests and nematodes. The above-described technologies and the agricultural and horticultural insecticide of the present invention can be used in combination or used systematically.

In order to control various pests, the agricultural and horticultural insecticide and microbicide of the present invention, with or without appropriate dilution or suspension in water etc., is applied to plants potentially infested with insect pests and nematodes in an amount effective for the control of the insect pests or the nematodes. For example, in order to control insect pests and nematodes that may damage crop plants such as fruit trees, cereals and vegetables, foliar application and seed treatment such as dipping, dust coating and calcium peroxide coating can be performed. Further, treatment of soil or the like may also be performed to allow plants to absorb agrochemicals through their roots. Examples of such treatment include whole soil incorporation, planting row treatment, bed soil incorporation, plug seedling treatment, planting hole treatment, plant foot treatment, top-dressing, treatment of nursery boxes for paddy rice, and submerged application. In addition, application to culture media in hydroponics, smoking treatment, trunk injection and the like can also be performed.

Further, the agricultural and horticultural insecticide and microbicide of the present invention, with or without appropriate dilution or suspension in water etc., can be applied to sites potentially infested with pests in an amount effective for the control of the pests. For example, it can be directly applied to stored grain pests, house pests, sanitary pests, forest pests, etc., and also be used for coating of residential building materials, for smoking treatment, or as a bait formulation.

Exemplary methods of seed treatment include dipping of seeds in a diluted or undiluted fluid of a liquid or solid formulation for the permeation of agrochemicals into the seeds; mixing or dust coating of seeds with a solid or liquid formulation for the adherence of the formulation onto the surfaces of the seeds; coating of seeds with a mixture of a solid or liquid formulation and an adhesive carrier such as resins and polymers; and application of a solid or liquid formulation to the vicinity of seeds at the same time as seeding.

The term "seed" in the above-mentioned seed treatment refers to a plant body which is in the early stages of cultivation and used for plant propagation. The examples include, in addition to a so-called seed, a plant body for vegetative propagation, such as a bulb, a tuber, a seed potato, a bulbil, a propagule, a discoid stem and a stem used for cuttage.

The term "soil" or "cultivation medium" in the method of the present invention for using an agricultural and horticultural insecticide and microbicide refers to a support medium for crop cultivation, in particular a support medium which allows crop plants to spread their roots therein, and the materials are not particularly limited as long as they allow plants to grow. Examples of the support medium include what is called soils, seedling mats and water, and specific examples of the materials include sand, pumice, vermiculite, diatomite, agar, gelatinous substances, high-molecular-weight substances, rock wool, glass wool, wood chip and bark.

Exemplary methods of the application to crop foliage or to stored grain pests, house pests, sanitary pests, forest pests, etc. include application of a liquid formulation, such as an emulsifiable concentrate and a flowable, or a solid formulation, such as a wettable powder and a water-dispersible granule, after appropriate dilution in water; dust application; and smoking.

Exemplary methods of soil application include application of a water-diluted or undiluted liquid formulation to the foot of plants, nursery beds for seedlings, or the like;

application of a granule to the foot of plants, nursery beds for seedlings, or the like; application of a dust, a wettable powder, a water-dispersible granule, a granule or the like onto soil and subsequent incorporation of the formulation into the whole soil before seeding or transplanting; and application of a dust, a wettable powder, a water-dispersible granule, a granule or the like to planting holes, planting rows or the like before seeding or planting.

To nursery boxes for paddy rice, for example, a dust, a water-dispersible granule, a granule or the like can be applied, although the suitable formulation may vary depending on the application time, in other words, depending on the cultivation stage such as seeding time, greening period and planting time. A formulation such as a dust, a water-dispersible granule, a granule or the like may be mixed with nursery soil. For example, such a formulation is incorporated into bed soil, covering soil or the whole soil. Simply, nursery soil and such a formulation may be alternately layered.

In the application to paddy fields, a solid formulation, such as a jumbo, a pack, a granule and a water-dispersible granule, or a liquid formulation, such as a flowable and an emulsifiable concentrate, is applied usually to flooded paddy fields. In a rice planting period, a suitable formulation, as it is or after mixed with a fertilizer or the like, may be applied onto soil or injected into soil. In addition, a solution of an emulsifiable concentrate, a flowable or the like may be applied to the source of water supply for paddy fields, such as a water inlet and an irrigation device. In this case, treatment can be accomplished with the supply of water and thus achieved in a labor-saving manner.

In the case of field crops, their seeds, cultivation media in the vicinity of their plants, or the like may be treated in the period of seeding to seedling culture. In the case of plants of which the seeds are directly sown in the field, in addition to direct seed treatment, plant foot treatment during cultivation is preferable. Specifically, the treatment can be performed by, for example, applying a granule onto soil, or drenching soil with a formulation in a water-diluted or undiluted liquid form. Another preferable treatment is incorporation of a granule into cultivation media before seeding.

In the case of culture plants to be transplanted, preferable examples of the treatment in the period of seeding to seedling culture include, in addition to direct seed treatment, drench treatment of nursery beds for seedlings with a formulation in a liquid form; and granule application to nursery beds for seedlings. Also included are treatment of planting holes with a granule; and incorporation of a granule into cultivation media in the vicinity of planting points at the time of fix planting.

The agricultural and horticultural insecticide of the present invention is commonly used as a formulation convenient for application, which is prepared in the usual method for preparing agrochemical formulations.

That is, the amide compound represented by the general formula (I) of the present invention or a salt thereof and an appropriate inactive carrier, and if needed an adjuvant, are blended in an appropriate ratio, and through the step of dissolution, separation, suspension, mixing, impregnation, adsorption and/or adhesion, are formulated into an appropriate form for application, such as a suspension concentrate, an emulsifiable concentrate, a soluble concentrate, a wettable powder, a water-dispersible granule, a granule, a dust, a tablet and a pack.

The composition (agricultural and horticultural insecticide and microbicide or animal parasite control agent) of the present invention can optionally contain an additive usually used for agrochemical formulations or animal parasite control agents in addition to the active ingredient. Examples of the additive include carriers such as solid or liquid carriers, surfactants, dispersants, wetting agents, binders, tackifiers, thickeners, colorants, spreaders, sticking/spreading agents, antifreezing agents, anti-caking agents, disintegrants and stabilizing agents. If needed, preservatives, plant fragments, etc. may also be used as the additive. These additives may be used alone or in a combination of two or more kinds.

Examples of the solid carriers include natural minerals, such as quartz, clay, kaolinite, pyrophyllite, sericite, talc, bentonite, acid clay, attapulgite, zeolite and diatomite; inorganic salts, such as calcium carbonate, ammonium sulfate, sodium sulfate and potassium chloride; organic solid carriers, such as synthetic silicic acid, synthetic silicates, starch, cellulose and plant powders (for example, sawdust, coconut shell, corn cob, tobacco stalk, etc.); plastics carriers, such as polyethylene, polypropylene and polyvinylidene chloride; urea; hollow inorganic materials; hollow plastic materials; and fumed silica (white carbon). These solid carriers may be used alone or in a combination of two or more kinds.

Examples of the liquid carriers include alcohols including monohydric alcohols, such as methanol, ethanol, propanol, isopropanol and butanol, and polyhydric alcohols, such as ethylene glycol, diethylene glycol, propylene glycol, hexylene glycol, polyethylene glycol, polypropylene glycol and glycerin; polyol compounds, such as propylene glycol ether; ketones, such as acetone, methyl ethyl ketone, methyl isobutyl ketone, diisobutyl ketone and cyclohexanone; ethers, such as ethyl ether, dioxane, ethylene glycol monoethyl ether, dipropyl ether and tetrahydrofuran; aliphatic hydrocarbons, such as normal paraffin, naphthene, isoparaffin, kerosene and mineral oil; aromatic hydrocarbons, such as benzene, toluene, xylene, solvent naphtha and alkyl naphthalene; halogenated hydrocarbons, such as dichloromethane, chloroform and carbon tetrachloride; esters, such as ethyl acetate, diisopropyl phthalate, dibutyl phthalate, dioctyl phthalate and dimethyl adipate; lactones, such as γ-butyrolactone; amides, such as dimethylformamide, diethylformamide, dimethylacetamide and N-alkyl pyrrolidinone; nitriles, such as acetonitrile; sulfur compounds, such as dimethyl sulfoxide; vegetable oils, such as soybean oil, rapeseed oil, cotton seed oil and castor oil; and water. These liquid carriers may be used alone or in a combination of two or more kinds.

Exemplary surfactants used as the dispersant or the wetting/spreading agent include nonionic surfactants, such as sorbitan fatty acid ester, polyoxyethylene sorbitan fatty acid ester, sucrose fatty acid ester, polyoxyethylene fatty acid ester, polyoxyethylene resin acid ester, polyoxyethylene fatty acid diester, polyoxyethylene alkyl ether, polyoxyethylene alkyl aryl ether, polyoxyethylene alkyl phenyl ether, polyoxyethylene dialkyl phenyl ether, polyoxyethylene alkyl phenyl ether-formaldehyde condensates, polyoxyethylene-polyoxypropylene block copolymers, polystyrene-polyoxyethylene block polymers, alkyl polyoxyethylene-polypropylene block copolymer ether, polyoxyethylene alkylamine, polyoxyethylene fatty acid amide, polyoxyethylene fatty acid bis(phenyl ether), polyalkylene benzyl phenyl ether, polyoxyalkylene styryl phenyl ether, acetylene diol, polyoxyalkylene-added acetylene diol, polyoxyethylene ether-type silicone, ester-type silicone, fluorosurfactants, polyoxyethylene castor oil and polyoxyethylene hydrogenated castor oil; anionic surfactants, such as alkyl sulfates, polyoxyethylene alkyl ether sulfates, polyoxyethylene alkyl phenyl ether sulfates, polyoxyethylene styryl phenyl ether sulfates, alkylbenzene sulfonates, alkylaryl sulfonates, lignosulfonates, alkyl sulfosuccinates, naphthalene sulfonates, alkylnaphthalene sulfonates, salts of naphthalenesulfonic acid-formaldehyde condensates, salts of alkylnaphthalenesulfonic acid-formaldehyde condensates, fatty acid salts, polycarboxylic acid salts, polyacrylates, N-methyl-fatty acid sarcosinates, resinates, polyoxyethylene alkyl ether phosphates and polyoxyethylene alkyl phenyl ether phosphates; cationic surfactants including alkyl amine salts, such as lauryl amine hydrochloride, stearyl amine hydrochloride, oleyl amine hydrochloride, stearyl amine acetate, stearyl aminopropyl amine acetate, alkyl trimethyl ammonium chloride and alkyl dimethyl benzalkonium chloride; and amphoteric surfactants, such as amino acid-type or betaine-type amphoteric surfactants. These surfactants may be used alone or in a combination of two or more kinds.

Examples of the binders or the tackifiers include carboxymethyl cellulose or salts thereof, dextrin, soluble starch, xanthan gum, guar gum, sucrose, polyvinyl pyrrolidone, gum arabic, polyvinyl alcohol, polyvinyl acetate, sodium polyacrylate, polyethylene glycols with an average molecular weight of 6,000 to 20,000, polyethylene oxides with an average molecular weight of 100,000 to 5,000,000, phospholipids (for example, cephalin, lecithin, etc.), cellulose powder, dextrin, modified starch, polyaminocarboxylic acid chelating compounds, cross-linked polyvinyl pyrrolidone, maleic acid-styrene copolymers, (meth)acrylic acid copolymers, half esters of polyhydric alcohol polymer and dicarboxylic anhydride, water soluble polystyrene sulfonates, paraffin, terpene, polyamide resins, polyacrylates, polyoxyethylene, waxes, polyvinyl alkyl ether, alkylphenol-formaldehyde condensates and synthetic resin emulsions.

Examples of the thickeners include water soluble polymers, such as xanthan gum, guar gum, diutan gum, carboxymethyl cellulose, polyvinyl pyrrolidone, carboxyvinyl polymers, acrylic polymers, starch compounds and polysaccharides; and inorganic fine powders, such as high grade bentonite and fumed silica (white carbon).

Examples of the colorants include inorganic pigments, such as iron oxide, titanium oxide and prussian blue; and organic dyes, such as alizarin dyes, azo dyes and metal phthalocyanine dyes.

Examples of the antifreezing agents include polyhydric alcohols, such as ethylene glycol, diethylene glycol, propylene glycol and glycerin.

Examples of the adjuvants serving to prevent caking or facilitate disintegration include polysaccharides (starch, alginic acid, mannose, galactose, etc.), polyvinyl pyrrolidone, fumed silica (white carbon), ester gum, petroleum resin, sodium tripolyphosphate, sodium hexametaphosphate, metal stearates, cellulose powder, dextrin, methacrylate copolymers, polyvinyl pyrrolidone, polyaminocarboxylic acid chelating compounds, sulfonated styrene-isobutylene-maleic anhydride copolymers and starch-polyacrylonitrile graft copolymers.

Examples of the stabilizing agents include desiccants, such as zeolite, quicklime and magnesium oxide; antioxidants, such as phenolic compounds, amine compounds, sulfur compounds and phosphoric acid compounds; and ultraviolet absorbers, such as salicylic acid compounds and benzophenone compounds.

Examples of the preservatives include potassium sorbate and 1,2-benzothiazolin-3-one.

Further, other adjuvants including functional spreading agents, activity enhancers such as metabolic inhibitors (piperonyl butoxide etc.), antifreezing agents (propylene glycol etc.), antioxidants (BHT etc.) and ultraviolet absorbers can also be used if needed.

The content of the active ingredient compound in the agricultural and horticultural insecticide of the present invention can be adjusted as needed, and for example, is appropriately selected from the range of 0.01 to 90 parts by weight in 100 parts by weight of the agricultural and horticultural insecticide. For example, in the case where the agricultural and horticultural insecticide is a dust, a granule, an emulsifiable concentrate or a wettable powder, it is suitable that the content of the active ingredient compound is 0.01 to 50 parts by weight (0.01 to 50% by weight relative to the total weight of the agricultural and horticultural insecticide).

The application amount of the agricultural and horticultural insecticide and microbicide of the present invention may vary with various factors, for example, the purpose, the target pest, the growing conditions of crops, the tendency of pest infestation, the weather, the environmental conditions, the dosage form, the application method, the application site, the application time, etc., but for example, the application amount of the active ingredient compound per 10 ares is appropriately selected from the range of 0.001 g to 10 kg, and preferably 0.01 g to 1 kg depending on the purpose.

Furthermore, for the expansion of the range of target pests and the appropriate application time for control of pests, or for dose reduction, the agricultural and horticultural insecticide and microbicide of the present invention can be used after mixed with other agricultural or horticultural insecticides, acaricides, nematicides, microbicides, biopesticides and/or the like. Further, the agricultural and horticultural insecticide and microbicide can be used after mixed with herbicides, plant growth regulators, fertilizers and/or the like depending on its application.

Examples of such additional agricultural and horticultural insecticides, acaricides and nematicides used for the above-mentioned purposes include 3,5-xylyl methylcarbamate (XMC), crystalline protein toxins produced by *Bacillus thuringiensis* such as *Bacillus thuringiensis aizawai*, *Bacillus thuringiensis israelensis*, *Bacillus thuringiensis japonensis*, *Bacillus thuringiensis kurstaki* and *Bacillus thuringiensis tenebrionis*, BPMC, Bt toxin-derived insecticidal compounds, chlorfenson (CPCBS), dichlorodiisopropyl ether (DCIP), 1,3-dichloropropene (D-D), DDT, NAC, O-4-dimethylsulfamoylphenyl O,O-diethyl phosphorothioate (DSP), O-ethyl O-4-nitrophenyl phenylphosphonothioate (EPN), tripropylisocyanurate (TPIC), acrinathrin, azadirachtin, azinphos-methyl, acequinocyl, acetamiprid, acetoprole, acephate, abamectin, avermectin-B, amidoflumet, amitraz, alanycarb, aldicarb, aldoxycarb, aldrin, alpha-endosulfan, alpha-cypermethrin, albendazole, allethrin, isazofos, isamidofos, isoamidofos, isoxathion, isofenphos, isoprocarb (MIPC), ivermectin, imicyafos, imidacloprid, imiprothrin, indoxacarb, esfenvalerate, ethiofencarb, ethion, ethiprole, etoxazole, ethofenprox, ethoprophos, etrimfos, emamectin, emamectin-benzoate, endosulfan, empenthrin, oxamyl, oxydemeton-methyl, oxydeprofos (ESP), oxibendazole, oxfendazole, potassium oleate, sodium oleate, cadusafos, cartap, carbaryl, carbosulfan, carbofuran, gamma-cyhalothrin, xylylcarb, quinalphos, kinoprene, chinomethionat, cloethocarb, clothianidin, clofentezine, chromafenozide, chlorantraniliprole, chlorethoxyfos, chlordimeform, chlordane, chlorpyrifos, chlorpyrifos-methyl, chlorphenapyr, chlorfenson, chlorfenvinphos, chlorfluazuron, chlorobenzilate, chlorobenzoate, kelthane (dicofol), salithion, cyanophos (CYAP), diafenthiuron, diamidafos, cyantraniliprole, theta-cypermethrin, dienochlor, cyenopyrafen, dioxabenzofos, diofenolan, sigma-cypermethrin, dichlofenthion (ECP), cycloprothrin, dichlorvos (DDVP), disulfoton, dinotefuran, cyhalothrin, cyphenothrin, cyfluthrin, diflubenzuron, cyflumetofen, diflovidazin, cyhexatin, cypermethrin, dimethylvinphos, dimethoate, dimefluthrin, silafluofen, cyromazine, spinetoram, spinosad, spirodiclofen, spirotetramat, spiromesifen, sulfluramid, sulprofos, sulfoxaflor, zeta-cypermethrin, diazinon, tau-fluvalinate, dazomet, thiacloprid, thiamethoxam, thiodicarb, thiocyclam, thiosultap, thiosultap-sodium, thionazin, thiometon, deet, dieldrin, tetrachlorvinphos, tetradifon, tetramethylfluthrin, tetramethrin, tebupirimfos, tebufenozide, tebufenpyrad, tefluthrin, teflubenzuron, demeton-S-methyl, temephos, deltamethrin, terbufos, tralopyril, tralomethrin, transfluthrin, triazamate, triazuron, trichlamide, trichlorphon (DEP), triflumuron, tolfenpyrad, naled (BRP), nithiazine, nitenpyram, novaluron, noviflumuron, hydroprene, vaniliprole, vamidothion, parathion, parathion-methyl, halfenprox, halofenozide, bistrifluron, bisultap, hydramethylnon, hydroxy propyl starch, binapacryl, bifenazate, bifenthrin, pymetrozine, pyraclofos, pyrafluprole, pyridafenthion, pyridaben, pyridalyl, pyrifluquinazon, pyriprole, pyriproxyfen, pirimicarb, pyrimidifen, pirimiphos-methyl, pyrethrins, fipronil, fenazaquin, fenamiphos, phenisobromolate, fenitrothion (MEP), fenoxycarb, fenothiocarb, phenothrin, fenobucarb, fensulfothion, fenthion (MPP), phenthoate (PAP), fenvalerate, fenpyroximate, fenpropathrin, fenbendazole, fosthiazate, formetanate, butathiofos, buprofezin, furathiocarb, prallethrin, fluacrypyrim, fluazinam, fluazuron, fluensulfone, flucycloxuron, flucythrinate, fluvalinate, flupyrazofos, flufenerim, flufenoxuron, flufenzine, flufenprox, fluproxyfen, flubrocythrinate, flubendiamide, flumethrin, flurimfen, prothiofos, protrifenbute, flonicamid, propaphos, propargite (BPPS), profenofos, profluthrin, propoxur (PHC), bromopropylate, beta-cyfluthrin, hexaflumuron, hexythiazox, heptenophos, permethrin, benclothiaz, bendiocarb, bensultap, benzoximate, benfuracarb, phoxim, phosalone, fosthiazate, fosthietan, phosphamidon, phosphocarb, phosmet (PMP), polynactins, formetanate, formothion, phorate, machine oil, malathion, milbemycin, milbemycin-A, milbemectin, mecarbam, mesulfenfos, methomyl, metaldehyde, metaflumizone, methamidophos, metam-ammonium, metam-sodium, methiocarb, methidathion (DMTP), methylisothiocyanate, methylneodecanamide, methylparathion, metoxadiazone, methoxychlor, methoxyfenozide, metofluthrin, methoprene, metolcarb, meperfluthrin, mevinphos, monocrotophos, monosultap, lambda-cyhalothrin, ryanodine, lufenuron, resmethrin, lepimectin, rotenone, levamisole hydrochloride, fenbutatin oxide, morantel tartarate, methyl bromide, tricyclohexyltin hydroxide (cyhexatin), calcium cyanamide, calcium polysulfide, sulfur and nicotine-sulfate.

Examples of the agricultural and horticultural microbicides used for the same purposes as above include aureofungin, azaconazole, azithiram, acypetacs, acibenzolar, acibenzolar-S-methyl, azoxystrobin, anilazine, amisulbrom, ampropylfos, ametoctradin, allyl alcohol, aldimorph, amobam, isotianil, isovaledione, isopyrazam, isoprothiolane, ipconazole, iprodione, iprovalicarb, iprobenfos, imazalil, iminoctadine, iminoctadine-albesilate, iminoctadine-triacetate, imibenconazole, uniconazole, uniconazole-P, echlomezole, edifenphos, etaconazole, ethaboxam, ethirimol, etem, ethoxyquin, etridiazole, enestroburin, epoxiconazole, oxadixyl, oxycarboxin, copper-8-quinolinolate, oxytetracycline, copper-oxinate, oxpoconazole, oxpoconazole-fumarate, oxolinic acid, octhilinone, ofurace, orysastrobin, metamsodium, kasugamycin, carbamorph, carpropamid, carbendazim, carboxin, carvone, quinazamid, quinacetol, quinoxyfen, quinomethionate, captafol, captan, kiralaxyl, quinconazole, quintozene, guazatine, cufraneb, cuprobam, glyodin, griseofulvin, climbazole, cresol, kresoxim-methyl, chlozolinate, clotrimazole, chlobenthiazone, chloraniformethan, chloranil, chlorquinox, chloropicrin, chlorfenazole, chlorodinitronaphthalene, chlorothalonil, chloroneb, zarilamid, salicylanilide, cyazofamid, diethyl pyrocarbonate, diethofencarb, cyclafuramid, diclocymet, dichlozoline, diclobutrazol, dichlofluanid, cycloheximide, diclomezine, dicloran, dichlorophen, dichlone, disulfiram, ditalimfos, dithianon, diniconazole, diniconazole-M, zineb, dinocap, dinocton, dinosulfon, dinoterbon, dinobuton, dinopenton, dipyrithione, diphenylamine, difenoconazole, cyflufenamid, diflumetorim, cyproconazole, cyprodinil, cyprofuram, cypendazole, simeconazole, dimethirimol, dimethomorph, cymoxanil, dimoxystrobin, methyl bromide, ziram, silthiofam, streptomycin, spiroxamine, sultropen, sedaxane, zoxamide, dazomet, thiadiazin, tiadinil, thiadifluor, thiabendazole, tioxymid, thiochlorfenphim, thiophanate, thiophanate-methyl, thicyofen, thioquinox, chinomethionat, thifluzamide, thiram, decafentin, tecnazene, tecloftalam, tecoram, tetraconazole, debacarb, dehydroacetic acid, tebuconazole, tebufloquin, dodicin, dodine, dodecyl benzensulfonate bis-ethylene diamine copper(II) (DBEDC), dodemorph, drazoxolon, triadimenol, triadimefon, triazbutil, triazoxide, triamiphos, triarimol, trichlamide, tricyclazole, triticonazole, tridemorph, tributyltin oxide, triflumizole, trifloxystrobin, triforine, tolylfluanid, tolclofos-methyl, natamycin, nabam, nitrothal-isopropyl, nitrostyrene, nuarimol, copper nonylphenol sulfonate, halacrinate, validamycin, valifenalate, harpin protein, bixafen, picoxystrobin, picobenzamide, bithionol, bitertanol, hydroxyisoxazole, hydroxyisoxazole-potassium, binapacryl, biphenyl, piperalin, hymexazol, pyraoxystrobin, pyracarbolid, pyraclostrobin, pyrazophos, pyrametostrobin, pyriofenone, pyridinitril, pyrifenox, pyribencarb, pyrimethanil, pyroxychlor, pyroxyfur, pyroquilon, vinclozolin, famoxadone, fenapanil, fenamidone, fenaminosulf, fenarimol, fenitropan, fenoxanil, ferimzone, ferbam, fentin, fenpiclonil, fenpyrazamine, fenbuconazole, fenfuram, fenpropidin, fenpropimorph, fenhexamid, phthalide, buthiobate, butylamine, bupirimate, fuberidazole, blasticidin-S, furametpyr, furalaxyl, fluacrypyrim, fluazinam, fluoxastrobin, fluotrimazole, fluopicolide, fluopyram, fluoroimide, furcarbanil, fluxapyroxad, fluquinconazole, furconazole, furconazole-cis, fludioxonil, flusilazole, flusulfamide, flutianil, flutolanil, flutriafol, furfural, furmecyclox, flumetover, flumorph, proquinazid, prochloraz, procymidone, prothiocarb, prothioconazole, propamocarb, propiconazole, propineb, furophanate, probenazole, bromuconazole, hexachlorobutadiene, hexaconazole, hexylthiofos, bethoxazin, benalaxyl, benalaxyl-M, benodanil, benomyl, pefurazoate, benquinox, penconazole, benzamorf, pencycuron, benzohydroxamic acid, bentaluron, benthiazole, benthiavalicarb-isopropyl, penthiopyrad, penflufen, boscalid, phosdiphen, fosetyl, fosetyl-Al, polyoxins, polyoxorim, polycarbamate, folpet, formaldehyde, machine oil, maneb, mancozeb, mandipropamid, myclozolin, myclobutanil, mildiomycin, milneb, mecarbinzid, methasulfocarb, metazoxolon, metam, metam-sodium, metalaxyl, metalaxyl-M, metiram, methyl isothiocyanate, meptyldinocap, metconazole, metsulfovax, methfuroxam, metominostrobin, metrafenone, mepanipyrim, mefenoxam, meptyldinocap, mepronil, mebenil, iodomethane, rabenzazole, benzalkonium chloride, inorganic microbicides such as basic copper chloride, basic copper sulfate and silver, sodium hypochlorite, cupric hydroxide, wettable sulfur, calcium polysulfide, potassium hydrogen carbonate, sodium hydrogen carbonate, sulfur, copper sulfate anhydride, nickel dimethyldithiocarbamate, copper compounds such as copper-8-quinolinolate (oxine copper), zinc sulfate and copper sulfate pentahydrate.

Further, examples of the herbicides include 1-naphthylacetamide, 2,4-PA, 2,3,6-TBA, 2,4,5-T, 2,4,5-TB, 2,4-D, 2,4-DB, 2,4-DEB, 2,4-DEP, 3,4-DA, 3,4-DB, 3,4-DP, 4-CPA, 4-CPB, 4-CPP, MCP, MCPA, MCPA-thioethyl, MCPB, ioxynil, aclonifen, azafenidin, acifluorfen, aziprotryne, azimsulfuron, asulam, acetochlor, atrazine, atraton, anisuron, anilofos, aviglycine, abscisic acid, amicarbazone, amidosulfuron, amitrole, aminocyclopyrachlor, aminopyralid, amibuzin, amiprophos-methyl, ametridione, ametryn, alachlor, allidochlor, alloxydim, alorac, isouron, isocarbamid, isoxachlortole, isoxapyrifop, isoxaflutole, isoxaben, isocil, isonoruron, isoproturon, isopropalin, isopolinate, isomethiozin, inabenfide, ipazine, ipfencarbazone, iprymidam, imazaquin, imazapic, imazapyr, imazamethapyr, imazamethabenz, imazamethabenz-methyl, imazamox, imazethapyr, imazosulfuron, indaziflam, indanofan, indolebutyric acid, uniconazole-P, eglinazine, esprocarb, ethametsulfuron, ethametsulfuron-methyl, ethalfluralin, ethiolate, ethychlozate-ethyl, ethidimuron, etinofen, ethephon, ethoxysulfuron, ethoxyfen, etnipromid, ethofumesate, etobenzanid, epronaz, erbon, endothal, oxadiazon, oxadiargyl, oxaziclomefone, oxasulfuron, oxapyrazon, oxyfluorfen, oryzalin, orthosulfamuron, orbencarb, cafenstrole, cambendichlor, carbasulam, carfentrazone, carfentrazone-ethyl, karbutilate, carbetamide, carboxazole, quizalofop, quizalofop-P, quizalofop-ethyl, xylachlor, quinoclamine, quinonamid, quinclorac, quinmerac, cumyluron, cliodinate, glyphosate, glufosinate, glufosinate-P, credazine, clethodim, cloxyfonac, clodinafop, clodinafop-propargyl, chlorotoluron, clopyralid, cloproxydim, cloprop, chlorbromuron, clofop, clomazone, chlomethoxynil, chlomethoxyfen, clomeprop, chlorazifop, chlorazine, cloransulam, chloranocryl, chloramben, cloransulam-methyl, chloridazon, chlorimuron, chlorimuron-ethyl, chlorsulfuron, chlorthal, chlorthiamid, chlortoluron, chlornitrofen, chlorfenac, chlorfenprop, chlorbufam, chlorflurazole, chlorflurenol, chlorprocarb, chlorpropham, chlormequat, chloreturon, chloroxynil, chloroxuron, chloropon, saflufenacil, cyanazine, cyanatryn, di-allate, diuron, diethamquat, dicamba, cycluron, cycloate, cycloxydim, diclosulam, cyclosulfamuron, dichlorprop, dichlorprop-P, dichlobenil, diclofop, diclofop-methyl, dichlormate, dichloralurea, diquat, cisanilide, disul, siduron, dithiopyr, dinitramine, cinidon-ethyl, dinosam, cinosulfuron, dinoseb, dinoterb, dinofenate, dinoprop, cyhalofop-butyl, diphenamid, difenoxuron, difenopenten, difenzoquat, cybutryne, cyprazine, cyprazole, diflufenican, diflufenzopyr, dipropetryn, cypromid, cyperquat, gibberellin, simazine, dimexano, dimethachlor, dimidazon, dimethametryn, dimethenamid, simetryn, simeton, dimepiperate, dimefuron, cinmethylin, swep, sulglycapin, sulcotrione, sulfallate, sulfentrazone, sulfosulfuron, sulfometuron, sulfometuron-methyl, secbumeton, sethoxydim, sebuthylazine, terbacil, daimuron, dazomet, dalapon, thiazafluron, thiazopyr, thiencarbazone, thiencarbazone-methyl, tiocarbazil, tioclorim, thiobencarb, thidiazimin, thidiazuron, thifensulfuron, thifensulfuron-methyl, desmedipham, desmetryn, tetrafluron, thenylchlor, tebutam, tebuthiuron, terbumeton, tepraloxydim, tefuryltrione, tembotrione, delachlor, terbacil, terbucarb, terbuchlor, terbuthylazine, terbutryn, topramezone, tralkoxydim, triaziflam, triasulfuron, tri-allate, trietazine, tricamba, triclopyr, tridiphane, tritac, tritosulfuron, triflusulfuron, triflusulfuron-methyl, trifluralin, trifloxysulfuron, tripropindan, tribenuron-methyl, tribenuron, trifop, trifopsime, trimeturon, naptalam, naproanilide, napropamide, nicosulfuron, nitralin, nitrofen, nitrofluorfen, nipyraclofen, neburon, norflurazon, noruron, barban, paclobutrazol, paraquat, parafluron, haloxydine, haloxyfop, haloxyfop-P, haloxyfop-methyl, halosafen, halosulfuron, halosulfuron-methyl, picloram, picolinafen, bicyclopyrone, bispyribac, bispyribac-sodium, pydanon, pinoxaden, bifenox, piperophos, hymexazol, pyraclonil, pyrasulfotole, pyrazoxyfen, pyrazosulfuron, pyrazosulfuron-ethyl, pyrazolate, bilanafos, pyraflufen-ethyl, pyriclor, pyridafol, pyrithiobac, pyrithiobac-sodium, pyridate, pyriftalid, pyributicarb, pyribenzoxim, pyrimisulfan, primisulfuron, pyriminobac-methyl, pyroxasulfone, pyroxsulam, fenasulam, phenisopham, fenuron, fenoxasulfone, fenoxaprop, fenoxaprop-P, fenoxaprop-ethyl, phenothiol, fenoprop, phenobenzuron, fenthiaprop, fenteracol, fentrazamide, phenmedipham, phenmedipham-ethyl, butachlor, butafenacil, butamifos, buthiuron, buthidazole, butylate, buturon, butenachlor, butroxydim, butralin, flazasulfuron, flamprop, furyloxyfen, prynachlor, primisulfuron-methyl, fluazifop, fluazifop-P, fluazifop-butyl, fluazolate, fluroxypyr, fluothiuron, fluometuron, fluoroglycofen, flurochloridone, fluorodifen, fluoronitrofen, fluoromidine, flucarbazone, flucarbazone-sodium, fluchloralin, flucetosulfuron, fluthiacet, fluthiacet-methyl, flupyrsulfuron, flufenacet, flufenican, flufenpyr, flupropacil, flupropanate, flupoxam, flumioxazin, flumiclorac, flumiclorac-pentyl, flumipropyn, flumezin, fluometuron, flumetsulam, fluridone, flurtamone, fluroxypyr, pretilachlor, proxan, proglinazine, procyazine, prodiamine, prosulfalin, prosulfuron, prosulfocarb, propaquizafop, propachlor, propazine, propanil, propyzamide, propisochlor, prohydrojasmon, propyrisulfuron, propham, profluazol, profluralin, prohexadione-calcium, propoxycarbazone, propoxycarbazone-sodium, profoxydim, bromacil, brompyrazon, prometryn, prometon, bromoxynil, bromofenoxim, bromobutide, bromobonil, florasulam, hexachloroacetone, hexazinone, pethoxamid, benazolin, penoxsulam, pebulate, beflubutamid, vernolate, perfluidone, bencarbazone, benzadox, benzipram, benzylaminopurine, benzthiazuron, benzfendizone, bensulide, bensulfuron-methyl, benzoylprop, benzobicyclon, benzofenap, benzofluor, bentazone, pentanochlor, benthiocarb, pendimethalin, pentoxazone, benfluralin, benfuresate, fosamine, fomesafen, foramsulfuron, forchlorfenuron, maleic hydrazide, mecoprop, mecoprop-P, medinoterb, mesosulfuron, mesosulfuron-methyl, mesotrione, mesoprazine, methoprotryne, metazachlor, methazole, metazosulfuron, methabenzthiazuron, metamitron, metamifop, metam, methalpropalin, methiuron, methiozolin, methiobencarb, methyldymron, metoxuron, metosulam, metsulfuron, metsulfuron-methyl, metflurazon, metobromuron, metobenzuron, methometon, metolachlor, metribuzin, mepiquat-chloride, mefenacet, mefluidide, monalide, monisouron, monuron, monochloroacetic acid, monolinuron, molinate, morfamquat, iodosulfuron, iodosulfuron-methyl-sodium, iodobonil, iodomethane, lactofen, linuron, rimsulfuron, lenacil, rhodethanil, calcium peroxide and methyl bromide.

Examples of the biopesticides include viral formulations such as nuclear polyhedrosis viruses (NPV), granulosis viruses (GV), cytoplasmic polyhedrosis viruses (CPV) and entomopox viruses (EPV); microbial pesticides used as an insecticide or a nematicide, such as *Monacrosporium phymatophagum, Steinernema carpocapsae, Steinernema kushidai* and *Pasteuria penetrans*; microbial pesticides used as a microbicide, such as *Trichoderma lignorum, Agrobacterium radiobactor, avirulent Erwinia carotovora* and *Bacillus subtilis*; and biopesticides used as a herbicide, such as *Xanthomonas campestris*. A combined use of the agricultural and horticultural insecticide and microbicide of the present invention with the foregoing biopesticide as a mixture can be expected to provide the same effect as above.

Other examples of the biopesticides include natural predators such as *Encarsia formosa*, *Aphidius colemani*, *Aphidoletes aphidimyza*, *Diglyphus isaea*, *Dacnusa sibirica*, *Phytoseiulus persimilis*, *Amblyseius cucumeris* and *Orius sauteri*; microbial pesticides such as *Beauveria brongniartii*; and pheromones such as (Z)-10-tetradecenyl acetate, (E,Z)-4,10-tetradecadienyl acetate, (Z)-8-dodecenyl acetate, (Z)-11-tetradecenyl acetate, (Z)-13-icosen-10-one and 14-methyl-1-octadecene.

Hereinafter, the production examples of representative compounds of the present invention and their intermediates will be described in more detail, but the present invention is not limited only to these examples. THF, DMF and DMSO stand for tetrahydrofuran, dimethylformamide and dimethyl sulfoxide, respectively.

EXAMPLES

Example 1-1

Production method of 2-fluoro-N-methyl-4-(trifluoromethyl)-N-(5-(trifluoromethyl)pyridin-2-yl)benzamide

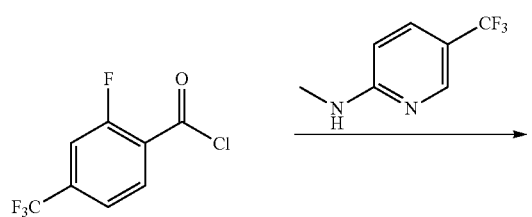

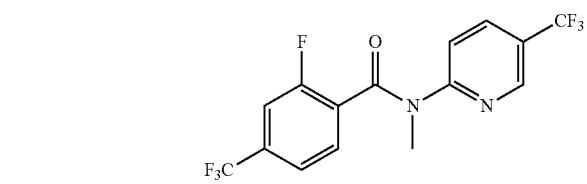

2-Fluoro-4-trifluoromethyl benzoyl chloride (409 mg) and a THF (1 mL) solution were added to a mixture of N-methyl-5-(trifluoromethyl)pyridin-2-amine (264 mg), THF (4 mL) and triethylamine (1 mL) under ice cooling. After heating to room temperature, N,N-dimethyl aminopyridine (50 mg) was added, and the resulting mixture was stirred for 3 hours. Water was added to the reaction mixture, and extraction with ethyl acetate was performed. The organic layer was dried over anhydrous magnesium sulfate and then concentrated in vacuo. The resulting residue was subjected to column chromatography to give the desired compound (260 mg, yield: 47%).

Example 1-2

Production method of 2-(ethylthio)-N-methyl-4-(trifluoromethyl)-N-(5-(trifluoromethyl)pyridin-2-yl)benzamide (compound number 1-1)

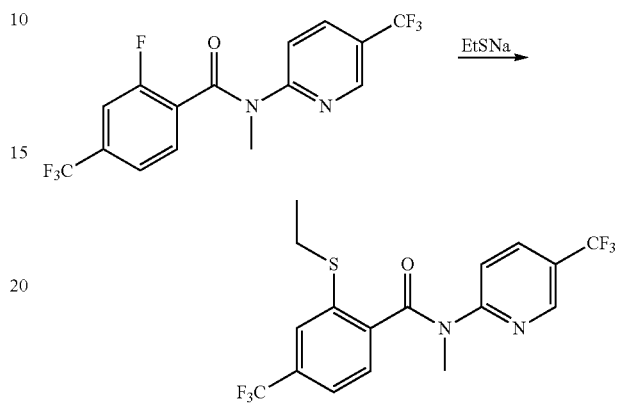

Sodium ethanethiolate (66 mg) was added to a mixture of the compound (210 mg) produced in the previous step and DMF (2 mL), and the resulting mixture was stirred at room temperature for 30 minutes. Water was added to the reaction mixture, and extraction with ethyl acetate was performed. The organic layer was dried over anhydrous magnesium sulfate and then concentrated in vacuo. The resulting residue was subjected to column chromatography to give the desired compound (101 mg, yield: 44%).

Example 2

Production method of 2-(ethylsulfinyl)-N-methyl-4-(trifluoromethyl)-N-(5-(trifluoromethyl)pyridin-2-yl)benzamide (compound number 1-2) and 2-(ethylsulfonyl)-N-methyl-4-(trifluoromethyl)-N-(5-(trifluoromethyl)pyridin-2-yl)benzamide (compound number 1-3)

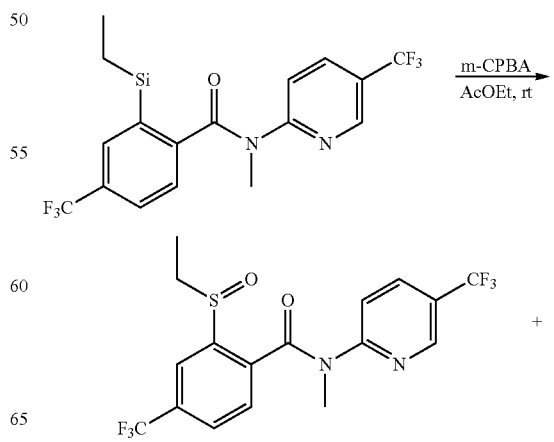

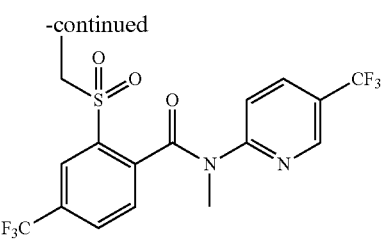

A mixture of the compound (101 mg) produced in the previous step, ethyl acetate (2 mL) and m-chloroperoxybenzoic acid (86 mg) was stirred at room temperature for 2 hours. Ten drops of formamide dimethyl dithioacetal S-oxide were added to the reaction mixture, and the resulting mixture was concentrated in vacuo. The resulting residue was subjected to column chromatography to give the desired compounds 1-2 (42 mg, yield: 42%) and 1-3 (58 mg, yield: 58%).

Reference Example 1

Production method of 2-amino-5-(pentafluoroethyl)pyridine

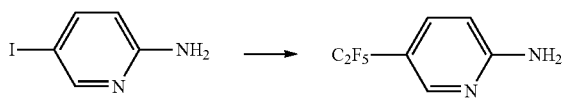

A 100-mL autoclave was charged with 2-amino-5-iodopyridine (20 mmol, 4.4 g), reduced copper (60 mmol, 3.36 g), DMSO (30 mL) and pentafluoroethyl iodide (30 mmol, 7.35 g) and then sealed. The temperature was gradually raised from room temperature, and the mixture in the autoclave was stirred under heating at 120° C. for 2 hours, and subsequently at 140° C. for 2 hours. The reaction system was cooled to room temperature, and the mixture in the autoclave was then filtered through Celite. Water and ethyl acetate were added to the filtrate, and extraction with ethyl acetate was performed. The organic layer was dried over sodium sulfate, filtered and concentrated. The concentrate was subjected to column chromatography to give the desired compound, 2-amino-5-(pentafluoroethyl) pyridine (1.87 g, 44%).

Reference Example 2

Production method of 5-(trifluoromethyl)pyridine-2-carboxylic acid ester

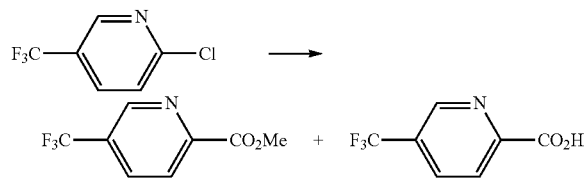

A 100-mL autoclave was charged successively with 2-chloro-5-(trifluoromethyl)pyridine (24.55 g, 135.26 mmol), $PdCl_2(PPh_3)_2$ (474 mg, 0.5 mol %), diphenylphosphinobutane (DPPB, 1.45 g, 2.5 mol %), triethylamine (24 mL) and methanol (50 mL). The atmosphere in the reaction system was replaced by carbon monoxide 3 times. After charging with carbon monoxide to a pressure of 3 atmospheres, the mixture in the autoclave was stirred under heating at 120° C. for 3 hours. After cooling to room temperature, water and ethyl acetate were added to the reaction mixture, and extraction was repeated about 3 times, followed by drying and concentration. The concentrate was subjected to column chromatography (from hexane:ethyl acetate=5:1 to ethyl acetate) to give a methyl ester compound (21.8 g, 79%) and a carboxylic acid compound (3.86 g, 15%).

Hereinafter, formulation examples are shown, but the present invention is not limited thereto. In the formulation examples, the "parts" means parts by weight.

Formulation Example 1

| | |
|---|---|
| Compound (I) of the present invention | 1 |
| Xylene | 70 parts |
| N-methyl pyrrolidone | 10 parts |
| Mixture of polyoxyethylene nonylphenyl ether and calcium alkylbenzene sulfonate | 10 parts |

The above ingredients are uniformly mixed for dissolution to give an emulsifiable concentrate.

Formulation Example 2

| | |
|---|---|
| Compound (I) of the present invention | 3 parts |
| Clay powder | 82 parts |
| Diatomite powder | 15 parts |

The above ingredients are uniformly mixed and then pulverized to give a dust.

Formulation Example 3

| | |
|---|---|
| Compound (I) of the present invention | 5 parts |
| Mixture of bentonite powder and clay powder | 90 parts |
| Calcium lignosulfonate | 5 parts |

The above ingredients are uniformly mixed. After addition of an appropriate volume of water, the mixture is kneaded, granulated and dried to give a granule.

Formulation Example 4

| | |
|---|---|
| Compound (I) of the present invention | 20 parts |
| Kaolin and synthetic high-dispersion silicic acid | 75 parts |
| Mixture of polyoxyethylene nonylphenyl ether and calcium alkylbenzene sulfonate | 5 parts |

The above ingredients are uniformly mixed and then pulverized to give a wettable powder.

Hereinafter, test examples in connection with the present invention are shown, but the present invention is not limited thereto.

Test Example 1

Test of Control Effect on *Myzus persicae*

Chinese cabbage plants were planted in plastic pots (diameter: 8 cm, height: 8 cm), green peach aphids (*Myzus persicae*) were propagated on the plants, and the number of surviving green peach aphids in each pot was counted. The amide compounds represented by the general formula (I) of the present invention or salts thereof were separately dispersed in water and diluted to 500 ppm, and the agrochemical dispersions were applied to the foliage of the potted Chinese cabbage plants. After the plants were air-dried, the pots were kept in a greenhouse. At 6 days after the foliar application, the number of surviving green peach aphids on the Chinese cabbage plant in each pot was counted, the control rate was calculated according to the formula shown below, and the control effect was evaluated according to the criteria shown below.

Control rate=100−{($T$×$Ca$)/($Ta$×$C$)}×100

$Ta$: the number of survivors before the foliar application in a treatment plot
$T$: the number of survivors after the foliar application in a treatment plot
$Ca$: the number of survivors before the foliar application in a non-treatment plot
$C$: the number of survivors after the foliar application in a non-treatment plot Criteria
A: the control rate is 100%.
B: the control rate is 90 to 99%.
C: the control rate is 80 to 89%.
D: the control rate is 50 to 79%.

As a result, the compounds 1-1, 1-2, 1-3, 1-4, 1-5, 1-6, 1-8, 1-9, 1-16, 1-20, 1-21, 1-22, 1-23, 1-24, 1-25, 1-26, 1-36, 1-37, 1-42, 1-43, 1-44, 1-45, 1-46, 2-1, 2-3, 2-4, 2-6, 3-1, 3-2, 3-3, 3-7, 3-8, 3-9, 3-10, 3-11, 3-66, 3-68, 3-75, 3-78, 3-79, 3-80, 3-81, 3-82, 3-83, 3-84, 3-85, 3-86, 3-87, 3-88 and 8-1 of the present invention showed the activity level evaluated as A.

Test Example 2

Insecticidal Test on *Laodelphax striatella*

The amide compounds represented by the general formula (I) of the present invention or salts thereof were separately dispersed in water and diluted to 500 ppm, and rice plant seedlings (variety: Nihonbare) were dipped in the agrochemical dispersions for 30 seconds. After air-dried, each seedling was put into a separate glass test tube and inoculated with ten 3rd-instar larvae of *Laodelphax striatella*, and then the glass test tubes were capped with cotton plugs. At 8 days after the inoculation, the numbers of surviving larvae and dead larvae were counted, the corrected mortality rate was calculated according to the formula shown below, and the insecticidal effect was evaluated according to the criteria of Test Example 1.

Corrected mortality rate (%)=100×(Survival rate in a non-treatment plot−Survival rate in a treatment plot)/Survival rate in a non-treatment plot As a result, the compounds 1-1, 1-2, 1-3, 1-4, 1-5, 1-6, 1-7, 1-16, 1-17, 1-18, 1-20, 1-21, 1-22, 1-23, 1-24, 1-25, 1-26, 1-36, 1-38, 1-42, 1-43, 1-44, 1-45, 1-46, 2-1, 2-2, 2-3, 2-4, 2-6, 2-16, 3-1, 3-2, 3-3, 3-4, 3-7, 3-9, 3-10, 3-11, 3-66, 3-68, 3-75, 3-78, 3-79, 3-80, 3-81, 3-82, 3-83, 3-84, 3-85, 3-86, 3-87 and 3-88 of the present invention showed the activity level evaluated as A.

Test Example 3

Insecticidal Test on *Plutella xylostella*

Adults of *Plutella xylostella* were released onto Chinese cabbage seedlings and allowed to lay eggs thereon. At 2 days after the release of the adults, the Chinese cabbage seedlings with laid eggs were dipped for about 30 seconds in agrochemical formulations diluted to 500 ppm, each of which contained a different amide compound represented by the general formula (I) of the present invention as an active ingredient. After air-dried, the seedlings were kept in a thermostatic chamber at 25° C. At 6 days after the dip treatment, the number of hatched larvae per plot was counted, the mortality rate was calculated according to the formula shown below, and the insecticidal effect was evaluated according to the criteria of Test Example 1. This test was conducted in triplicate using 10 adults of *Plutella xylostella* per plot.

Corrected mortality rate (%)=100×(Number of hatched larvae in a non-treatment plot−Number of hatched larvae in a treatment plot)/Number of hatched larvae in a non-treatment plot As a result, the compounds 1-1, 1-2, 1-3, 1-4, 1-5, 1-6, 1-7, 1-8, 1-9, 1-10, 1-12, 1-13, 1-16, 1-17, 1-18, 1-20, 1-21, 1-22, 1-23, 1-24, 1-25, 1-26, 1-36, 1-37, 1-38, 1-42, 1-43, 1-44, 1-45, 1-46, 2-1, 2-2, 2-3, 2-4, 2-6, 2-10, 2-12, 2-16, 2-21, 3-1, 3-2, 3-3, 3-4, 3-6, 3-7, 3-8, 3-9, 3-10, 3-11, 3-21, 3-24, 3-66, 3-68, 3-75, 3-78, 3-79, 3-80, 3-81, 3-82, 3-83, 3-84, 3-85, 3-86, 3-87, 3-88, 4-2, 4-5, 4-6, 4-9, 4-10, 4-14 and 9-4 of the present invention showed the activity level evaluated as A.

Test Example 4

Acaricidal Test on *Tetranychus urticae*

Agrochemical formulations containing different amide compounds represented by the general formula (I) of the present invention or salts thereof as an active ingredient were separately diluted to 500 ppm, and kidney bean leaf disks of 2 cm in diameter were dipped in the diluted agrochemical formulations for about 30 seconds. After air-dried, each leaf disk was placed on a piece of wet filter paper, and inoculated with ten female adults of *Tetranychus urticae*. Two days later, the number of survivors was counted. The corrected mortality rate was calculated according to the formula shown below, and the acaricidal effect was evaluated according to the criteria shown below. This test was conducted in duplicate under the condition of 25° C.

Corrected mortality rate (%)=100×(Number of survivors in a non-treatment plot−Number of survivors in a treatment plot)/Number of survivors in a non-treatment plot Criteria
A: the corrected motality rate is 100%.
B: the corrected motality rate is 90 to 99%.
C: the corrected motality rate is 80 to 89%.
D: the corrected motality rate is 50 to 79%.

The results of the above test revealed that the compounds 1-1, 1-4, 1-5, 1-6, 1-8, 1-9, 1-25, 1-26, 3-2, 3-3, 3-4, 3-6, 3-10, 3-11 and 3-21 of the present invention showed the activity level evaluated as D or higher.

Test Example 5

Nematicidal Test on *Meloidogyne incognita*

Agrochemical formulations containing different amide compounds represented by the general formula (I) of the present invention or salts thereof as an active ingredient were separately diluted to a concentration of 500 ppm. The diluted agrochemical formulations (1 mL) were drenched into the soil around the foot of potted melon seedlings. At one day after the agrochemical treatment, an aqueous suspension of *Meloidogyne incognita* (about 500 worms/mL) was drenched into the soil for inoculation both in a treatment plot and in a non-treatment plot. The inoculated pots were kept in a greenhouse at 25° C. At 8 days after the inoculation, the root of each seedling was washed with water, the number of root nodules was counted, and the nematicidal effect was evaluated according to the following criteria.

Criteria

A: the percentage of the number of root nodules relative to the non-treatment plot is 0%.
B: the percentage of the number of root nodules relative to the non-treatment plot is 1 to 10%.
C: the percentage of the number of root nodules relative to the non-treatment plot is 11 to 20%.
D: the percentage of the number of root nodules relative to the non-treatment plot is 21 to 50%.

The results of the above test revealed that the compounds 1-1, 1-2, 1-3, 1-4, 1-5, 1-6, 1-7, 1-8, 1-9, 1-10, 1-12, 1-13, 1-21, 1-24, 1-25, 1-26, 1-44, 2-1, 2-3, 3-2, 3-3, 3-6, 3-7, 3-8, 3-9, 3-10, 3-11, 3-12, 3-21, 3-22 and 4-5 of the present invention showed the activity level evaluated as D or higher.

Test Example 6

Test of Control Effect on Wheat Powdery Mildew

Agrochemical formulations prepared from the compounds of the present invention according to Formulation Example 1 were diluted with water to a predetermined concentration. The diluted agrochemical formulations were applied to the foliage of wheat plants (variety: Nourin No. 61) grown to the one- to two-leaf stage in pots of 6 cm in diameter. The application amount was 10 mL per pot. After air-dried, the wheat plants were inoculated by sprinkling the conidia of the wheat powdery mildew fungus *Erysiphe graminis*, and kept in a greenhouse. At 7 days after the inoculation, the control effect was evaluated according to the criteria shown below.

Control rate (%)=100×(Average percent lesion area in a non-treatment plot−Average percent lesion area in a treatment plot)/Average percent lesion area in a non-treatment plot Criteria
A: the control rate is 100%.
B: the control rate is 90 to 99%.
C: the control rate is 70 to 89%.
D: the control rate is 50 to 69%.

The results of the above test revealed that the compounds 1-5, 1-6, 1-8, 1-9, 1-10, 1-14, 1-15, 1-21, 1-22, 1-23, 1-24, 1-45, 1-46, 2-1, 3-2, 3-3, 3-4, 3-6, 3-8, 3-9, 3-10, 3-11, 3-12, 3-13, 3-16, 3-17, 3-19, 3-27, 3-28, 3-29, 3-30, 3-31, 3-32, 3-33, 3-34, 3-37, 3-38, 3-39, 3-40, 3-42, 3-43, 3-44, 3-47, 3-48, 3-49, 3-50, 3-52, 3-53, 3-56, 3-57, 3-59, 4-2, 4-3, 4-4, 4-5, 4-6, 4-7, 4-14, 4-15, 4-16, 4-17, 4-18, 4-19, 4-20, 4-21, 4-22, 4-23, 4-25, 4-26, 4-27, 4-28, 5-1, 5-2, 5-3, 5-8, 5-9, 5-10, 5-11, 5-15, 5-17, 5-18, 5-19, 5-25, 5-27, 5-26, 5-28, 5-29, 5-30, 5-31, 5-32, 5-33, 5-34, 5-35, 5-36, 5-37, 5-38, 5-39, 5-42, 5-43, 5-44, 5-47, 5-49, 5-50, 5-51, 5-52, 5-55, 5-58, 5-59, 5-60, 5-61, 5-64, 5-67, 5-68, 5-69, 5-70, 5-71, 5-72, 5-73, 5-75, 5-76, 5-77, 5-78, 5-79, 5-80, 5-81, 5-82, 6-1, 6-2, 6-3, 6-4, 6-5, 6-6, 6-7, 6-9, 6-10, 6-12, 6-13, 6-15, 6-16, 6-19, 6-20, 6-21, 6-22, 6-23, 6-24, 8-1, 9-1, 9-2, 9-3, 9-4, 9-8 and 9-9 of the present invention showed the activity level evaluated as D or higher at a concentration of 200 ppm. Among them, the compounds 1-8, 1-9, 1-23, 1-24, 1-45, 1-46, 2-1, 3-2, 3-4, 3-8, 3-10, 3-11, 3-27, 3-29, 3-30, 3-33, 3-37, 3-38, 3-39, 3-40, 3-42, 3-43, 3-44, 3-48, 3-49, 3-52, 3-53, 3-56, 3-57, 3-59, 4-2, 4-3, 4-4, 4-6, 4-7, 4-14, 4-15, 4-17, 4-18, 4-19, 4-20, 4-23, 4-25, 4-26, 4-28, 5-2, 5-9, 5-10, 5-11, 5-17, 5-18, 5-19, 5-25, 5-26, 5-28, 5-29, 5-30, 5-31, 5-32, 5-33, 5-34, 5-36, 5-37, 5-38, 5-39, 5-42, 5-43, 5-44, 5-47, 5-49, 5-52, 5-55, 5-58, 5-60, 5-61, 5-67, 5-68, 5-69, 5-72, 5-75, 5-76, 5-78, 5-79, 5-80, 5-81, 5-82, 6-1, 6-2, 6-3, 6-4, 6-5, 6-6, 6-7, 6-9, 6-10, 6-13, 6-15, 6-16, 6-19, 6-20, 6-21, 8-1, 9-1, 9-2, 9-3, 9-4, 9-8 and 9-9 of the present invention showed the activity level evaluated as A at a concentration of 200 ppm.

INDUSTRIAL APPLICABILITY

The amide compound of the present invention is highly effective for the control of a wide range of agricultural and horticultural pests and thus is useful.

The invention claimed is:
1. A method for controlling an agricultural and horticultural fungal disease, comprising applying, to plants or soil, an effective amount of an amide compound represented by the formula:

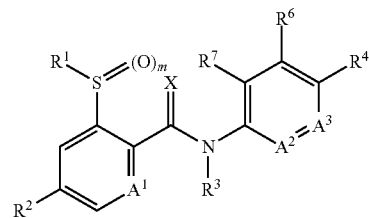

wherein
$R^1$ represents
(a1) a $(C_1-C_6)$ alkyl group;
(a2) a $(C_2-C_6)$ alkenyl group;
(a3) a $(C_2-C_6)$ alkynyl group;
(a4) a $(C_3-C_6)$ cycloalkyl $(C_1-C_6)$ alkyl group;
(a6) a halo $(C_2-C_6)$ alkenyl group;
(a7) a halo $(C_2-C_6)$ alkynyl group; or
(a8) a halo $(C_3-C_6)$ cycloalkyl $(C_1-C_6)$ alkyl group,
$R^2$ and $R^4$ may be the same or different, and each represent
(b1) a halogen atom;
(b2) a cyano group;
(b3) a nitro group;
(b4) a $(C_1-C_6)$ alkyl group;
(b5) a halo $(C_1-C_6)$ alkyl group;
(b6) a $(C_3-C_6)$ cycloalkyl group;
(b7) a halo $(C_3-C_6)$ cycloalkyl group;
(b8) a $(C_1-C_6)$ alkoxy group;
(b9) a halo $(C_1-C_6)$ alkoxy group;
(b10) a $(C_1-C_6)$ alkylthio group;
(b11) a $(C_1-C_6)$ alkylsulfinyl group;
(b12) a $(C_1-C_6)$ alkylsulfonyl group;
(b13) a halo $(C_1-C_6)$ alkylthio group;
(b14) a halo $(C_1-C_6)$ alkylsulfinyl group;
(b15) a halo $(C_1-C_6)$ alkylsulfonyl group;
(b16) a $(C_1-C_6)$ alkoxy halo $(C_1-C_6)$ alkyl group;
(b17) a pentafluorothio group;

(b18) a tri-($C_1$-$C_6$) alkylsilyl group, wherein the alkyl groups of the tri-($C_1$-$C_6$) alkyl moiety may be the same or different; or
(b19) a hydrogen atom,
$R^3$ represents
(c1) a hydrogen atom;
(c2) a ($C_1$-$C_6$) alkyl group;
(c3) a ($C_3$-$C_6$) cycloalkyl group;
(c4) a ($C_1$-$C_6$) alkoxy group;
(c5) a halo ($C_1$-$C_6$) alkyl group;
(c6) a ($C_3$-$C_6$) cycloalkyl ($C_1$-$C_6$) alkyl group;
(c7) a ($C_1$-$C_6$) alkoxy ($C_1$-$C_6$) alkyl group;
(c8) a ($C_1$-$C_6$) alkoxycarbonyl group;
(c9) a ($C_1$-$C_6$) alkylthio ($C_1$-$C_6$) alkyl group;
(c10) a ($C_1$-$C_6$) alkylsulfinyl ($C_1$-$C_6$) alkyl group;
(c11) a ($C_1$-$C_6$) alkylsulfonyl ($C_1$-$C_6$) alkyl group;
(c12) a ($C_2$-$C_6$) alkenyl group;
(c13) a ($C_2$-$C_6$) alkynyl group;
(c14) a cyano ($C_1$-$C_6$) alkyl group;
(c15) a ($C_1$-$C_6$) alkoxy ($C_1$-$C_6$) alkoxy ($C_1$-$C_6$) alkyl group;
(c16) a ($C_1$-$C_6$) alkylcarbonyl group; or
(c17) a ($C_3$-$C_6$) cycloalkyl ($C_1$-$C_6$) carbonyl group,
m represents 0, 1 or 2,
$A^1$, $A^2$ and $A^3$ may be the same or different, and each represent a nitrogen atom or a C—$R^5$ group, wherein $R^5$ represents
(d1) a hydrogen atom,
$R^6$ represents
(e1) a hydrogen atom,
$R^7$ represents
(e3) a cyano group;
(e4) a ($C_1$-$C_6$) alkyl group;
(e5) a ($C_1$-$C_6$) alkoxy group;
(e6) a ($C_1$-$C_6$) alkylthio group;
(e7) a ($C_1$-$C_6$) alkylsulfinyl group;
(e8) a ($C_1$-$C_6$) alkylsulfonyl group;
(e9) a ($C_2$-$C_6$) alkenyl group;
(e10) a ($C_2$-$C_6$) alkynyl group;
(e11) a ($C_3$-$C_6$) cycloalkyl group; or
(e12) a tri-($C_1$-$C_6$) alkylsilyl ($C_2$-$C_6$) alkynyl group, wherein the alkyl groups of the tri-($C_1$-$C_6$) alkyl moiety may be the same or different, and
X is an oxygen atom or a sulfur atom, or a salt thereof.

2. The method according to claim 1, wherein
$R^1$ represents
(a1) a ($C_1$-$C_6$) alkyl group,
$R^2$ and $R^4$ may be the same or different, and each represent
(b1) a halogen atom;
(b4) a ($C_1$-$C_6$) alkyl group;
(b5) a halo ($C_1$-$C_6$) alkyl group;
(b8) a ($C_1$-$C_6$) alkoxy group;
(b9) a halo ($C_1$-$C_6$) alkoxy group;
(b10) a ($C_1$-$C_6$) alkylthio group;
(b12) a ($C_1$-$C_6$) alkylsulfonyl group;
(b13) a halo ($C_1$-$C_6$) alkylthio group;
(b16) a ($C_1$-$C_6$) alkoxy halo ($C_1$-$C_6$) alkyl group;
(b18) a tri-($C_1$-$C_6$) alkylsilyl group, wherein the alkyl groups of the tri-($C_1$-$C_6$) alkyl moiety may be the same or different; or
(b19) a hydrogen atom,
$R^3$ represents
(c1) a hydrogen atom;
(c2) a ($C_1$-$C_6$) alkyl group;
(c3) a ($C_3$-$C_6$) cycloalkyl group;
(c4) a ($C_1$-$C_6$) alkoxy group;
(c7) a ($C_1$-$C_6$) alkoxy ($C_1$-$C_6$) alkyl group;
(c8) a ($C_1$-$C_6$) alkoxycarbonyl group;
(c9) a ($C_1$-$C_6$) alkylthio ($C_1$-$C_6$) alkyl group;
(c10) a ($C_1$-$C_6$) alkylsulfinyl ($C_1$-$C_6$) alkyl group;
(c12) a ($C_2$-$C_6$) alkenyl group;
(c14) a cyano ($C_1$-$C_6$) alkyl group; or
(c15) a ($C_1$-$C_6$) alkoxy ($C_1$-$C_6$) alkoxy ($C_1$-$C_6$) alkyl group,
m represents 0, 1 or 2,
$A^1$, $A^2$ and $A^3$ may be the same or different, and each represent a nitrogen atom or a C—$R^5$ group, wherein $R^5$ represents
(d1) a hydrogen atom,
$R^6$ represents
(e1) a hydrogen atom,
$R^7$ represents
(e3) a cyano group;
(e4) a ($C_1$-$C_6$) alkyl group;
(e5) a ($C_1$-$C_6$) alkoxy group;
(e6) a ($C_1$-$C_6$) alkylthio group; or
(e7) a ($C_1$-$C_6$) alkylsulfinyl group, and
X is an oxygen atom or a sulfur atom.

3. The method according to claim 1, wherein
$R^1$ represents
(a1) a ($C_1$-$C_6$) alkyl group,
$R^2$ and $R^4$ may be the same or different, and each represent
(b1) a halogen atom;
(b5) a halo ($C_1$-$C_6$) alkyl group;
(b8) a ($C_1$-$C_6$) alkoxy group;
(b9) a halo ($C_1$-$C_6$) alkoxy group;
(b10) a ($C_1$-$C_6$) alkylthio group;
(b12) a ($C_1$-$C_6$) alkylsulfonyl group;
(b13) a halo ($C_1$-$C_6$) alkylthio group;
(b16) a ($C_1$-$C_6$) alkoxy halo ($C_1$-$C_6$) alkyl group;
(b18) a tri-($C_1$-$C_6$) alkylsilyl group, wherein the alkyl groups of the tri-($C_1$-$C_6$) alkyl moiety may be the same or different; or
(b19) a hydrogen atom,
$R^3$ represents
(c1) a hydrogen atom;
(c2) a ($C_1$-$C_6$) alkyl group;
(c3) a ($C_3$-$C_6$) cycloalkyl group;
(c7) a ($C_1$-$C_6$) alkoxy ($C_1$-$C_6$) alkyl group;
(c8) a ($C_1$-$C_6$) alkoxycarbonyl group;
(c9) a ($C_1$-$C_6$) alkylthio ($C_1$-$C_6$) alkyl group;
(c10) a ($C_1$-$C_6$) alkylsulfinyl ($C_1$-$C_6$) alkyl group;
(c12) a ($C_2$-$C_6$) alkenyl group;
(c14) a cyano ($C_1$-$C_6$) alkyl group; or
(c15) a ($C_1$-$C_6$) alkoxy ($C_1$-$C_6$) alkoxy ($C_1$-$C_6$) alkyl group,
m represents 0, 1 or 2,
$A^1$, $A^2$ and $A^3$ may be the same or different, and each represent a nitrogen atom or a C—$R^5$ group, wherein $R^5$ represents
(d1) a hydrogen atom,
$R^6$ represents
(e1) a hydrogen atom,
$R^7$ represents
(e4) a ($C_1$-$C_6$) alkyl group;
(e5) a ($C_1$-$C_6$) alkoxy group; or
(e6) a ($C_1$-$C_6$) alkylthio group, and
X is an oxygen atom or a sulfur atom.

4. The method according to claim 1, wherein $A^2$ is a nitrogen atom and $A^3$ is CH.

5. The method according to claim 2, wherein $A^2$ is a nitrogen atom and $A^3$ is CH.

6. The method according to claim 3, wherein $A^2$ is a nitrogen atom and $A^3$ is CH.

7. The method according to claim 1, wherein $A^2$ and $A^3$ are nitrogen atoms.

8. The method according to claim 2, wherein $A^2$ and $A^3$ are nitrogen atoms.

9. The method according to claim 3, wherein $A^2$ and $A^3$ are nitrogen atoms.

10. The method according to claim 1, wherein $A^2$ and $A^3$ are CH groups.

11. The method according to claim 2, wherein $A^2$ and $A^3$ are CH groups.

12. The method according to claim 3, wherein $A^2$ and $A^3$ are CH groups.

13. The method according to claim 1, wherein the agricultural and horticultural fungal disease is powdery mildew.

* * * * *